Figure 1:
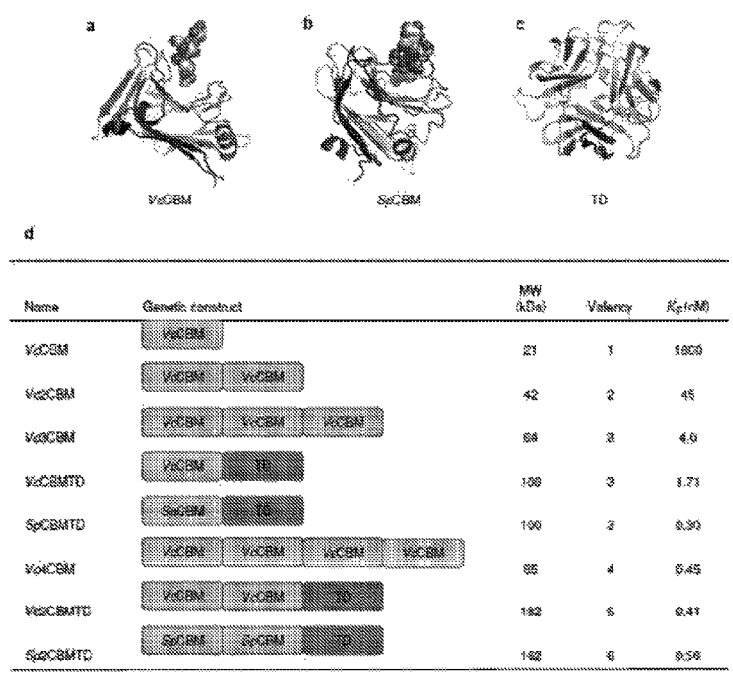

(12) United States Patent
Connaris et al.

(10) Patent No.: US 11,819,534 B2
(45) Date of Patent: Nov. 21, 2023

(54) VIRAL TREATMENT

(71) Applicant: Pneumagen Ltd, Fife (GB)

(72) Inventors: Helen Connaris, St. Andrews (GB); Lei Yang, Fife (GB); Jane Alexandra Potter, Fife (GB)

(73) Assignee: Pneumagen Ltd, Fife (GB)

( * ) Notice: Subject to any disclaimer, the term of this patent is extended or adjusted under 35 U.S.C. 154(b) by 105 days.

(21) Appl. No.: 15/733,545

(22) PCT Filed: Feb. 27, 2019

(86) PCT No.: PCT/GB2019/050546
§ 371 (c)(1),
(2) Date: Aug. 25, 2020

(87) PCT Pub. No.: WO2019/166802
PCT Pub. Date: Sep. 6, 2019

(65) Prior Publication Data
US 2020/0390851 A1    Dec. 17, 2020

(30) Foreign Application Priority Data
Feb. 27, 2018 (GB) .................................... 1803197

(51) Int. Cl.
| A61K 38/16 | (2006.01) |
| A61P 31/12 | (2006.01) |
| A61K 38/47 | (2006.01) |

(52) U.S. Cl.
CPC ............ *A61K 38/164* (2013.01); *A61K 38/47* (2013.01); *A61P 31/12* (2018.01)

(58) Field of Classification Search
None
See application file for complete search history.

(56) References Cited

U.S. PATENT DOCUMENTS

| 9,066,894 | B2 * | 6/2015 | Connaris .......... G01N 33/56911 |
| 11,466,059 | B2 | 10/2022 | Connaris et al. |
| 2011/0182875 | A1 | 7/2011 | Fang et al. |
| 2011/0269670 | A1 | 11/2011 | Connaris et al. |
| 2023/0036052 | A1 | 2/2023 | Connaris et al. |

FOREIGN PATENT DOCUMENTS

| EP | 3241898 | 11/2017 |
| WO | 2010/029312 | 3/2010 |
| WO | 2015/110831 | 7/2015 |
| WO | 2019138222 A1 | 7/2019 |

OTHER PUBLICATIONS

Mastrangelo and Hegele, "The RSV fusion receptor: not what everyone expected it to be", Microbes and Infection 14: 1205-1210 (Year: 2012).*
Jans et al. "Siglec-1 inhibits RSV-induced interferon gamma production by adult T cells in contrast to newborn T cells" European J of Immunology, 48(4): 621-631 (2018).
United Kingdom Search Report corresponding to GB1803197.1; dated Oct. 31, 2018 (4 pages).
International Search Report and Written Opinion corresponding to PCT/GB2019/050546; dated May 16, 2019 (14 pages).
Alias, N. "Multivalent sialic acid binding proteins as novel therapeutics for influenza and parainfluenza infection" Doctoral Thesis, University of St. Andrews, 2014 (252 pages).
Connaris et al. "Prevention of influenza by targeting host receptors using engineered proteins" PNAS, 111(17): 6401-6406 (2014).
International Preliminary Report on Patentability corresponding to PCT/GB2019/050546; dated Aug. 27, 2020 (8 pages).
Connaris, Helen, et al., "Enhancing the Receptor Affinity of the Sialic Acid-binding Domain of Vibrio cholerae Sialidase through Multivalency", The Journal of Biological Chemistry. 284(11), 2009, 7339-7351.
Fu, Hailong, et al., "Increasing Protein Stability By Improving Betaturns", Proteins. 77(3), 2009, 491-498.
Harris, James, et al., "Binding and entry of respiratory syncytial virus into host cells and initiation of the innate immune response", Cellular Microbiology. 5(10), 2003, 671-680.
Hilton, Louise, et al., "The NPro

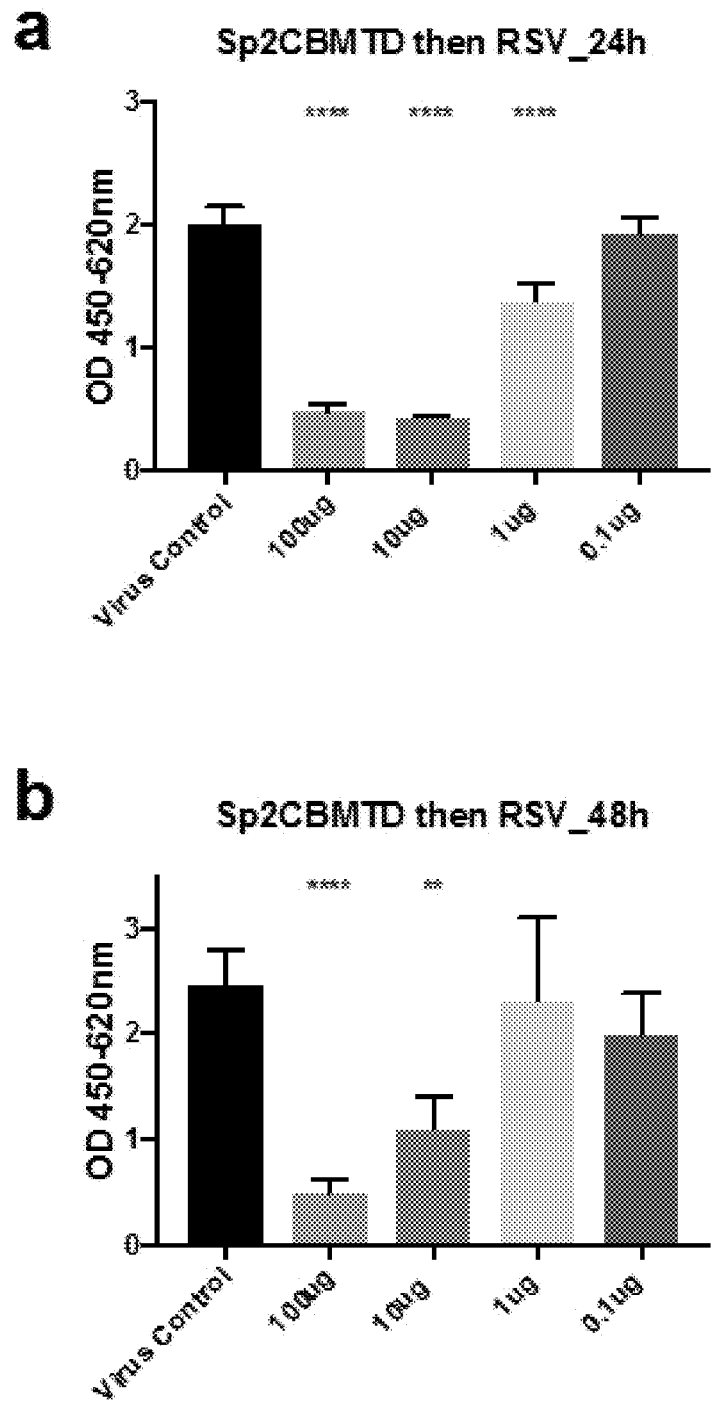
Figure 2 a/b

Figure 2 c/d

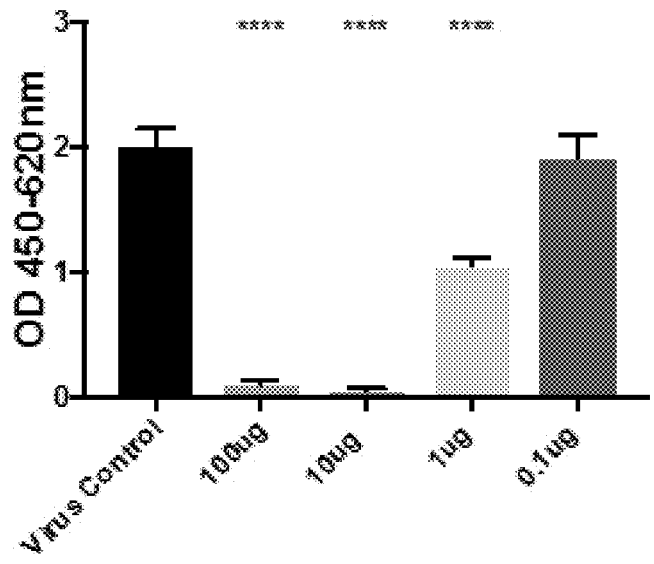
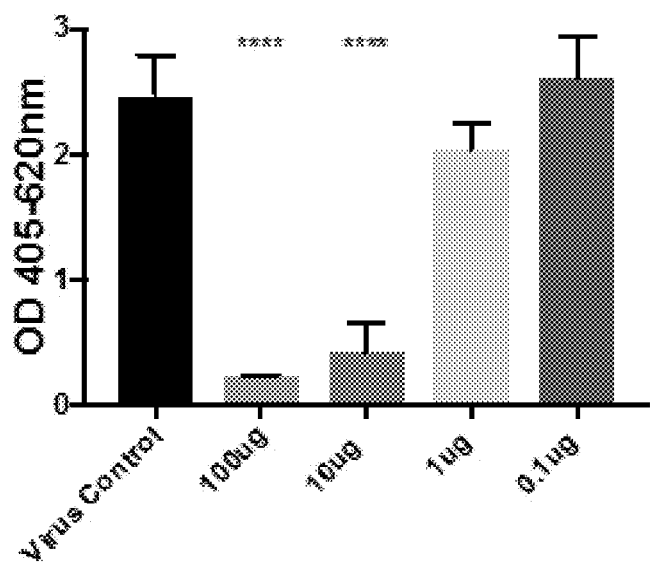
Figure 2 e/f

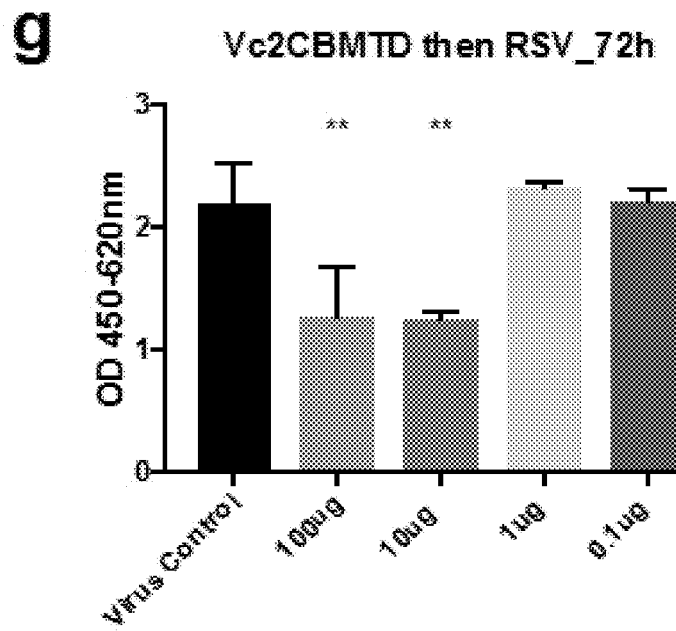
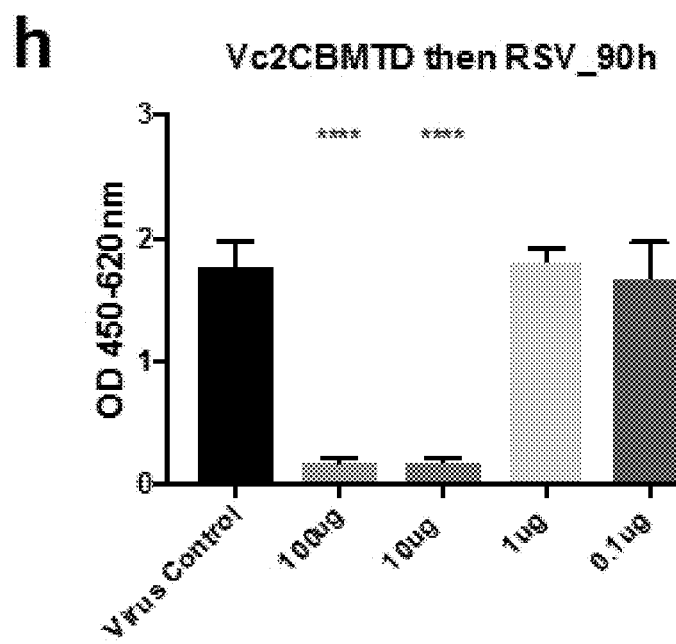
Figure 2 g/h

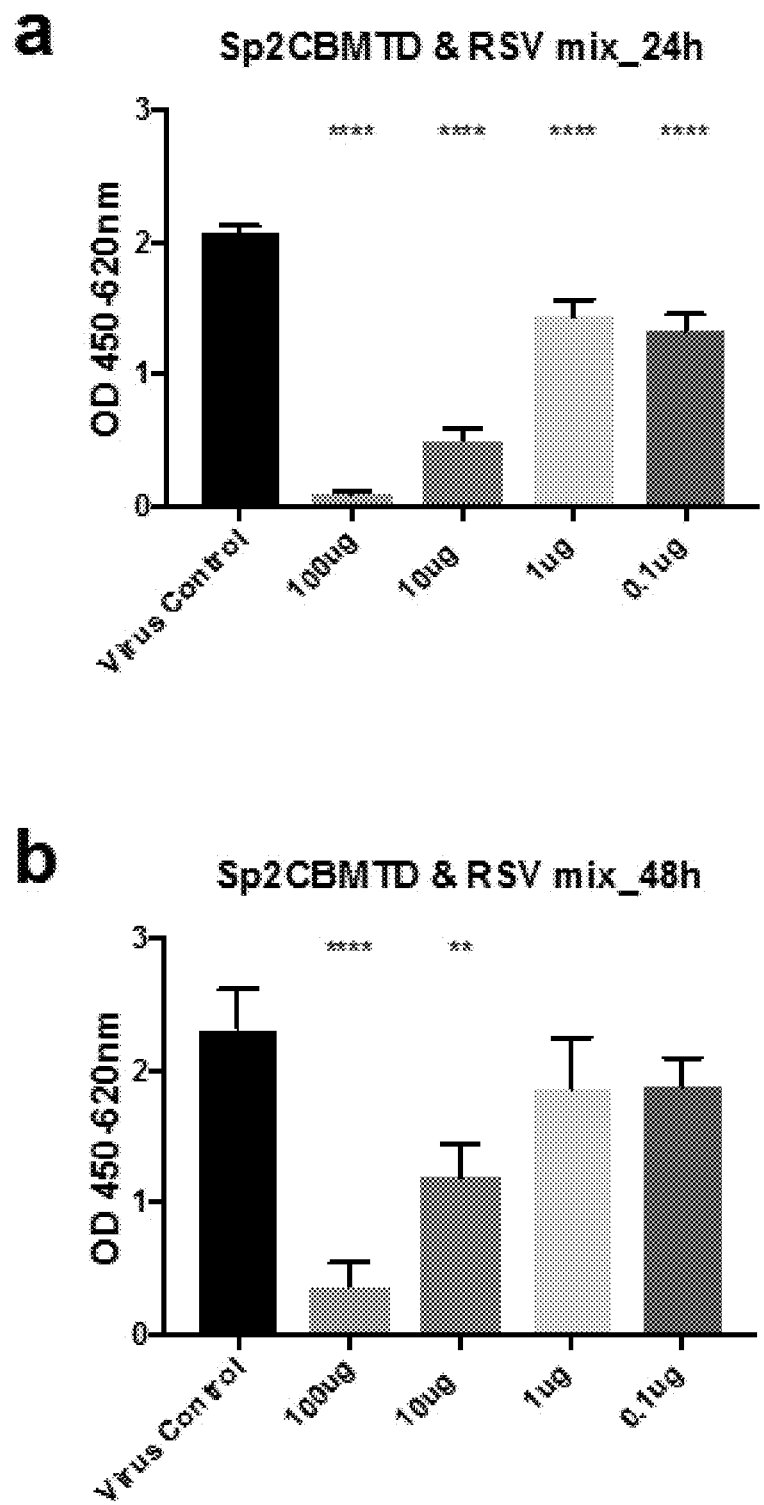
Figure 3 a/b

Figure 3 c/d

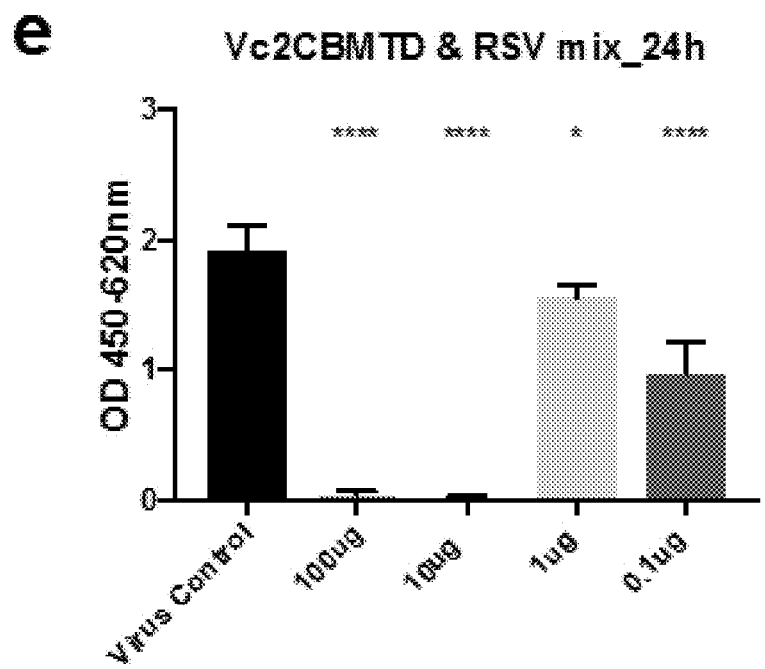
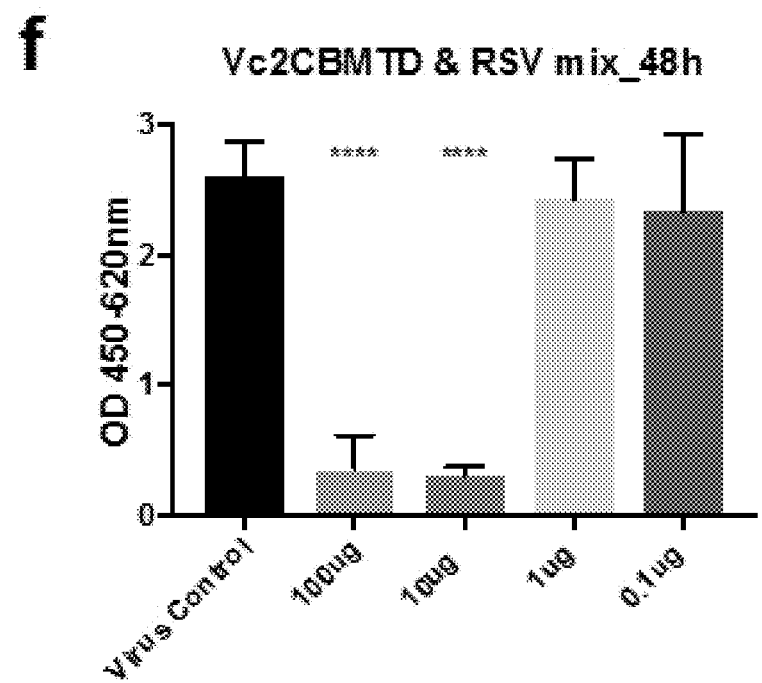
Figure 3 e/f

Figure 3 g/h

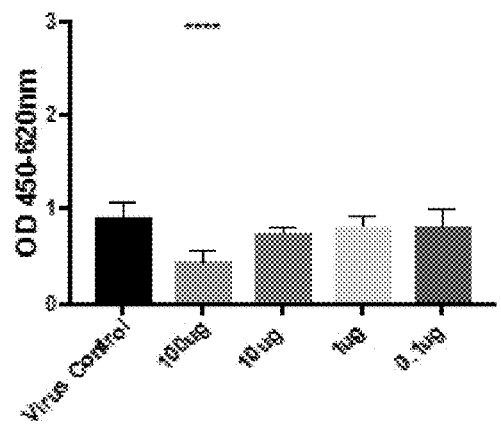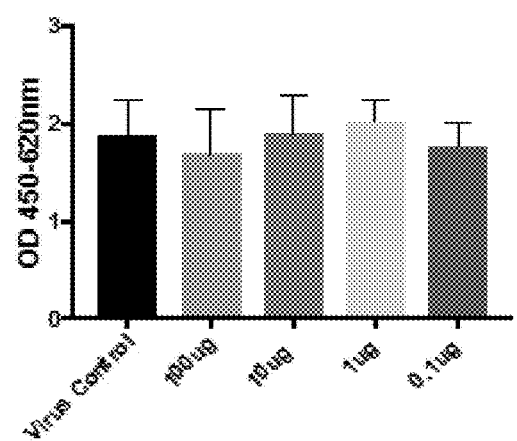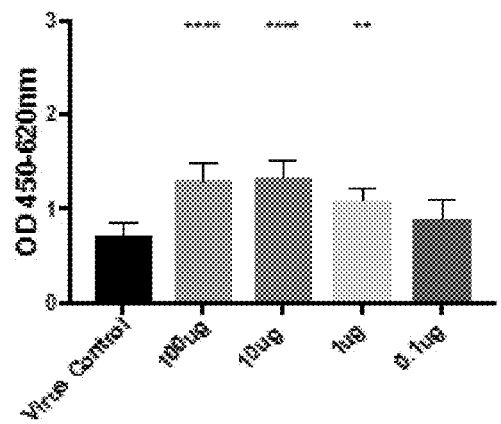
Figure 4 a/b/c

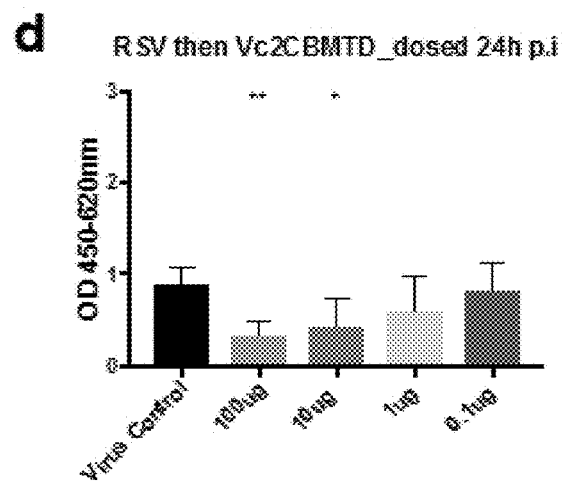
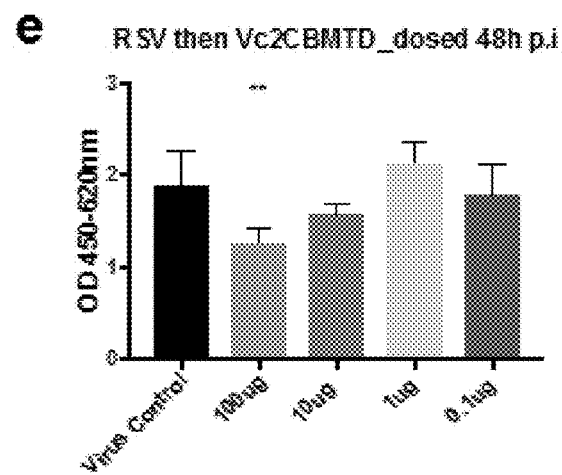
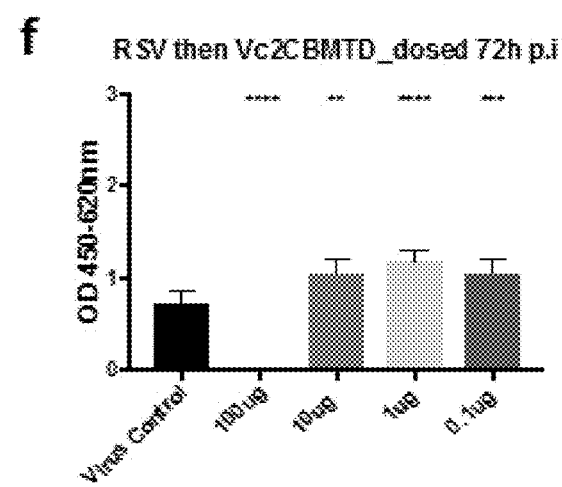
Figure 4 d/e/f

3'-SL treated SP2CBMTD interact with RSV

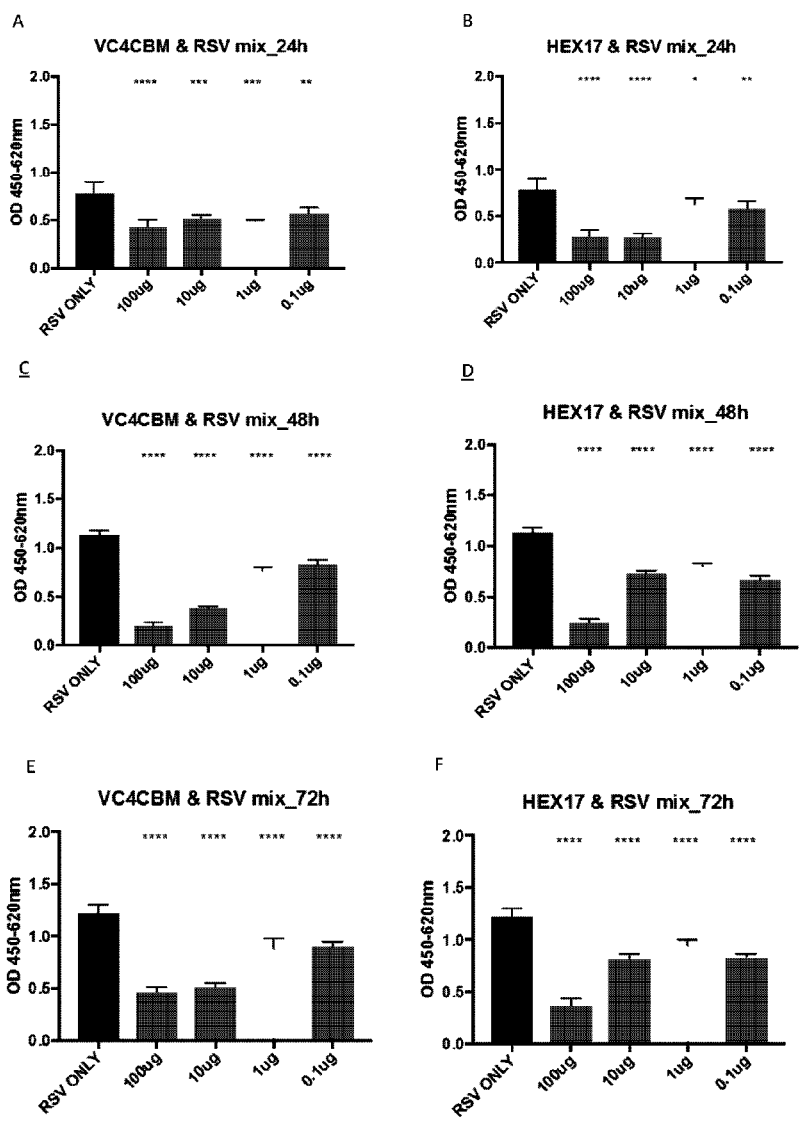
Figure 22A-F

VIRAL TREATMENT

RELATED APPLICATIONS

This application is a 35 U.S.C. § 371 national stage application of PCT Application No. PCT/GB2019/050546, filed on Feb. 27, 2019, which claims priority from United Kingdom Patent Application No. 1803197.1, filed on Feb. 27, 2018, the contents of each of which are incorporated herein by reference in their entireties. The above-referenced PCT International Application was published in the English language as International Publication No. WO 2019/166802A1 on Sep. 6, 2019.

FIELD OF THE INVENTION

The invention provides molecules for use in compositions, medicaments and methods for the treatment or prevention of RSV infections, its symptoms and associated pathologies and potentially infections caused or contributed to by viral pathogens which do not bind or do not primarily bind sialic acid containing receptors during pathogenesis.

BACKGROUND OF THE INVENTION

Respiratory syncytial virus (RSV) is a syncytial virus that causes respiratory tract infections. It causes disease in humans and animals and is a major cause of lower respiratory tract infections and the young and elderly are particularly at risk. Infection with RSV (which includes the form often referred to as human RSV (HRSV)) does induce protective immunity but research shows that the response is not prolonged (or sustained) and multiple instances of infection are not uncommon.

Unlike many other respiratory pathogens, RSV does not bind to sialoglycoconjugates for cell entry and infection[3]. However, due to the ubiquitous and predominant nature of sialic acid as the terminal glycan of respiratory epithelial cell surface glycoconjugates, it would be advantageous if sialic acid binding molecules could be exploited as the basis of treatments for pathogens such as RSV.

SUMMARY OF THE INVENTION

The present disclosure is based on the finding that molecules with affinity for (or an ability to bind to) sialic acid (and in particular sialoglycoconjugates) on cell surfaces (these including sialic acid containing glycoproteins and cell surface sialic acid receptors), find utility in the treatment and/or prevention of symptoms, infections, diseases and/or conditions associated with respiratory syncytial virus (RSV).

The present disclosure provides a sialic acid binding molecule for use in the treatment and/or prevention of symptoms, infections, diseases and/or conditions associated with respiratory syncytial virus (RSV).

Further provided is the use of a sialic acid binding molecule in the manufacture of a medicament for use in the treatment and/or prevention of symptoms, infections, diseases and/or conditions associated with RSV.

The disclosure also provides a method of treating or preventing a RSV symptom, disease, infection or condition, said method comprising administering a subject in need thereof a therapeutically effective amount of a sialic acid binding molecule.

The disclosure also provides sialic acid binding molecules and medicaments and methods comprising sialic acid binding molecules, for use in methods of treating or preventing a symptom, disease and/or condition associated with a RSV infection.

Throughout this specification, the terms "comprise", "comprising" and/or "comprises" is/are used to denote aspects and embodiments of this invention that "comprise" a particular feature or features. It should be understood that this/these terms may also encompass aspects and/or embodiments which "consist essentially of" or "consist of" the relevant feature or features.

RSV is a medium-sized (120-200 nm) enveloped virus containing a lipoprotein coat and a linear negative-sense RNA genome. The genome encodes the F, G, and SH lipoproteins. The F (fusion) and G (attachment) lipoproteins (or glycoproteins) target the host cell membrane and control the initial phases of infection. They are also highly conserved among RSV isolates. Specifically, the G protein targets the ciliated cells of the airways, and the F protein causes the virion membrane to fuse with a target cell membrane. Based on the reactivity of the virus with monoclonal antibodies against the attachment (G) and fusion (F) glycoproteins, RSV is divided into two antigenic subgroups, A and B. As used herein, the term "RSV" includes all strains, forms and antigenic variants of RSV—including all forms, strains and variants of human (H) or animal RSV.

RSV is not a pathogen which binds to or associates with sialic acid during pathogenesis; thus RSV does not bind host cell sialic acid (or cell surface sialoglycoconjugates). Accordingly, the finding that sialic acid binding molecules (such as, for example, CBM40 molecules (and others defined below)) have a utility in the treatment of viral pathogens which do not exploit cell surface sialic acid (sialoglycoconjugates) during pathogenesis (or pathogens in which sialic acid binding is not a primary means by which the pathogens binds to, colonises or enters/infects a cell), is wholly unexpected.

For prior art disclosures where sialic acid binding molecules have been used as agents capable of blocking the binding of pathogens to cell surface sialic acid/sialoglycoconjugates, the utility of the sialic acid binding molecule is rooted in the fact that both the sialic acid binding molecule and the pathogen bind sialic acid; this is not the case with RSV. Because RSV does not bind sialic acid, one of skill would not appreciate that a sialic acid binding molecule could be used to block RSV entry into a cell.

Without wishing to be bound by theory, it is suggested that when bound to cell surface sialic acid/sialoglycoconjugates, sialic acid binding molecules prevent the G and/or F RSV proteins from accessing their targets on the host cell. This, in turn, prevents the RSV from colonising and infecting the cell. Further, data presented below (see in particular the data presented in Example 6) shows that the RSV viral surface comprises glycoproteins which terminate with sialic acid; as such, it is suggested that sialic acid binding molecules are able to bind to these glycoproteins (via the sialic acid component) and further inhibit binding between the RSV and the host cell.

While it may have been established that sialic acid binding proteins can be used to prime or modulate the immune system, and that a primed or modulated immune response may impact on the pathology of a whole host of different pathogens (including those that do not bind or. which do not primarily bind sialic acid during pathogenesis), one of skill would still not have been led to the finding that molecules with an affinity for sialic acid (for example. CBMs such as CBM40 type molecules) can be used to physically block, prevent or neutralise RSV infection.

The observation that sialic acid binding molecules can nevertheless be used to neutralise or block a RSV infection extends this disclosure to the provision of sialic acid binding molecules for use in neutralising or blocking of a RSV infection. Such uses may be applied to in vitro or in vivo methods.

The disclosure further provides the use of a sialic acid binding molecule for the manufacture of medicaments for neutralising or blocking a RSV infection.

The disclosure also relates to a method of neutralising or blocking a RSV infection, said method comprising administering a therapeutically effective amount of a sialic acid binding molecule to a subject in need thereof.

Alternatively, the disclosure provides methods that may be used to render cells non-permissive to RSV (the term "non-permissive" meaning a cell which resists viral attachment or colonisation and/or subsequent infection and viral replication). Such methods (which methods may be in vitro or in vivo methods) may comprise contacting or incubating cells susceptible or vulnerable to RSV infection with a sialic acid binding molecule described herein. The step of contacting or incubating may comprise contacting or incubating a cell with a sialic acid binding molecule prior to contact with RSV. Additionally or alternatively, the step of contacting or incubating a cell with a sialic acid binding molecule may be extended so that the sialic acid binding molecule is contacted with the cell at the same time as the cell is in contact with RSV.

Without wishing to be bound by theory, during the period of incubation, sialic acid containing cell surface receptors will be bound by the sialic acid binding molecule and although RSV does not itself bind sialic acid moieties (sialoglycoconjugates) on the cell surface, it has surprisingly been found that binding between sialic acid binding molecules and cell surface sialic acid containing receptors/sialoglycoconjugates, inhibits or prevents RSV cell binding. This, in turn, prevents RSV cell infection and intracellular RSV replication.

The findings reported in this disclosure have important implications for the formulation and administration of molecules with sialic acid binding affinity and for the subsequent use of these formulations in the treatment and/or prevention of RSV infections. For example, the finding that sialic acid binding molecules (for example, CBMs and/or CBM40 type molecules) can be used to prevent (or neutralise) RSV infection allows for the use of sialic acid binding molecules as formulations suitable for mucosal administration.

Sialic acid binding molecule containing formulations for mucosal administration may be used to (i) prevent RSV binding to host cells; and/or
(ii) block or neutralise RSV.

As stated, the term "block" or "neutralise" refers to the blocking or neutralising effect of the sialic acid binding molecule which binds to host cell sialic acid containing receptors/sialoglycoconjugates and which has now (surprisingly) been found to block RSV cell binding (and subsequent infection).

Accordingly, the disclosure provides a composition for mucosal administration, said composition comprising a sialic acid binding molecule for use in the treatment and/or prevention of diseases and/or conditions associated with RSV.

It should be noted that the term "mucosal administration" embraces compositions that have been formulated for administration to any mucosal surface, including, for example, respiratory surfaces and the like. The term also embraces compositions formulated for administration by inhalation. Compositions suitable (or formulated) for mucosal administration may include compositions, which are intended to be administered intranasally.

Thus a composition for mucosal administration may be formulated with excipients, diluents and/or buffers which are suitable for use in any type of mucosal administration.

Compositions for mucosal (for example intranasal) administration may comprise solutions of the sialic acid binding molecule(s) to be administered and/or particles (comprising the same) for aerosol dispersion or dispensed in drinking water. When dispensed such compositions should desirably have a particle diameter in the range 10 to 200 microns to enable retention in, for example, the nasal cavity; this may be achieved by, as appropriate, use of a powder of a suitable particle size or choice of an appropriate valve. Other suitable compositions include coarse powders having a particle diameter in the range 20 to 500 microns, for administration by rapid inhalation through the nasal passage from a container held close up to the nose, and nasal drops comprising 0.2 to 5% w/v of an active compound in aqueous or oily solution or suspension. A composition for mucosal administration may be provided in the form of a liquid spray.

In one embodiment, the disclosure may not relate to the treatment and/or prevention of RSV by the priming or modulation of an immune response.

The disclosure may further provide sialic acid binding molecules for prophylactic use. Specifically, the sialic acid molecules described herein may be used prophylactically in order to prevent a RSV infection.

A method of prophylaxis or of preventing a RSV infection may comprise administering a subject in need thereof a composition of this disclosure. As stated, a composition of this disclosure may comprise a composition formulated for mucosal (for example intranasal) administration.

As used herein and in any method of preventing a RSV infection, a "subject in need thereof" may be any subject predisposed, susceptible or at risk of developing a RSV infection. The subject may be a neonate, an infant or a child. The subject may be elderly. The subject may be an immunocompromised subject. The subject may have one or more underlying or chronic health problems—in particular, problems affecting the respiratory tract and/or respiration. For example, the subject may suffer from asthma.

Throughout this specification, we use the term "sialic acid binding molecule" this term embraces any useful sialic acid binding molecule. Useful sialic acid binding molecules may take any form and/or belong to any class of molecule or compound (for example they may be proteins, peptides, carbohydrates, antibodies and the like) and the term "sialic acid" embraces all forms of N- or O-substituted neuraminic acid and includes all synthetic, naturally occurring and/or modified forms thereof. Sialic acids may be found as components of cell surface molecules, glycoproteins and glycolipids. Most often, sialic acids are present at the end (terminal regions) of sugar chains connected to cell membranes and/or proteins. For example, some cells of the human upper respiratory tract comprise α-2,6-linked sialic acid receptors and other cells of the upper and lower respiratory tracts comprise α-2,3-linked sialic acid receptors. The sialic acid family encompasses a number (approximately 50) of derivatives that may result from acetylation, glycolylation, lactonisation and methylation at C4, C5, C7, C8 and C9. All such derivatives are to be embraced by the term "sialic acid".

Furthermore, sialic acids are found linked α(2,3) or α(2,6) to Gal and GalNAc or α(2,8) or α(2,9) to another sialic acid. Accordingly, it is important to understand that while the term "sialic acid" is used throughout this specification, it encompasses all derivatives, analogues or variants (either naturally occurring or synthetically generated) thereof as well as monomers, dimers, trimers, oligomers, polymers or concatamers comprising the same.

Thus, a sialic acid binding molecule of this disclosure (and for use as described herein) comprises a moiety which exhibits an affinity for sialic acid—including all forms of sialic acid described above and any form of sialic acid present on the surface of a cell (perhaps as part of a cell surface receptor), for example a mammalian cell. These various forms of sialic acid may be collectively referred to as "sialic acid moieties".

The sialic acid binding molecules of this disclosure exhibit an affinity for sialic acid and as such they may bind/couple to and/or associate with one or more sialic acid moieties. Thus, the term "sialic acid binding molecule" may further encompass any fragment of a whole sialic acid binding molecule which retains an ability to bind to or otherwise couple or associate with a sialic acid moiety.

Sialic acid binding molecules for use may comprise a single sialic acid binding molecule (a monomeric or monovalent molecule, for example) or, alternatively, two or more sialic acid binding molecules—which two or more molecules may be the same or different—a polymeric or multivalent molecule, for example.

A sialic acid binding molecule for use may comprise, consist essentially of or consist of, one or more of the sialic acid binding molecules known as "carbohydrate binding modules" (CBMs). CBMs suitable for use exhibit an affinity for sialic acid. CBMs are classified into families and CBMs classed as members of the family 40 CBMs (CBM40) may be useful. The family 40 CBMs embrace molecules of approximately 200 residues and are often found at the N-terminus of GH33 sialidases. They may also be found inserted in the β-propeller of GH33 sialidases.

The disclosure may embrace the use of molecules, for example, larger molecules, which comprise a sialic acid binding component. As stated, that sialic acid binding component (i.e. the sialic acid binding molecule) may itself comprise (consist of or consist essentially of) a CBM, for example, a CBM40. By way of (non-limiting) example, the molecules (e.g. the sialic acid binding molecules) of this disclosure may not only exhibit an ability to bind sialic acid, but may also have one or more other functions. For example, the molecules may have enzymatic activity. For example, a useful molecule may comprise a CBM (as described herein) and exhibit some sialidase activity.

A useful sialic acid binding molecule may be a fusion protein comprising an enzymatic portion and a sialic acid binding portion—wherein the sialic acid binding portion comprises a CBM as described herein. In such cases, the enzymatic portion may be fused to the sialic acid binding portion. As stated, the enzymatic portion of any useful fusion protein may comprise (or have, or exhibit) sialidase activity.

In one embodiment, the sialic acid binding protein or CBM for the various uses described herein, may not be provided as part of, or comprised within, a molecule (for example a fusion protein) with enzymatic (for example sialidase) activity. Additionally or alternatively, the sialic acid binding molecule may not (i) bind heparin or heparin sulfate and/or (ii) comprise the GAG-binding domain of a protein that binds heparin or heparin sulfate moieties.

As such, the present disclosure provides a CBM or CBM40 for use in the treatment and/or prevention of diseases and/or conditions associated with respiratory syncytial virus (RSV).

Further provided is the use of a CBM or CBM40 in the manufacture of a medicament for use in the treatment and/or prevention of diseases and/or conditions associated with RSV.

The disclosure also provides a method of treating or preventing a RSV infection, said method comprising administering a subject in need thereof a therapeutically effective amount of a CBM or CBM40.

The disclosure also provides sialic acid binding molecules and medicaments and methods comprising a CBM or CBM40 for use in methods of treating or preventing a disease and/or condition associated with a RSV infection.

This disclosure also provides CBM or CBM40 for use in neutralising or blocking a RSV infection.

The disclosure further provides the use of a CBM and/or CBM40 for the manufacture of medicaments for neutralising or blocking a RSV infection.

The disclosure relates to a method of neutralising or blocking a RSV infection, said method comprising administering a therapeutically effective amount of a CBM and/or CBM40 to a subject in need thereof.

Alternatively, the disclosure provides methods that may be used to render cells non-permissive to RSV (the term "non-permissive" meaning a cell which resists viral attachment or colonisation and/or subsequent infection and viral replication). Such methods (which methods may be in vitro or in vivo methods) may comprise contacting or incubating cells susceptible or vulnerable to RSV infection with a CBM and/or CBM40 of this disclosure.

CBM and/or CBM40 containing formulations for mucosal administration may be used to
(i) prevent RSV binding to host cells; and/or
(ii) block or neutralise RSV.

The disclosure provides a composition for mucosal administration, said composition comprising a CBM and/or CBM40 for use in the treatment and/or prevention of diseases and/or conditions associated with RSV. As stated, a composition for mucosal administration may be formulated with excipients, diluents and/or buffers which are suitable for use in any type of mucosal administration.

The disclosure may further provide a CBM or CBM40 for prophylactic use. Specifically, CBM or CBM40 described herein may be used prophylactically in order to prevent a RSV infection.

As stated, a composition of this disclosure may comprise a composition formulated for mucosal (for example, intranasal) administration.

Exemplary carbohydrate binding modules (CBMs) for use may comprise the sialic acid binding domain of *Vibrio cholerae* NanH sialidase (VcCBM: a CBM40) and/or the equivalent (or homologous) domain from *Streptococcus pneumoniae* NanA sialidase (SpCBM: also a CBM40). Of course, similar or homologous sialic acid binding modules present in other organisms are to be encompassed within the scope of the term "CBM".

An exemplary *Vibrio cholerae* NanH sialidase amino acid sequence is deposited under accession umber A5F7A4 and is reproduced below as SEQ ID NO: 1 (781 amino acids).

```
MRFKNVKKTA LMLAMFGMAT SSNAALFDYN ATGDTEFDSP

AKQGWMQDNT NNGSGVLTNA DGMPAWLVQG IGGRAQWTYS

LSTNQHAQAS SFGWRMTTEM KVLSGGMITN YYANGTQRVL

PIISLDSSGN LVVEFEGQTG RTVLATGTAA TEYHKFELVF

LPGSNPSASF YFDGKLIRDN IQPTASKQNM IVWGNGSSNT
```

-continued

```
DGVAAYRDIK FEIQGDVIFR GPDRIPSIVA SSVTPGVVTA

FAEKRVGGGD PGALSNTNDI ITRTSRDGGI TWDTELNLTE

QINVSDEFDF SDPRPIYDPS SNTVLVSYAR WPTDAAQNGD

RIKPWMPNGI FYSVYDVASG NWQAPIDVTD QVKERSFQIA

GWGGSELYRR NTSLNSQQDW QSNAKIRIVD GAANQIQVAD

GSRKYVVTLS IDESGGLVAN LNGVSAPIIL QSEHAKVHSF

HDYELQYSAL NHTTTLFVDG QQITTWAGEV SQENNIQFGN

ADAQIDGRLH VQKIVLTQQG HNLVEFDAFY LAQQTPEVEK

DLEKLGWTKI KTGNTMSLYG NASVNPGPGH GITLTRQQNI

SGSQNGRLIY PAIVLDRFFL NVMSIYSDDG GSNWQTGSTL

PIPFRWKSSS ILETLEPSEA DMVELQNGDL LLTARLDFNQ

IVNGVNYSPR QQFLSKDGGI TWSLLEANNA NVFSNISTGT

VDASITRFEQ SDGSHFLLFT NPQGNPAGTN GRQNLGLWFS

FDEGVTWKGP IQLVNGASAY SDIYQLDSEN AIVIVETDNS

NMRILRMPIT LLKQKLTLSQ N
```

The CBM region of SEQ ID NO: 1 is from amino acid residue 25 to 216—this sequence may be SEQ ID NO: 2.

An exemplary *Streptococcus pneumoniae* NanA sialidase amino acid sequence has been deposited under accession number P62575 and is reproduced below as SEQ ID NO: 3 (1035 amino acids).

```
MSYFRNRDID IERNSMNRSV QERKCRYSIR KLSVGAVSMI

VGAVVFGTSP VLAQEGASEQ PLANETQLSG ESSTLTDTEK

SQPSSETELS GNKQEQERKD KQEEKIPRDY YARDLENVET

VIEKEDVETN ASNGQRVDLS SELDKLKKLE NATVHMEFKP

DAKAPAFYNL FSVSSATKKD EYFTMAVYNN TATLEGRGSD

GKQFYNNYND APLKVKPGQW NSVTFTVEKP TAELPKGRVR

LYVNGVLSRT SLRSGNFIKD MPDVTHVQIG ATKRANNTVW

GSNLQIRNLT VYNRALTPEE VQKRSQLFKR SDLEKKLPEG

AALTEKTDIF ESGRNGKPNK DGIKSYRIPA LLKTDKGTLI

AGADERRLHS SDWGDIGMVI RRSEDNGKTW GDRVTITNLR

DNPKASDPSI GSPVNIDMVL VQDPETKRIF SIYDMFPEGK

GIFGMSSQKE EAYKKIDGKT YQILYREGEK GAYTIRENGT

VYTPDGKATD YRVVVDPVKP AYSDKGDLYK GNQLLGNIYF

TTNKTSPFRI AKDSYLWMSY SDDDGKTWSA PQDITPMVKA

DWMKFLGVGP GTGIVLRNGP HKGRILIPVY TTNNVSHLNG

SQSSRIIYSD DHGKTWHAGE AVNDNRQVDG QKIHSSTMNN

RRAQNTESTV VQLNNGDVKL FMRGLTGDLQ VATSKDGGVT

WEKDIKRYPQ VKDVYVQMSA IHTMHEGKEY IILSNAGGPK

RENGMVHLAR VEENGELTWL KHNPIQKGEF AYNSLQELGN

GEYGILYEHT EKGQNAYTLS FRKFNWDFLS KDLISPTEAK

VKRTREMGKG VIGLEFDSEV LVNKAPTLQL ANGKTARFMT
```

-continued

```
QYDTKTLLFT VDSEDMGQKV TGLAEGAIES MHNLPVSVAG

TKLSNGMNGS EAAVHEVPEY TGPLGTSGEE PAPTVEKPEY

TGPLGTSGEE PAPTVEKPEY TGPLGTAGEE AAPTVEKPEF

TGGVNGTEPA VHEIAEYKGS DSLVTLTTKE DYTYKAPLAQ

QALPETGNKE SDLLASLGLT AFFLGLFTLG KKREQ
```

The CBM region of SEQ ID NO: 3 is from amino acid residue 121 to 305—this sequence may be SEQ ID NO: 4.

Thus, CBMs for use as sialic acid binding molecules in the various aspects and embodiments of this disclosure may comprise a protein or peptide having the sequence of SEQ ID NO: 1, 2, 3 or 4 or a sequence fragment derived therefrom and which encodes a molecule with an ability to bind sialic acid (in other words a sialic acid binding molecule encoding portion of fragment of SEQ ID NOS: 1, 2, 3 or 4).

A useful sialic acid binding molecule may comprise a proteinaceous moiety encoded by the sialic acid binding domain of the nanH gene (encoding sialidase) of *V. cholerae* (as provided by SEQ ID NO: 1) or an equivalent or homologous gene present in another organism (for example the equivalent/homologous nanA sialidase gene of *S. pneumoniae*: see SEQ ID NO: 3).

A sialic acid binding molecule for use may comprise from about residue 1, 5, 10, 15, 25 or 30 (i.e. from 1-30 or from any amino acid residue there between) to about residue 150, 175, 200, 210, 216, 220-781 (to any residue from 150 to 781 including any residue therebetween) of the *V. cholerae* sialidase molecule of SEQ ID NOS: 1 and 2. For example a sialic acid binding molecule for use may comprise a peptide having a sequence corresponding to residue 25 to about residue 216 of SEQ ID NO: 1 above.

A further suitable sialic acid binding molecule may comprise a protein or peptide having the sequence of SEQ ID NO: 3 or 4 or a sialic acid binding fragment thereof. For example, a useful sialic acid binding molecule may comprise a proteinaceous moiety encoded by the sialic acid binding domain of the *Streptococcus pneumoniae* nanA gene (encoding sialidase). For example a sialic acid binding molecule for use may comprise from about residue 80, 90, 100, 110, 120, 121 to 130 (i.e. from any of about residues 80 to 130 including any residue therebetween) to about residue 250, 275, 300, 305, 310, 320-1035 (i.e. to any residue from about 250-1035 including to about any residue therebetween) of the *S. pneumoniae* sialidase molecule of SEQ ID NOS: 3 and 4. For example, a sialic acid binding molecule for use may comprise a peptide having a sequence corresponding to residue 121 to about residue 305 of SEQ ID NO: 3 above.

A sialic acid binding molecule for use may comprise one or more CBMs. For example, suitable sialic acid binding molecules may comprise single CBMs—for example a single VcCBM or a single SpCBM. Alternatively, a sialic acid binding molecule for use may comprise a plurality or multiple (i.e. two or more) CBMs. Sialic acid binding molecules which comprise a plurality of CBMs may be termed "multivalent sialic acid binding molecules" or "multivalent CBMs". A multivalent CBM may, for example, comprise two or more (for example three, four, five or six) VcCBMs or two or more SpCBMs. A multivalent CBM may comprise a mixture of different CBMs, for example one or more VcCBMs with one or more SpCBMs.

The sialic acid binding molecules for use may further comprise an oligomerisation domain. Suitable oligomerisation domains may exhibit an ability to self-associate to form multimer structures, for example trimers. An oligomerisation domain for use may comprise any molecule with the above mentioned oligomerisation properties or any functional fragment thereof. For example, one or more (for example two) sialic acid binding molecules (for example CBMs) may be bound, coupled or fused to an oligomerisation domain—the resulting sialic acid binding molecule:: oligomerisation domain "fusion" may then be used (with one or more other such "fusions") as a molecule for modulating cell growth and/or activity and/or for treating or preventing any of the diseases and/or conditions disclosed herein.

Suitable oligomerisation domains may be derived from, for example, *Pseudomonas aeruginosa* pseudaminidase. An exemplary *Pseudomonas aeruginosa* pseudaminidase sequence amino acid sequence has been deposited under accession number PAO579 and is reproduced below as SEQ ID NO: 5 (438 amino acids).

```
MNTYFDIPHR LVGKALYESY YDHFGQMDIL SDGSLYLIYR

RATEHVGGSD GRVVFSKLEG GIWSAPTIVA QAGGQDFRDV

AGGTMPSGRI VAASTVYETG EVKVYVSDDS GVTWVHKFTL

ARGGADYNFA HGKSFQVGAR YVIPLYAATG VNYELKWLES

SDGGETWGEG STIYSGNTPY NETSYLPVGD GVILAVARVG

SGAGGALRQF ISLDDGGTWT DQGNVTAQNG DSTDILVAPS

LSYIYSEGGT PHVVLLYTNR TTHFCYYRTI LLAKAVAGSS

GWTERVPVYS APAASGYTSQ VVLGGRRILG NLFRETSSTT

SGAYQFEVYL GGVPDFESDW FSVSSNSLYT LSHGLQRSPR

RVVVEFARSS SPSTWNIVMP SYFNDGGHKG SGAQVEVGSL

NIRLGTGAAV WGTGYFGGID NSATTRFATG YYRVRAWI
```

The oligomerisation domain of SEQ ID NO: 5 is from amino acid residue 333 to 438—this sequence may be SEQ ID NO: 6.

Thus an oligomerisation domain for use may comprise from about residue 250, 275, 300, 310, 320, 333, 340 to 350 (i.e. from about residue 250 to about residue 350 including from about any residue therebetween) to about residue 400, 410, 420, 430 or 438 (i.e. to about any residue from about residue 400 residue 438 including to about any residue therebetween) of the *P. aeruginosa* pseudaminidase trimerisation domain (PaTD) provided by SEQ ID NO: 5. For example, a useful sialic acid binding molecule may exploit an oligomerisation domain comprising residues 333 to 438 of SEQ ID NO: 6.

A sialic acid binding molecule for use may comprise one or more of the CBM based molecules presented in FIG. 1. For example, a suitable sialic acid binding molecule may comprise (consist essentially of, or consist of) two or more VcCBMs optionally fused, bound or conjugated to an oligomerisation domain (such as a PaTD or oligomerisation fragment thereof). The sialic acid binding molecule may comprise, consist or consist essentially of two fused (or bound) VcCBMs which are, in turn, fused to an oligomerisation domain (see, for example, molecule Vc2CBMTD shown in FIG. 1).

Other sialic acid binding domains for use may comprise two or more SpCBMs optionally fused, bound or conjugated to an oligomerisation domain (such as a PaTD or an oligomerisation fragment thereof). Sialic acid binding molecules for use may comprise, consist or consist essentially of two fused (or bound) SpCBMs which are in turn fused to an oligomerisation domain (see, for example, molecule Sp2CBMTD shown in FIG. 1).

The terms "sialic acid binding molecule", "CBM" and/or "CBM40" may include modified forms of any of the molecules described herein. Further, the term "modified" embraces molecules which contain one or more mutations relative to a reference sequence.

A "reference sequence" may be any wild type CBM sequence. For example, a reference sequence may comprise, consist essentially of or consist of a wild type family 40 CBM sequence, e.g. the wild type CBM sequences from *Vibrio cholerae* NanH sialidase or *Streptococcus pneumoniae* NanA sialidase (it should be appreciated that similar or homologous CBMs (including CBM40s) present in other organisms are to be encompassed within the scope of the term "CBM" and/or as CBM reference sequences). A reference sequence from which a useful sialic acid binding molecule may be derived (including useful multivalent CBMs as described herein) may comprise any of the specific sequences described herein (for example SEQ ID NO: 1, 2, 3, 4 and 5.

For example, a modified CBM sequence for use may be derived from a specific or particular wild type CBM. A useful modified CBM sequence may comprise a wild type CBM sequence which includes one or more mutations.

The one or more mutation(s) may be functional. The mutations may, for example, alter the overall primary sequence of a CBM for use, but may not (substantially) alter the properties of the CBM—thus, while the sequence of a modified CBM may be different from the wild-type sequence from which it is derived, the overall function of the modified CBM is (substantially) identical to that of the wild-type CBM. Alternatively, the one or more mutation(s) may individually (and/or independently) or collectively (for example synergistically) modulate (improve or suppress/inhibit) one or more of the physiological, biological immunological and/or pharmacological properties characteristic of a wild type CBM (for example the wild type CBM from which the modified CBM is derived). In particular, the one or more mutations may:

(i) alter the immunogenicity (or antigenicity) of the CBM; and/or (ii) alter (for example improve) the efficacy (of the CBM or of any multimeric molecule comprising a modified CBM)' and/or (iii) they may modulate (for example improve) the thermostability of the CBM; and/or (iv) they may modulate (for example improve) the solubility of the CBM; and/or (v) they may modulate (for example improve) the in vivo half-life of the molecule.

A "mutation" may include any alteration to a wild-type CBM molecule. For example, the term "mutation" may embrace, for example:

(i) one or more amino acid substitution(s) (where one or more of the wild type amino acid(s) is/are swapped or changed for another (different) amino acid—the term "substitutions" would include conservative amino acid substitutions); and/or (ii) one or more amino acid deletion(s) (where one or more of the wild type amino acid residue(s) are removed); and/or (iii) one or more amino acid addition(s)/insertion(s) (where additional amino acid residue(s) are added to a wild type (or reference) primary sequence); and/or (iv) one or more amino acid/sequence inversions (usually where two or more consecutive amino acids in a primary sequence are reversed; and/or (v) one or more amino acid/sequence duplications (where an amino acid or a part of the primary amino acid sequence (for example a stretch of 5-10 amino acids) is repeated)

Thus, a useful modified CBM (i.e. a CBM for use in the medical uses and methods described herein) may comprise one or more of the mutations described herein.

By way of non-limiting example, the following represent individual units (referred to as "HEX" units) which may be used to make hexameric sialic acid binding molecules for use in the various embodiments described herein (for example for use in methods of treating or preventing RSV infections etc.). In each case, the HEX unit comprises two modified CBMs (denoted CBM1 and CBM2) with the specific mutations introduced to each CBM being identified in parenthesis. It should be noted that a "----" symbol indicates an amino acid linker (linking one CBM to another or a CBM to an oligomerisation domain). As such, a hexameric sialic acid binding molecule may be made up of several (for example 3) HEX units. In each case, the oligomerisation domain (denoted "TD") conjugates the units together as a trimer. While any given hexamer may comprise identical copies of the units described above (and below under the headings HEX1, HEX2, HEX3, HEX4, HEX5, HEX6 and HEX17), one of skill will appreciate that further options are available. For example, a HEX unit may be made up of two CBMs, each having different mutations (the mutations being one or more selected from the options detailed herein).

(i) HEX1
CBM1 (L170T V239A V246G I286A Y292E)-----CBM2 (L170T V239A V246G I286A Y292E)-----TD (S342D L348D R403K)

(ii) HEX2
CBM1 (V239A V246G I286A Y292E)----CBM2 (V239A V246G I286A Y292E)----TD (S342D R403K)

(iii) HEX3
CBM1 (V239A V246G I286A)-----CBM2 (V239A V246G I286A)-----TD (S342D R403K)

(iv) HEX4
CBM1 (V239A V246G)-----CBM2 (V239A V246G)-----TD (s342D)

(v) HEX5
CBM1 (V239A V246G)-----CBM2 (V239A V246G)-----TD (R403K)

(vi) HEX6
CBM1 (V239A V246G)-----CBM2 (V239A V246G)-----TD (S342D R403K)

(vii) HEX17
CBM1 (V239A V246G A162P)-----CBM2 (V239A V246G A162P)-----TD (S342D R403K)

It will be noted that HEX6 and HEX17 are identical except for the additional A162P mutation. This proline mutation (a substitution for the wild type Alanine at residue 162) has been shown to improve thermostability (the single CBM Tm by 3-4° C.). Further information regarding the use of proline mutations may be derived from Fu 2009, 'Increasing protein stability by improving beta-turns' (DOI 10.1002/prot.22509) which describes the general approach. The proline mutation does not affect (increase or decrease) the predicted immunogenicity of the CBM molecule, is not located near the other mutations, the N- or C-termini or the ligand binding site. Rather unexpectedly, beyond the modest improvement in thermostability, it was noted that the A162P mutation yields hexameric CBMs (i.e. a molecule comprising 3×HEX17 units) exhibiting a marked improvement in in vivo experiments—in particular in comparison to those same experiments conducted using a hexameric molecule comprising 3×Hex6 units. For example, the modified molecules (in particular a molecule comprising 3×HEX17 units) exhibit modulation over pro-inflammatory cytokines, including for example IL-8. Indeed the modulatory effect (specifically an inhibitory effect) on the production of IL-8 by a molecule comprising 3×HEX17 units, was improved over other tested modified molecules.

Relative to the amino acid sequences of Sp2CBMTD (aka "SpOrig" SEQ ID NO: 7) the amino acid sequence of the HEX6 (SEQ ID NO: 8) and HEX 17 (SEQ ID NO: 9) molecules is:

```
SpOrig   GAMVIEKEDVETNASNGQRVDLSSELDKLKKLENATVHMEFKPDAKAPAFYNLFSVSSAT
HEX6     GAMVIEKEDVETNASNGQRVDLSSELDKLKKLENATVHMEFKPDAKAPAFYNLFSVSSAT
Hex17    GAMVIEKEDVETNASNGQRVDLSSELDKLKKLENATVHMEFKPDPKAPAFYNLFSVSSAT SpOrig   KKDEYFTMAVYNNTATLEGRGSDGKQFYNNYNDAPLKVKPGQWNSVTFTVEKPTAELPKG
HEX6     KKDEYFTMAVYNNTATLEGRGSDGKQFYNNYNDAPLKVKPGQWNSVTFTVEKPTAELPKG
Hex17    KKDEYFTMAVYNNTATLEGRGSDGKQFYNNYNDAPLKVKPGQWNSVTFTVEKPTAELPKG SpOrig   RVRLYVNGVLSRTSLRSGNFIKDMPDVTHVQIGATKRANNTVWGSNLQIRNLTVYNRALT
HEX6     RARLYVNGGLSRTSLRSGNFIKDMPDVTHVQIGATKRANNTVWGSNLQIRNLTVYNRALT
Hex17    RARLYVNGGLSRTSLRSGNFIKDMPDVTHVQIGATKRANNTVWGSNLQIRNLTVYNRALT SpOrig   PEEVQKRSGGGSGVIEKEDVETNASNGQRVDLSSELDKLKKLENATVHMEFKPDAKAPAF
HEX6     PEEVQKRSGGGSGVIEKEDVETNASNGQRVDLSSELDKLKKLENATVHMEFKPDAKAPAF
Hex17    PEEVQKRSGGGSGVIEKEDVETNASNGQRVDLSSELDKLKKLENATVHMEFKPDPKAPAF SpOrig   YNLFSVSSATKKDEYFTMAVYNNTATLEGRGSDGKQFYNNYNDAPLKVKPGQWNSVTFTV
HEX6     YNLFSVSSATKKDEYFTMAVYNNTATLEGRGSDGKQFYNNYNDAPLKVKPGQWNSVTFTV
Hex17    YNLFSVSSATKKDEYFTMAVYNNTATLEGRGSDGKQFYNNYNDAPLKVKPGQWNSVTFTV SpOrig   EKPTAELPKGRVRLYVNGVLSRTSLRSGNFIKDMPDVIHVQIGATKRANNTVWGSNLQIR
HEX6     EKPTAELPKGRARLYVNGGLSRTSLRSGNFIKDMPDVTHVQIGATKRANNTVWGSNLQIR
Hex17    EKPTAELPKGRARLYVNGGLSRTSLRSGNFIKDMPDVTHVQIGATKRANNTVWGSNLQIR SpOrig   NLTVYNRALTPEEVQKRSGGALGVPDFESDWFSVSSNSLYTLSHGLQRSPRRVVEFARS
HEX6     NLIVYNRALTPEEVQKRSGGSLGVPDFESDWFDVSSNSLYILSHGLQRSPRRVVEFARS
Hex17    NLTVYNRALTPEEVQKRSGGSLGVPDFESDWFDVSSNSLYTLSHGLQRSPRRVVEFARS
```

```
SpOrig  SSPSTWNIVMPSYFNDGGHKGSGAQVEVGSLNIRLGTGAAVWGTGYFGGIDNSATTRFAT
HEX6    SSPSTWNIVMPSYFNDGGHKGSGAQVEVGSLNIKLGTGAAVWGTGYFGGIDNSATTRFAT
Hex17   SSPSTWNIVMPSYFNDGGHKGSGAQVEVGSLNIKLGTGAAVWGTGYFGGIDNSATTRFAT SpOrig  GYYRVRAWI
HEX6    GYYRVRAWI
Hex17   GYYRVRAWI
```

Thus, the various aspects and embodiments of this disclosure (uses, sialic acid binding molecules for use, methods and medicaments) may exploit sialic acid binding molecules which comprise, consist of or consist essentially of sialic acid binding molecules selected from the group consisting of:
- (i) one or more VcCBM(s);
- (ii) one or more SpCBM(s);
- (iii) one or more modified CBM(s);
- (iv) a HEX17 molecule; and
- (iii) a multivalent CBM.

As such, the present disclosure provides:
Sp2CBM;
HEX17;
Vc2CBM; and/or
Vc4CBM;
for use in the treatment and/or prevention of a RSV infection.

Further provided is the use of Vc2CBM or Vc4CBM in the manufacture of a medicament for use in the treatment and/or prevention of a RSV infection.

The disclosure also provides the use of HEX17 in the manufacture of a medicament for use in the treatment and/or prevention of a RSV infection.

The disclosure also relates to a method of treating or preventing RSV, said method comprising the steps of administering to a subject in need thereof, a therapeutically effective amount of
HEX17;
Sp2CBM;
Vc2CBM; and/or
Vc4CBM.

For the avoidance of doubt, HEX17 is a multivalent modified CBM as described above. Vc2CBM comprises, consists essentially of or consists of two *Vibrio cholerae* NanH sialidase CBM units linked, bound or conjugated together. An exemplary Vc2CBM sequence may comprise, consist essentially of or consist of:

(SEQ ID NO: 10)
GAMALFDYNATGDTEFDSPAKQGWMQDNINNGSGVLINADGMPAWLVQGI
GGRAQWTYSLSTNQHAQASSFGWRMTTEMKVLSGGMITNYYANGTQRVLP
IISLDSSGNLVVEFEGQTGRTVLATGTAATEYHKFELVFLPGSNPSASFY
FDGKLIRDNIQPTASKQNMIVWGNGSSNTDGVAAYRDIKFEIQGDALNGS
MALFDYNATGDTEFDSPAKQGWMQDNINNGSGVLINADGMPAWLVQGIGG
RAQWTYSLSTNQHAQASSFGWRMTTEMKVLSGGMITNYYANGTQRVLPII
SLDSSGNLVVEFEGQTGRTVLATGTAATEYHKFELVFLPGSNPSASFYFD
GKLIRDNIQPTASKQNMIVWGNGSSNTDGVAAYRDIKFEIQGD

Vc4CBM comprises, consists essentially of or consists of four *Vibrio cholerae* NanH sialidase CBM units linked, bound or conjugated together. An exemplary Vc4CBM sequence may comprise, consist essentially of or consist of the following sequence:

(SEQ ID NO: 11)
GAMALFDYNATGDTEFDSPAKQGWMQDNINNGSGVLINADGMPAWLVQGI
GGRAQWTYSLSTNQHAQASSFGWRMTTEMKVLSGGMITNYYANGTQRVLP
IISLDSSGNLVVEFEGQTGRTVLATGTAATEYHKFELVFLPGSNPSASFY
FDGKLIRDNIQPTASKQNMIVWGNGSSNTDGVAAYRDIKFEIQGDALNGS
MALFDYNATGDTEFDSPAKQGWMQDNINNGSGVLINADGMPAWLVQGIGG
RAQWTYSLSTNQHAQASSFGWRMITEMKVLSGGMITNYYANGTQRVLPII
SLDSSGNLVVEFEGQTGRTVLATGTAATEYHKFELVFLPGSNPSASFYFD
GKLIRDNIQPTASKQNMIVWGNGSSNTDGVAAYRDIKFEIQGDLQALGMA
LFDYNATGDTEFDSPAKQGWMQDNINNGSGVLINADGMPAWLVQGIGGRA
QWTYSLSTNQHAQASSFGWRMTTEMKVLSGGMITNYYANGTQRVLPIISL
DSSGNLVVEFEGQTGRTVLATGTAATEYHKFELVFLPGSNPSASFYFDGK
LIRDNIQPTASKQNMIVWGNGSSNTDGVAAYRDIKFEIQGDGGNSGMALF
DYNATGDTEFDSPAKQGWMQDNINNGSGVLINADGMPAWLVQGIGGRAQW
TYSLSTNQHAQASSFGWRMTTEMKVLSGGMITNYYANGTQRVLPIISLDS
SGNLVVEFEGQTGRTVLATGTAATEYHKFELVFLPGSNPSASFYFDGKLI
RDNIQPTASKQNMIVWGNGSSNTDGVAAYRDIKFEIQGD

Sp2CBM comprises, consists essentially of or consists of two *Streptococcus pneumoniae* NanA sialidase units linked, bound or conjugated together. An exemplary Sp2CBM sequence may comprise, consist essentially of, or consist of two copies of the following sequence:

(SEQ ID NO: 12)
GSMVIEKEDVETNASNGQRVDLSSELDKLKKLENATVHMEFKPDAKAPAF
YNLFSVSSATKKDEYFTMAVYNNTATLEGRGSDGKQFYNNYNDAPLKVKP
GQWNSVTFTVEKPTAELPKGRVRLYVNGVLSRTSLRSGNFIKDMPDVTHV
QIGATKRANNTVWGSNLQIRNLTVYNRALTPEEVQKRS

The two copies of the above mentioned sequence may be joined via any one of the peptide linker sequences described herein. For example, a Sp2CBM sequence may comprise, consist essentially of, or consist of GSMVIEKEDVETNASNGQRVDLSSELDKLKKLENATVHMEFKPDAKAPAF
YNLFSVSSATKKDEYFTMAVYNNTATLEGRGSDGKQFYNNYNDAPLKVKP
GQWNSVTFIVEKPTAELPKGRVRLYVNGVLSRTSLRSGNFIKDMPDVTHV -continued

```
QIGATKRANNTVWGSNLQIRNLTVYNRALTPEEVQKRS[xxxxx][xxxx xxxxxx][xxxxxxxxxxxxxxx]GSMVIEKEDVETNASNGQRVDLSSEL

DKLKKLENATVHMEFKPDAKAPAFYNLFSVSSATKKDEYFTMAVYNNTAT

LEGRGSDGKQFYNNYNDAPLKVKPGQWNSVTFTVEKPTAELPKGRVRLYV

NGVLSRTSLRSGNFIKDMPDVTHVQIGATKRANNTVWGSNLQIRNLTVYN

RALTPEEVQKRS
```

Wherein [xxxxx], [xxxxxxxxxx] and [xxxxxxxxxxxxxxx]—represent the choice of linker peptide sequences as outlined below. Both CBM sequences would be joined by one of the 5, 10 or 15 amino acid linker sequences described herein.

Vc2CBM and Vc4CBM may be described as tandem-repeat multivalent proteins based on the Family 40 sialic acid binding domain (CBM) of the nanH gene encoding the sialidase from *V. cholerae*. Sp2CBM may be described as a tandem-repeat multivalent protein based on the family 40 sialic acid binding domain (CBM) of the nanA gene encoding the sialidase from *S. pneumoniae*.

The disclosed molecules (for the uses and methods described herein) may be generated using PCR-based cloning techniques and a suitable method for the generation of multivalent molecules of this type is described in, for example, Connaris et al, 2009 (Enhancing the Receptor Affinity of the Sialic Acid-Binding Domain of *Vibrio cholerae* Sialidase through Multivalency; J. Biol. Chem; Vol. 284(11); pp 7339-7351). For example, multivalent CBM molecules, including the likes of HEX17, Vc2CBM, Vc4CBM and Sp2CBM may be prepared as constructs comprising multiple CBMs linked by amino acid/peptide linkers. Each CBM (for example VcCBM) may be linked to another by, for example, peptides comprising 5, 10 or 15 amino acids. By way of example any one or more of the following peptides may be used to link two or more CBMs to produce a multivalent CBM:

```
(i)   5 amino acid linkers:    ALXGS
                               (SEQ ID NO: 13)
                               LQALG
                               (SEQ ID NO: 14)
                               GGXSG
                               (SEQ ID NO: 15)
                               GGALG
                               (SEQ ID NO: 16)
                               GGGGS
                               (SEQ ID NO: 17)

(ii)  10 amino acid linkers:   ALXGSGGGSG
                               (SEQ ID NO: 18)

LQALGGGGSL
                               (SEQ ID NO: 19)

(iii) 15 amino acid linkers:   ALXGSGGGSGGGGSG
                               (SEQ ID NO: 20)
``` where "X" is any amino acid.

An exemplary Vc4CBM may take the following form:

This schematic shall be referred to hereinafter as General Formula 1.

Thus, a Vc4CBM molecule may conform to General Formula 1 as set out above, wherein Peptide Linkers A, B and/or C are selected from the linker options presented above as (i), (ii) and/or (iii). It should be noted that the term "VcCBM40" embraces not only the complete family 40 CBM derived from *Vibrio cholerae* (NanH sialidase) but also sialic acid binding fragments derived therefrom. Indeed, each of the VcCBM units shown in General Formula 1 may be selected from the group consisting of:

(i) a *Vibrio cholerae* NanH sialidase CBM; and (ii) a *Vibrio cholerae* NanH sialidase CBM sialic acid binding fragment thereof.

Thus, each of the VcCBM units of the molecule shown in General Formula 1 may be the same or different.

Further, it should be noted that the various uses, methods and medicaments described herein may exploit one or more of the sialic acid binding molecules described herein. For example, two or more different sialic acid binding molecules may be administered to a subject together, concurrently or separately.

The present disclosure may provide compositions for use in the various uses, medicaments and methods described herein. As such, any of the sialic acid binding molecule(s) described herein may be formulated for use. For example, a sialic acid binding molecule (or molecules) may be formulated as therapeutic or pharmaceutical compositions. The various compositions may comprise one or more of the sialic acid binding molecules described herein and any given treatment may require the administration (together, concurrently or separately) of one or more of these compositions.

Pharmaceutical compositions according to the present invention, in particular those formulations for mucosal or intranasal administration may be prepared conventionally, comprising substances that are customarily used in pharmaceuticals and as described in, for example, Remington's The Sciences and Practice of Pharmacy, 22nd Edition (Pharmaceutical Press 2012) and/or Handbook of Pharmaceutical Excipients, 7th edition (compiled by Rowe et al, Pharmaceutical Press, 2012)—the entire content of all of these documents and references being incorporated by reference.

Any suitable amount of a sialic acid binding molecule (for example, any of the CBM type molecules described herein, including the CBM40s) may be used. For example, whether a composition comprising a sialic acid binding molecule (for example a CBM such as Sp2CBM or Vc2CBMTD) is to be administered intravenously or mucosally (for example, intranasally) the dose of sialic acid binding molecule may comprise anywhere between about 0.1 µg and about 1000 µg. For example, a dose of about (for example +/−0.5 µg) 0.1 µg, 0.5 µg, 1 µg, 5 µg, 10 µg, 11 µg, 12 µg, 13 µg, 14 µg, 15 µg, 20 µg, 30 µg, 40 µg, 50 µg, 100 µg, 200 µg, 300 µg, 400 µg, 500 µg, 600 µg, 700 µg, 800 µg, 900 µg or 950 µg of the sialic acid binding molecule may be used. These amounts may be provided in any suitable volume of excipient, diluent or buffer. For example, the amount of sialic acid binding molecule may be provided in anywhere between about 1 µl to about 5 ml of excipient, diluent or buffer. For example, the required amount of sialic acid binding molecule may be combined (or formulated) with about 5 µl, 10 µl, 15 µl, 20 µl, 25 µl, 30 µl, 35 µl, 40 µl, 45 µl, 50 µl, 55 µl, 60 µl, 65 µl, 70 µl, 75 µl, 80 µl, 85 μl, 90 μl, 95 μl, 100 μl, 200 μl, 300 μl, 400 μl, 500 μl, 600 μl, 700 μl, 800 μl, 900 μl, 1 ml, 2 ml, 3 ml or 4 ml. Concentrations of 0.1-1 mg (sialic acid binding protein) per ml (excipient, diluent or buffer) may be most useful.

DETAILED DESCRIPTION

Brief Description of the Drawings

The present invention will now be described in detail with reference to the following figures which show:

FIG. 1: Building blocks of the multivalent CBM forms and their affinities for sialic acid. a, VcCBM, residues 25-216 of the *V. cholerae* sialidase (PDB:1w0p) with α-2, 3-sialyllactose drawn as spheres. b, SpCBM, residues 121-305 of *S. pneumoniae* NanA sialidase with α-2,3-sialyllactose (PDB:4c1w). c, TD, the trimerisation domain, residues 333-438, of the *P. aeruginosa* pseudaminidase (PDB:2w38) in rainbow colours; the other two monomers in single colors. d, Multivalent forms: their molecular weights, valencies and binding affinities for α2,3-sialyllactose as determined by surface plasmon resonance (SPR) at 25° C. ($K_D$ values for VcCBM, Vc2CBM and Vc3CBM had been reported previously[7]). Tandem repeat CBMs, and oligomeric CBMs fused to TD are linked by a 5-amino linker.

Figure 2:
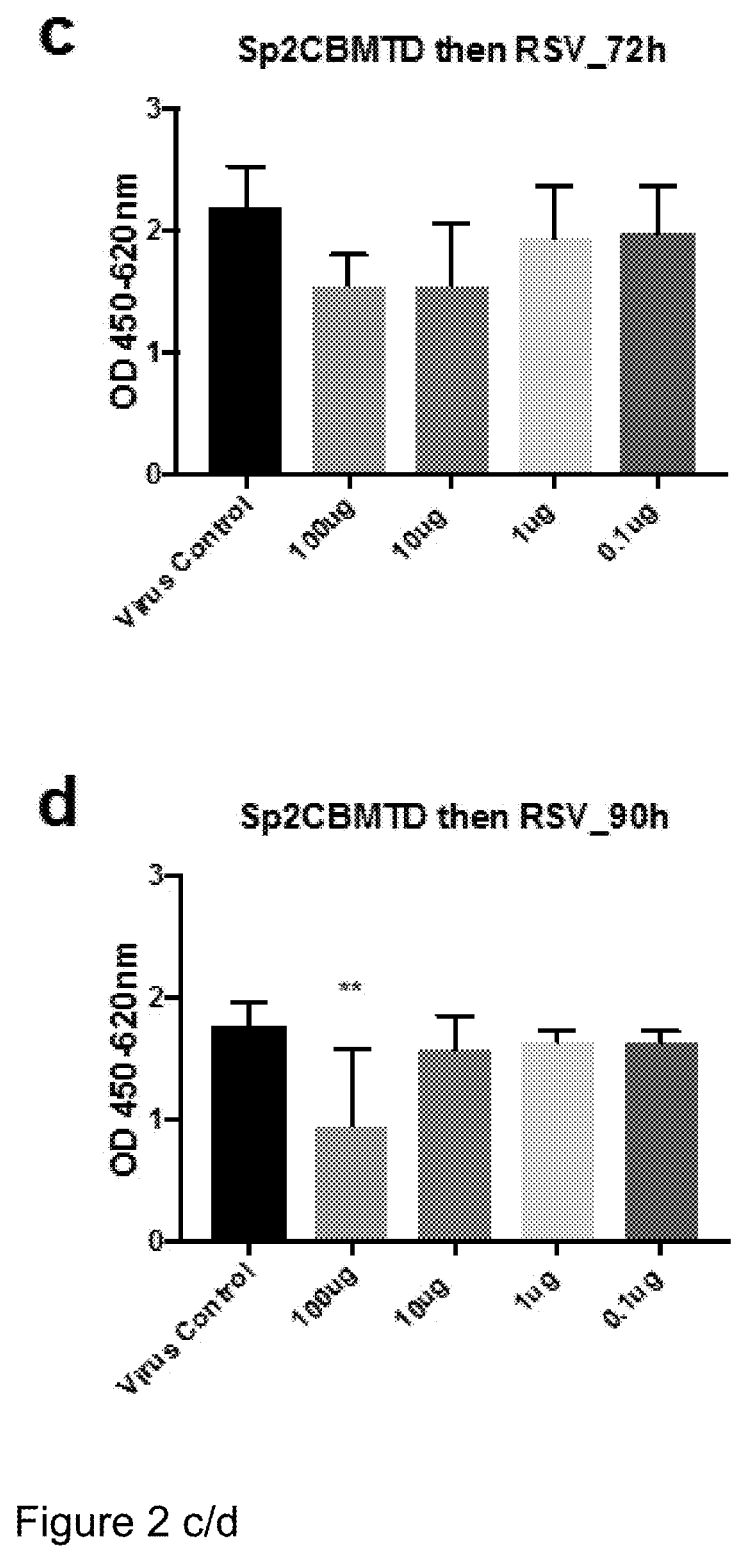

FIG. 2. Prophylactic effect of mCBM40s in a RSV-infected mammalian cell line. Hep2:NPro cells were incubated with varying amounts (0.1-100 μg/well) of either Sp2CBMTD or Vc2CBMTD for 1 hour before the addition of RSV ($1.5\times10^3$ PFU per well). Absorbance readings of infected cells taken at 24 h, 48 h, 72 h and 90 h post infection for Sp2CBMTD (a-d), and for Vc2CBMTD (e-h) treated cells compared to untreated, infected cells, are shown. Bars indicate the mean absorbance change±SD from six replicates. All values are presented as mean±SD, with statistical results presented as: * $p<0.05$,  $p<0.01$, *$p<0.001$, and ****$p<0.0001$.

Figure 3:
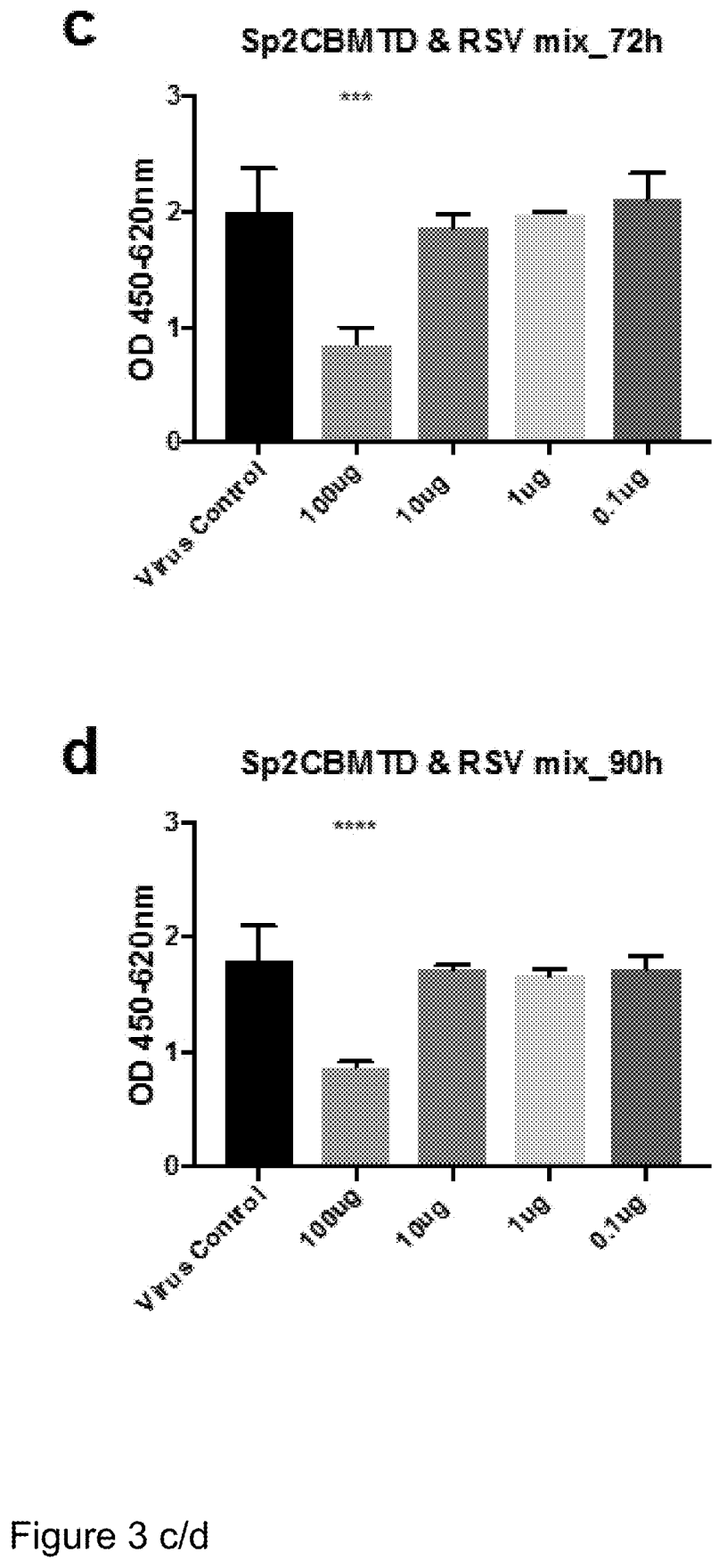
Figure 3:
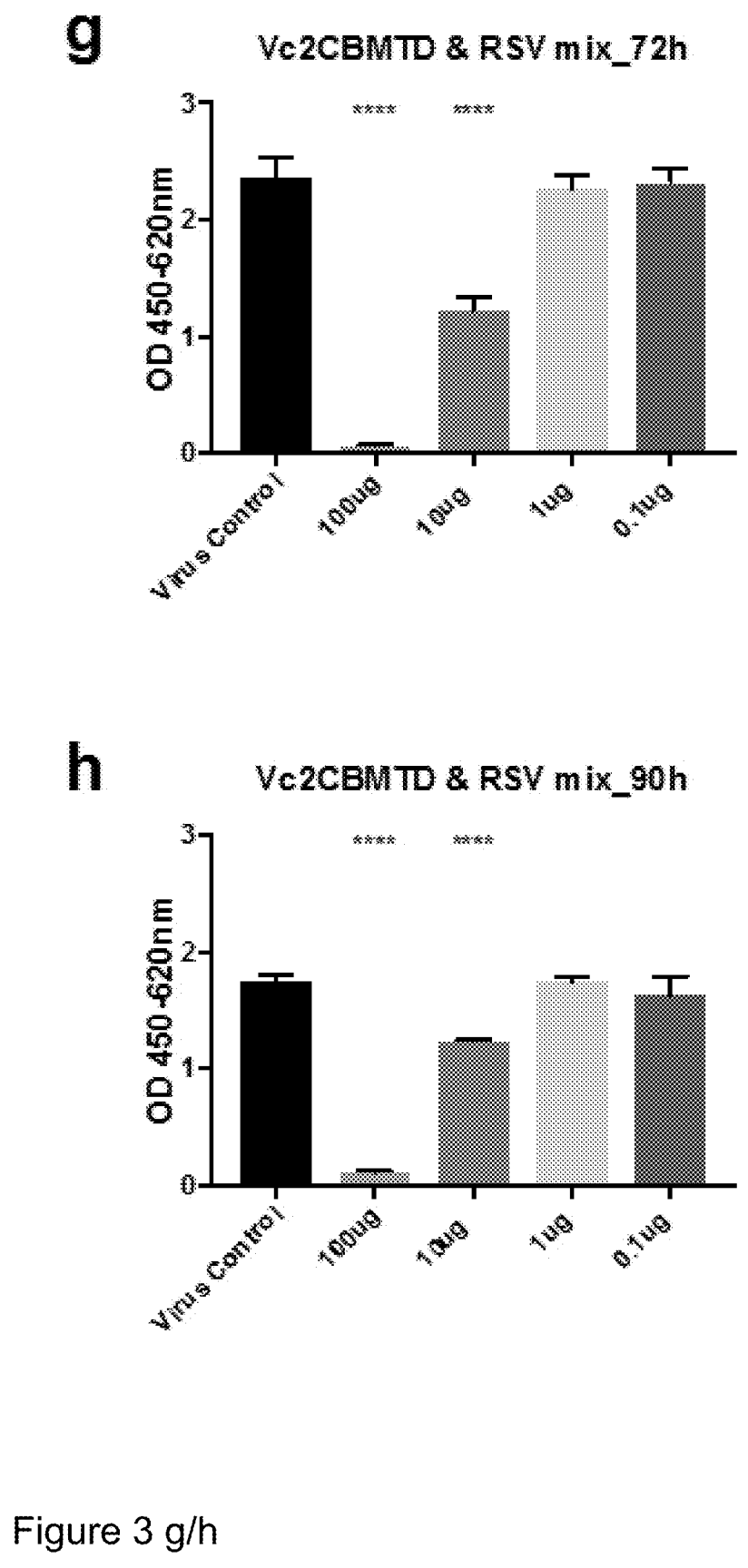

FIG. 3. Effect of mCBM40s in a RSV-infected mammalian cell line. Hep2:NPro cells were incubated with varying amounts (0.1-100 μg/well) of either Sp2CBMTD or Vc2CBMTD with RSV ($1.5\times10^3$ PFU per well) prior to adding to cells. Absorbance readings of infected cells taken at 24 h, 48 h, 72 h and 90 h post infection for Sp2CBMTD (a-d), and for Vc2CBMTD (e-h) treated cells compared to untreated, infected cells, are shown. Bars indicate the mean absorbance change±SD from six replicates. All values are presented as mean±SD, with statistical results presented as: * $p<0.05$,  $p<0.01$, *$p<0.001$, and ****$p<0.0001$.

FIG. 4. Therapeutic effect of mCBM40s in a RSV-infected mammalian cell line. Hep2:NPro cells were incubated with RSV ($1.5\times10^3$ PFU per well) prior to adding varying amounts (0.1-100 μg/well) of either Sp2CBMTD or Vc2CBMTD at 24 h, 48 h or 72 h post infection. Absorbance readings of infected cells were taken at 90 h post infection for Sp2CBMTD (a-c), and for Vc2CBMTD (d-f) treated cells compared to untreated, infected cells, are shown. Bars indicate the mean absorbance change±SD from six replicates. All values are presented as mean±SD, with statistical results presented as: * $p<0.05$,  $p<0.01$, *$p<0.001$, and ****$p<0.0001$.

FIG. 5: ProPred predictions of antigenic peptides. A. SpCBM sequence (SEQ ID NO: 4). B. PaTD sequence (SEQ ID NO: 6). Predicted binders are coloured blue, with the first residue of each binding region shown in red. Antigenic peptides predicted by Nordic Biopharma (green bars) and ProImmune (purple bars) are shown under the sequences.

FIG. 6: Expression test of wild type and mutated domains. Lane 1, M12 standard; Lane 2, WTSpCBM; Lanes 3-11, Im15-Im23; Lanes 12-15, Im24-Im27; Lane 16, WT PaTD. A) Whole cell extracts, B) Soluble extracts.

FIG. 7: Position of peptide 167-181 in the SpCBM structure

FIG. 8: Expression and Ni-NTA pull-down of variants Im28 to Im34

FIG. 9: Sites of the HEX17 mutations on the hexamer structure. The quaternary structure of HEX17 was modelled by assembling the crystal structures of the individual SpCBM (pdb code 4c1x) and PaTD (pdb code 2w38) into the hexamer (i.e. 6 copies of SpCBM and 3 copies of PaTD per molecule). The positions of the bound ligand (α2,3-sialyllactose) are shown in stick form (orange). The positions of the mutations are also shown: Blue, the sites of the A162P mutation; Cyan, the sites of the other two CBM mutations; Magenta, the sites of the TD mutations.

FIG. 10: IL-8 stimulation. A549 cells were stimulated by the addition of 10 μg of biologic (Hex17). Cell supernatant was harvested at 24 or 48 h time-points and the IL-8 content was determined by ELISA. Statistical significance between control and treated cells was determined with one-way ANOVA using Tukey's multiple comparison test.

FIG. 11: Multiplex analysis of inflammatory mediators. A549 cells were stimulated by the addition of 10 μg of biologic (Sp2CBMTD (aka SpOrig), HEX6 or HEX17). Cell supernatant was harvested at 6 h, 24 or 48 h time-points and inflammatory mediators analysed using a Human Cytokine 12-plex Assay. Statistical significance between control and/or WT hexamer and hexamer variants was determined using a one-way ANOVA (Tukey's multiple comparison test).

FIG. 12: Percentage survival of CBM-treated and untreated mice when lethally challenged with influenza strain PR8. CBM2, CBM3 and CBM4 represent HEX17, HEX6 and WT (SpOrig) respectively. Single CBM dosed animals were given 100 μg of CBM one day prior to lethal challenge with PR8; repeat dosed animal were given 2×0.1 μg of CBM at day-3 and day-1 prior to PR8 challenge.

FIG. 13: Clinical scores of CBM-treated and untreated mice during PR8 infection. CBM2, CBM3 and CBM4 represent HEX17, HEX6 and WT (SpOrig) respectively. An ascending clinical score of 1 to 5 indicates no symptoms (1) to lethargy and death (5), respectively.

FIG. 14: Percentage weight loss of CBM-treated and untreated mice during PR8 infection. CBM2, CBM3 and CBM4 represent Hex17, Hex6 and WT (SpOrig) respectively.

FIG. 15: Anti-mCBM antibody analysis of Day 21 lung homogenates and sera tissue from a PR8-challenged mouse study. Statistical significance between WT hexamer and hexamer variants was determined using a one-way ANOVA (Tukey's multiple comparison test).

FIGS. 16A and B: ELISA results to show interaction of Sp2CBMTD and Vc2CBMTD with RSV.

FIG. 17A-E: Assay to show binding of GFP-Sp2CBMTD and Vc2CBMTD with RSV. PBS used in control assays.

Figure 18:
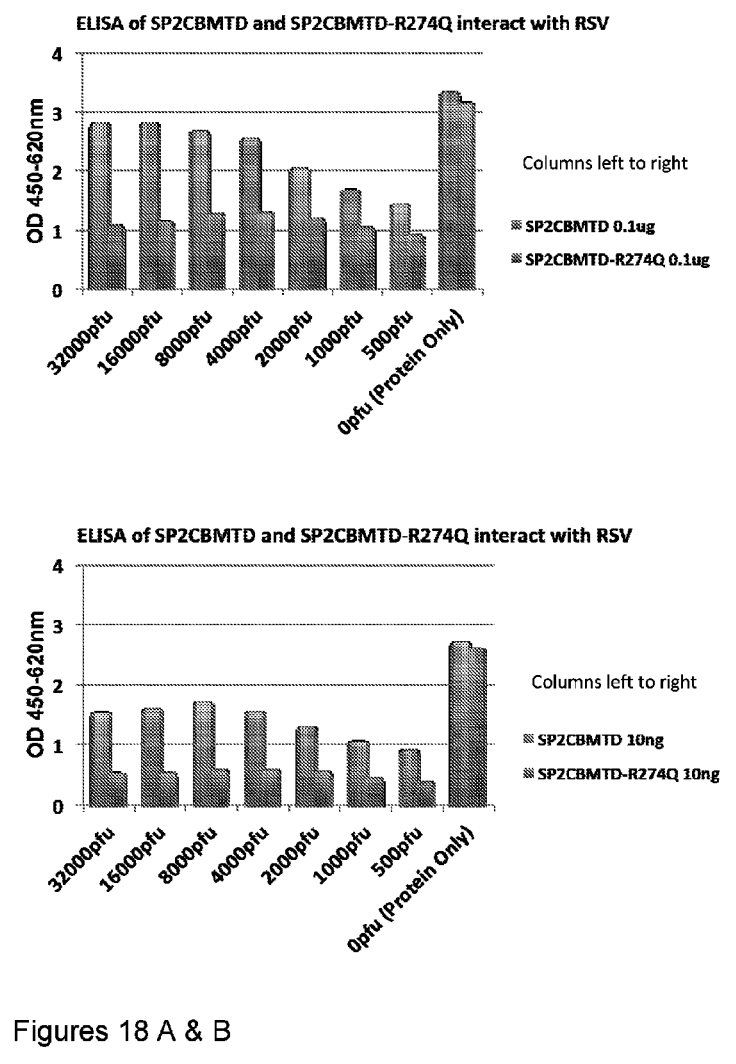

FIGS. 18A and B: ELISA results to show interaction between Sp2CBMTD and Sp2CBMTD-R274Q (at 0.1 μg and 10 ng) with RSV.

Figure 19A:
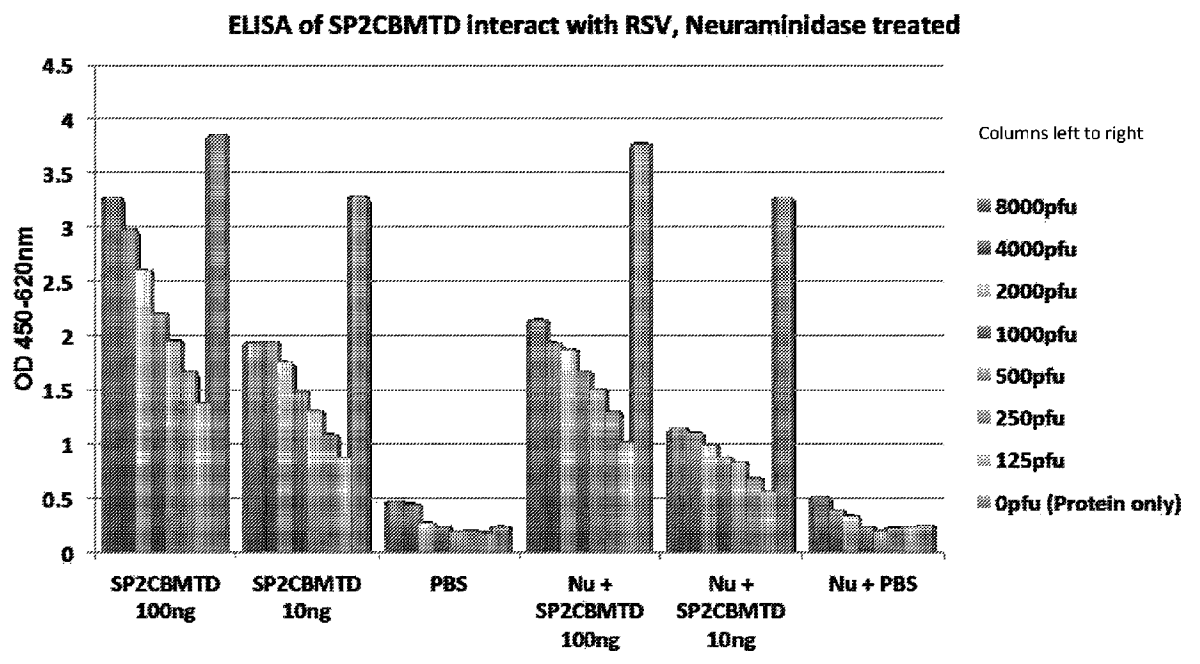
Figure 19B:
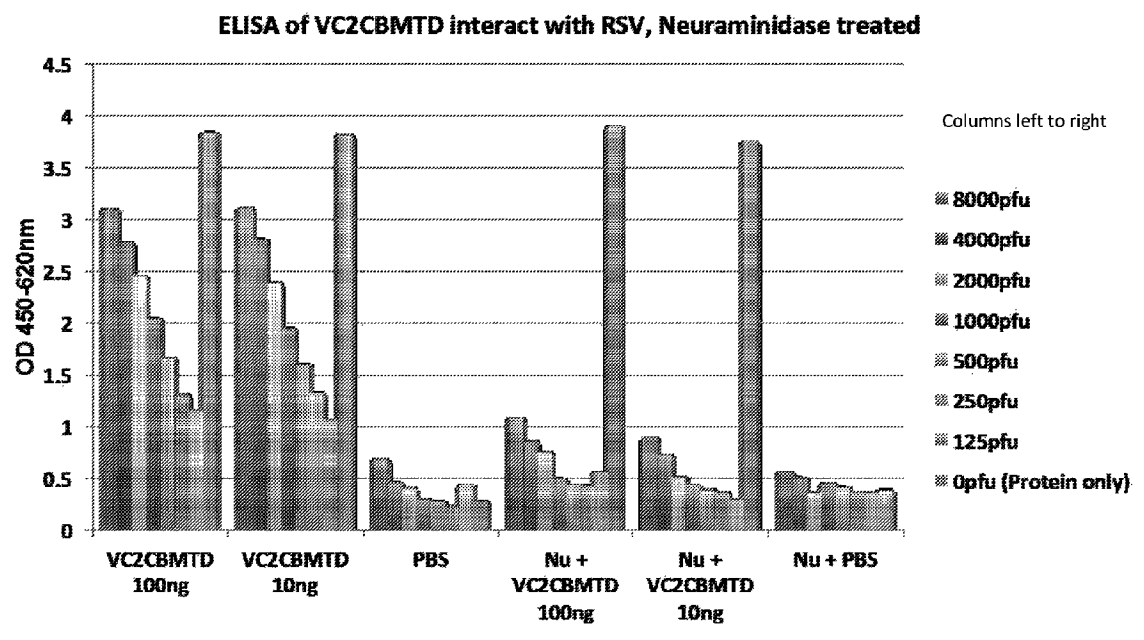

FIGS. 19A and B: ELISA results to show interaction between Sp2CBMTD and Vc2CBMTD with neuraminidase treated RSV.

Figure 20A:
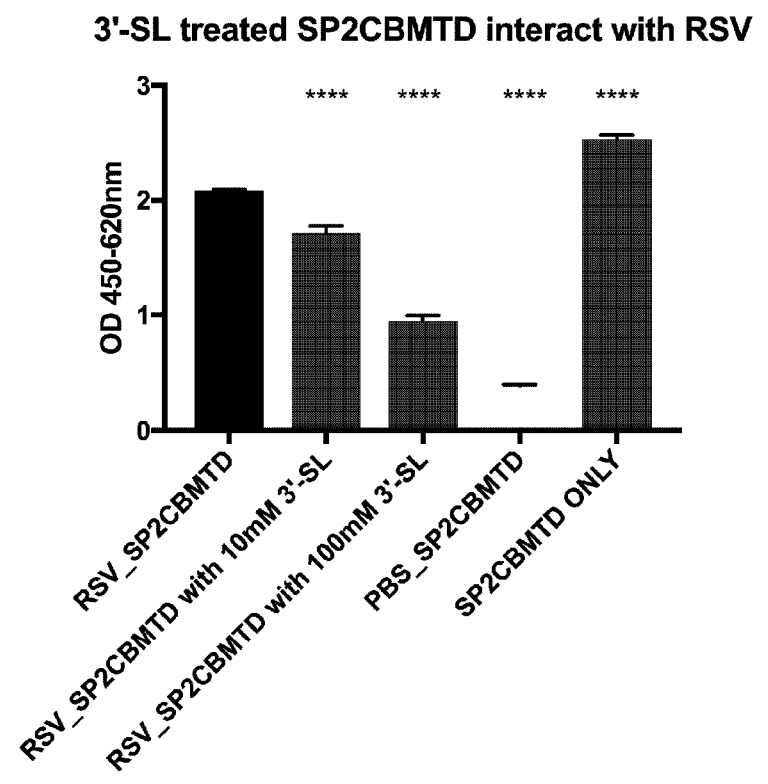
Figure 20B:
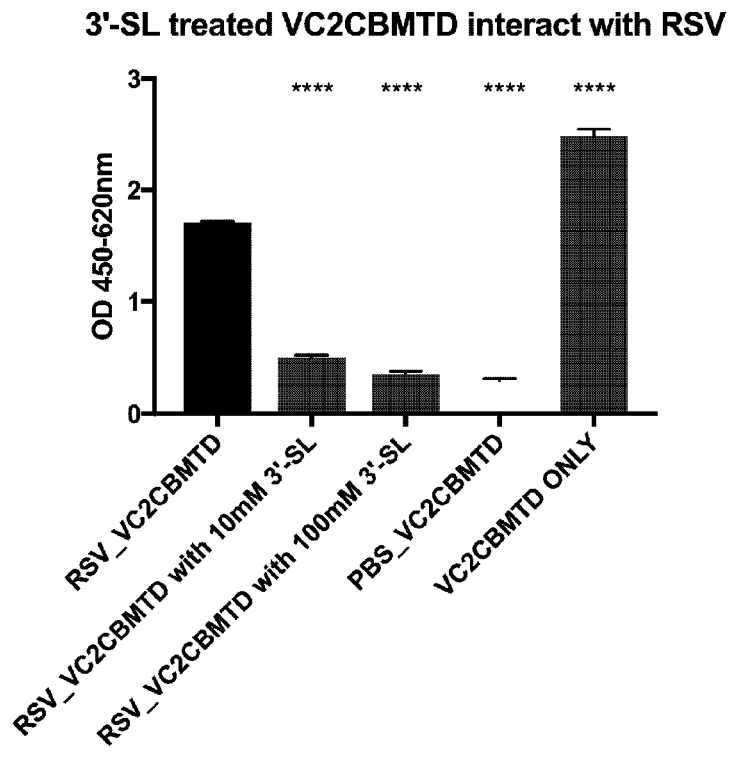
Figures 21A, 21B:
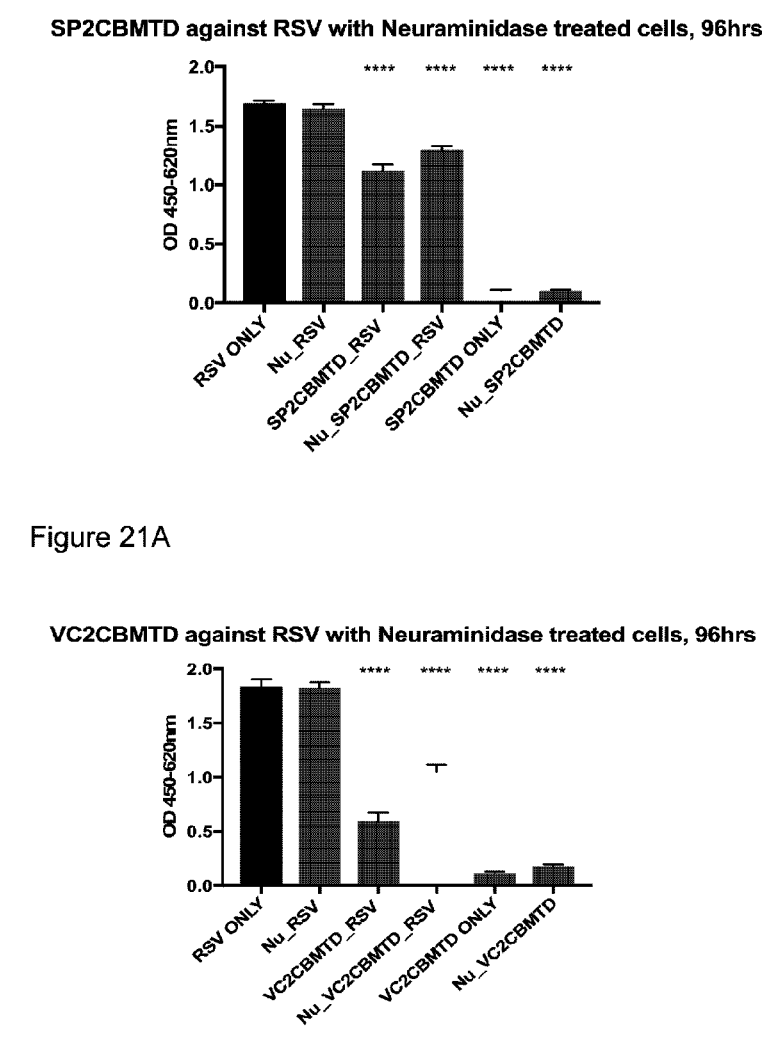

FIGS. 20A and B: data to show the interaction between 3'-SL treated Sp2CBMTD/Vc2CBMTD and RSV FIGS. 21A and B: Data to show that mammalian cell (HEp2:NPro cell) protection by CBMs (Sp2CBMTD and Vc2CBMTD) from RSV is decreased after cells are treated using neuraminidase.

FIG. 22 (panels A-F): Effect of mCBM40s in a RSV-infected mammalian cell line. Hep2:NPro cells were incubated with varying amounts (0.1-100 µg/well) of either Vc4CBM or HEX17 with RSV ($1.5 \times 10^3$ PFU per well) prior to adding to cells. Absorbance readings of infected cells taken at 24 h, 48 h, and 72 h post infection for Vc4CBM (A, C and E), and for HEX17 (B, D and F) treated cells compared to untreated, infected cells, are shown. Bars indicate the mean absorbance change±SD from six replicates. All values are presented as mean±SD, with statistical results presented as: * $p<0.05$,  $p<0.01$, *$p<0.001$, and ****$p<0.0001$.

Figure 23:
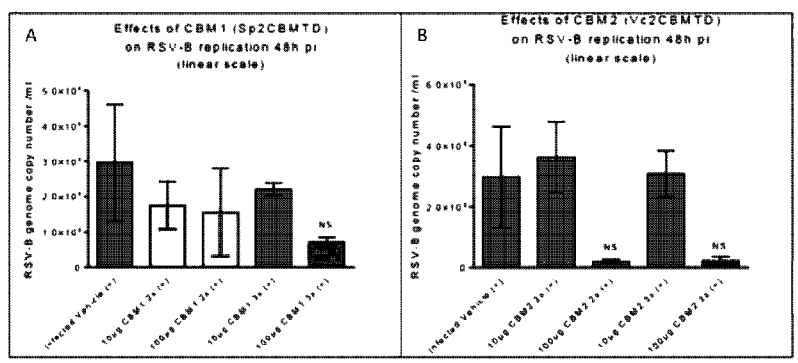

FIGS. 23A and B: RSV-B viral genome copy number quantification of CBM-treated infected MucilAir inserts at 48 h p.i. compared to virus-only infected cells. A) Sp2CBMTD, B) Vc2CBMTD.

METHODS AND RESULTS

Example 1

CBM40 proteins, Sp2CBMTD, Vc2CBMTD and Vc4CBM endotoxin-free) were prepared as described in Connaris et al (2014)[1]. Hex17 was prepared as described above. The mammalian cell line HEp2:NPro (a cell line designed to constitutively overexpress BVDV N-terminal protease fragment, Npro that only responds to IFN but not produce IFN) was purchased from ATCC[4]. Cells were maintained in T75 flasks in DMEM/10% FBS (with 1% Penicillin/Streptomycin), and incubated at 37° C. and 5% $CO_2$. RSV-A2 strain was prepared in SF-DMEM to a dilution of $10^{-2}$, equivalent to $1.5 \times 10^4$ PFU/ml.

For infection studies, 96 well plates (Nunc) were seeded with 100 µL of cells ($2.5 \times 10^5$ cells/well) in DMEM/10% FCS and incubated at 37° C. and 5% $CO_2$ for 24 hrs until cells reached 80-90% confluency. CBM40 proteins (100 µL, 10-fold serial dilution of 10 mg/ml stock in SF-DMEM) were either added to cells before RSV infection (100 µL, $1.5 \times 10^3$ PFU per well in SF-DMEM), mixed with RSV for 1 hour on ice before adding to cells, or added to cells after RSV infection. In each case, CBM40s and/or RSV were left for 1 hour before removal. Cells were then overlaid with 300 µL AVICEL and plates were left to incubate for either 24, 48, 72, or 90 h at 37° C. and 5% $CO_2$.

To determine the level of RSV in cells post infection, AVICEL was removed and cells were fixed with 10% PFA in PBS for 10 min at room temperature prior to immunostaining with primary mouse anti-RSV F antibody (1:200 dilution, Serotec) followed by goat anti-mouse HRP IgG antibody (1:2000, Santa Cruz). The presence of RSV was detected using the colorimetric substrate TMB (Sigma). Absorbance was measured at the 450-nm wavelength (620-nm wavelength used as reference).

Statistical Analysis. Group comparisons were made using one-way ANOVA and Dunnett's multiple comparisons test. GraphPad Prism 7 (GraphPad Software) was used for all analysis. Tests with $p<0.05$ were deemed statistically significant. Unless otherwise stated, all values are presented as mean±SD, with statistical results presented as: *$p<0.05$, $p<0.01$, *$p<0.001$, and ****$p<0.0001$.

SUMMARY

The results are summarized in FIGS. 2, 3, 4 and 22.
1. Single dose administration of mCBM40s, when given prior to, or at the same time, as RSV in a Hep2:Npro mammalian cell line, appeared to reduce or inhibit RSV attachment to cells.
2. When given at the same time with RSV, all mCBM40s, up to 0.1-1 mg/ml concentrations, appeared to have a significant effect in reducing RSV infection compared to prophylactic dosing, when cells were tested up to 90 h post-infection.
3. Dosing of mCBM40s 24 h post RSV infection demonstrated reduction of viral infection when given at the highest dose. The highest dose of Vc2CBMTD when given at 24 h, 48 h and 72 h post RSV administration appeared to beneficially affect RSV levels in the Hep2: Npro mammalian cell line.
4. Of the mCBM40s tested, Vc2CBMTD appeared to be the most effective against RSV infection in the mammalian cell line.

REFERENCES

[1] Connaris H, Crocker, P R and Taylor, G L (2009). Enhancing the Receptor Affinity of the Sialic Acid-binding Domain of *Vibrio cholerae* Sialidase through Multivalency. JBC 284: 7339-7351.
[2] Connaris H, Govorkova E A, Ligertwood Y, Dutia B M, Yang L, Tauber S, Taylor M A, Alias N, Hagan R, Nash A A, Webster R G, Taylor G L (2014). Prevention of influenza by targeting host receptors using engineered proteins. *Proc Natl Acad Sci USA* 111:6401-6406.
[3] Harris, J and Werling, D (2003). Binding and entry of respiratory syncytial virus into host cells and initiation of the innate immune response. Cellular Microbiology 5: 671-680.
[4] Hilton, L., Moganeradj, K., Zhang, G., Chen, Y. H., Randall, R. E., McCauley, J. W., and Goodbourn, S (2006). The NPro product of bovine viral diarrhea virus inhibits DNA binding by interferon regulatory factor 3 and targets it for proteasomal degradation. *J Virol* 80(23), 11723-32.

Example 2

Sp2CBMTD: Prediction of Immunogenic Regions
Nordic Biopharma in Silico Screen
The in silico T-cell epitope screening identified four significant and two borderline immunogenic clusters:
Significant:

| Domain | Residue range | Sequence |
| --- | --- | --- |
| SpCBM | 245 to 254 | GVLSRTSLRS (SEQ ID NO: 21) |
| PaTD | 340 to 349 | WFSVSSNSLY (SEQ ID NO: 22) |
| PaTD | 351 to 359 | LSHGLQRSP (SEQ ID NO: 23) |
| PaTD | 398 to 406 | GSLNIRLGT (SEQ ID NO: 24) |

Borderline:

| Domain | Residue range | Sequence |
|--------|---------------|----------|
| SpCBM  | 167 to 178    | FYNLFSVSSATK (SEQ ID NO: 25) |
| SpCBM  | 239 to 251    | VRLYVNGVLSRTS (SEQ ID NO: 26) |

ProImmune Human Donor T-Cell Proliferation Assay

The ProImmune study highlighted two regions of high antigenicity and two regions of moderate antigenicity:

High Antigenicity:

| Domain | Residue range | Sequence |
|--------|---------------|----------|
| SpCBM  | 236 to 250    | KGRVRLYVNGVLSRT (SEQ ID NO: 27) |
| PaTD   | 392 to 406    | GAQVEVGSLNIRLGT (SEQ ID NO: 28) |

Moderate Antigenicity:

| Domain | Residue range | Sequence |
|--------|---------------|----------|
| SpCBM  | 167 to 181    | FYNLFSVSSATKKDE (SEQ ID NO: 29) |
| PaTD   | 338 to 352    | SDWFSVSSNSLYTLS (SEQ ID NO: 30) |

ProPred in Silico Analysis

Figure 5A:
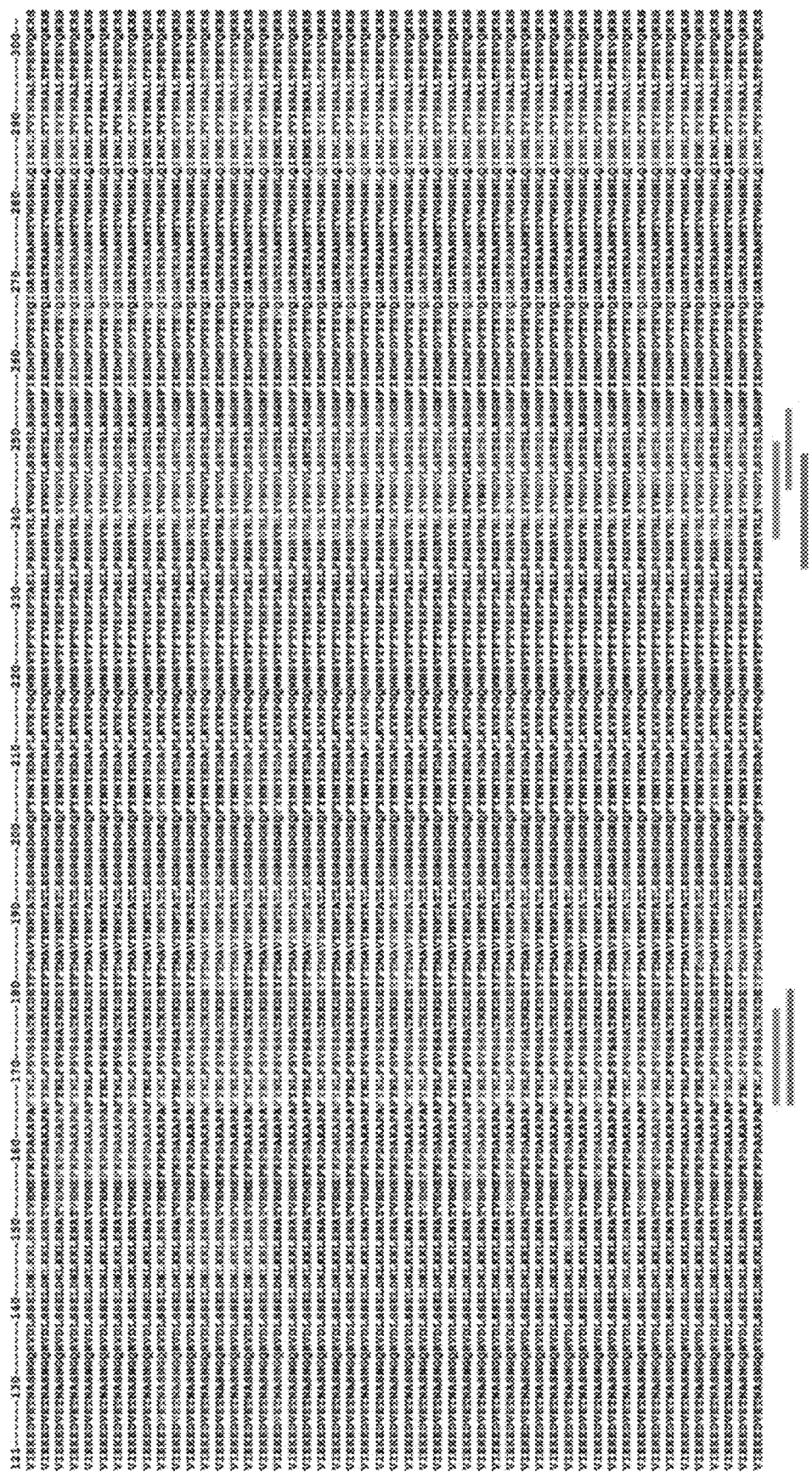
Figure 5B:
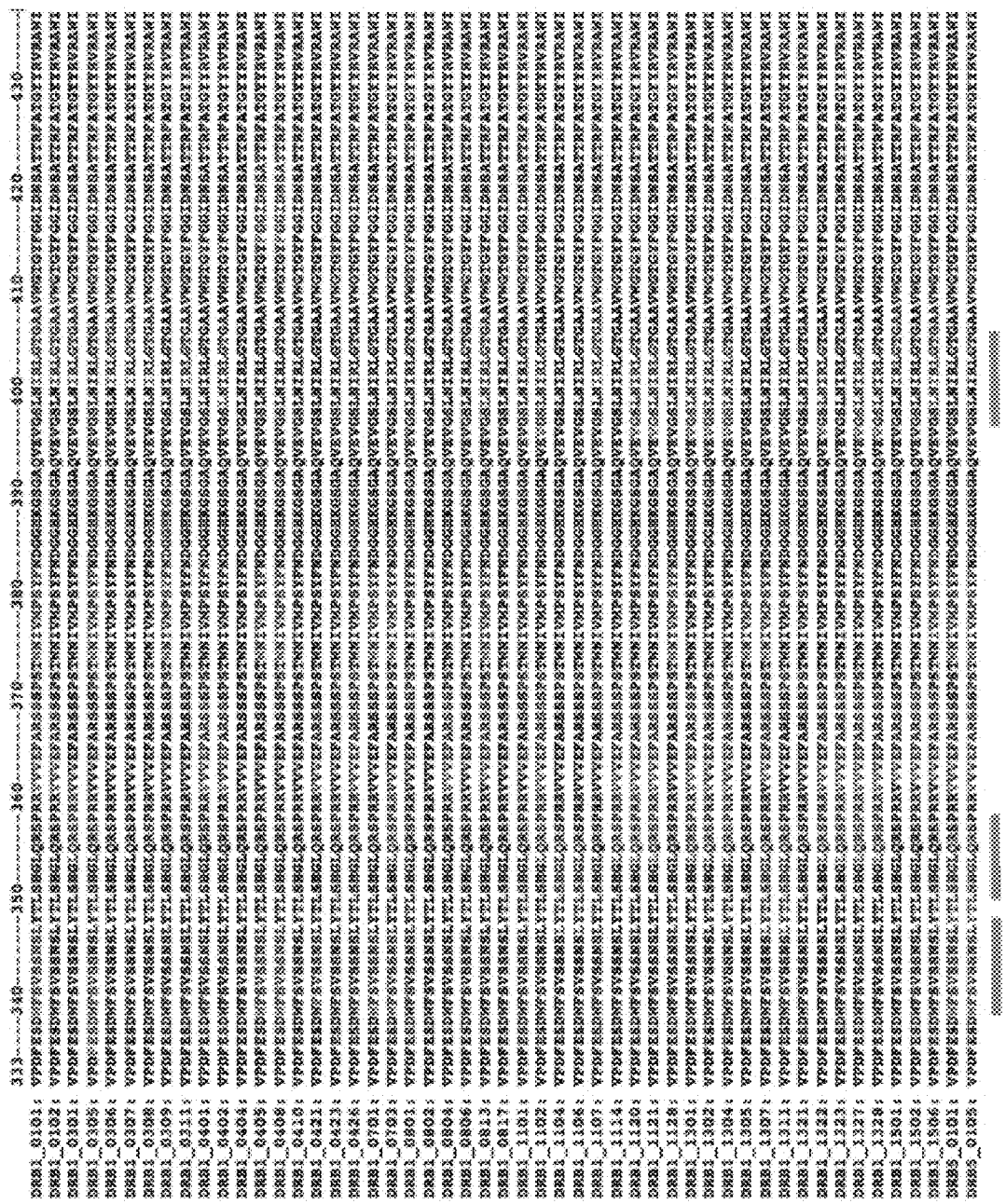

A further in silico tool, the online ProPred server[4], was also used. The output of the ProPred server is shown in FIG. 5. The relative positions of the Nordic Biopharma/ProImmune epitopes are also highlighted and indicate reasonable agreement between the three methods. In addition to the epitopes listed above, ProPred strongly predicted another immunogenic epitope in the SpCBM domain:

| Domain | Residue range | Sequence |
|--------|---------------|----------|
| SpCBM  | 286 to 294    | IRNLTVYNR (SEQ ID NO: 31) |

Mutations in the Individual CBM and TD Domains

To guide the design of mutations that might reduce immunogenicity, ProPred was used to test the effect of changing each residue in these peptides to every alternative residue. Those that gave the greatest reduction in predicted number of allele binders were noted. As the crystal structure of both the SpCBM and TD domains are known, these mutations were also modelled to reduce the likelihood of introducing mutations that would obviously disrupt the protein structure.

Initially, nine single mutations in SpCBM and four single mutations in PaTD were introduced and are listed below ('Im' is short for immunogenicity mutant):

| (SpCBM) variants | Mutation | (PaTD) variants | Mutation |
|------------------|----------|-----------------|----------|
| WTSp             | —        | WTTD            | —        |
| Im15             | Y168W    | Im24            | S342D    |
| Im16             | L170A    | Im25            | S345D    |
| Im17             | L170T    | Im26            | L348D    |
| Im18             | V173G    | Im27            | R403K    |
| Im19             | V239A    |                 |          |
| Im20             | V239T    |                 |          |
| Im21             | V246G    |                 |          |
| Im22             | I286A    |                 |          |
| Im23             | Y292E    |                 |          |

Note:
Im1 to Im14 (not shown) were introduced by mutagenesis into a non-codon optimized background, before the ProImmune data were available.

Synthesis of WT and Mutated Constructs

The genes encoding WT SpCBM, WT PaTD and the variants Im15 to Im27 were codon optimized for *E. coli* expression and synthesized by GeneArt. The genes were then cloned in-house into the pHISTEV vector for expression as 6His-tagged proteins.

Expression and Biophysical Characterization

Figure 6:
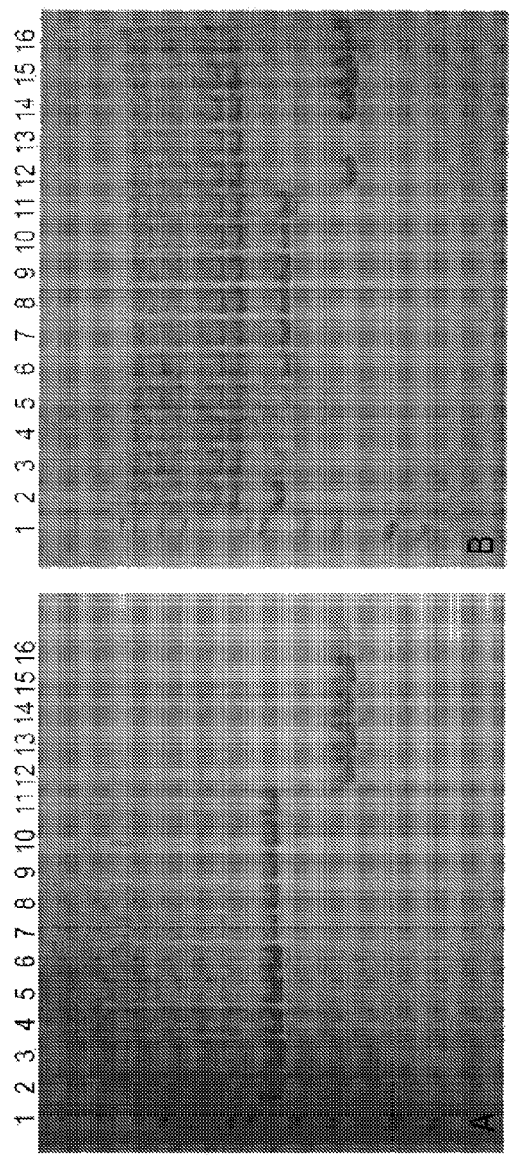

An initial expression test was performed to assess solubility. The results show that all were expressed, but not all were soluble (FIG. 6). Note: solubility (or a lack thereof) is not necessarily a predictor of utility. One of skill will appreciate that when manufacturing or producing proteins, certain processes require the use of insoluble material as this is readily purified (from inclusion bodies and the like). Downstream protocols may then re-engineer proteins to modulate features such as solubility.

Results of the expression test show that:

Im16 (L170A) is insoluble or very poorly soluble

Im25 (TD, S345D) is insoluble

Im15 (Y168W) and Im17 (L170T) have reduced solubility

Im18 (V173G) and Im22 (I286A) are slightly reduced.

The remainder show soluble expression.

The 13 soluble proteins were expressed in *E. coli* and purified by immobilized metal affinity chromatography (IMAC), followed by TEV digestion to remove the 6His-tag, then reverse IMAC and size exclusion chromatography (SEC).

Ten purified domains (WTSp, Im19, Im20, Im21, Im22, Im23, WTTD, Im24, Im26 and Im27) were further characterized by:

(i) Thermofluor to measure melting temperature (Tm)

(ii) Near UV circular dichroism (CD) to compare tertiary structures to WT (iii) Dynamic light scattering (DLS) to check oligomeric state in solution (iv) Surface plasmon resonance (SPR) to measure binding affinity to sialyllactose (v) Measurement of IL-8 cytokine stimulation The results are summarized in Table 1.

TABLE 1

Qualitative summary of the biophysical characterizations of the WT domains and their variants. Colour coding is from green to red (including green', orange and yellow), where green indicates that the variant closely resembles its WT counterpart for that particular characteristic and pale green (green') or yellow indicate increasing degrees of differences. Red or orange indicate significant differences.

| Name | Mutation | Solubility | Purification | Tm +/− 6SL | NearUV CD | DLS | Biacore | Cytokine stimulation |
|---|---|---|---|---|---|---|---|---|
| WTSp | — | Green | Green | Green | Green | Green | Green | Green |
| Im15 | Y168W | Yellow | Orange | Red | N/A | N/A | N/A | N/A |
| Im16 | L170A | Red | N/A | N/A | N/A | N/A | N/A | N/A |
| Im17 | L170T | Yellow | Orange | N/A | N/A | N/A | N/A | N/A |
| Im18 | V173G | Green' | Orange | N/A | N/A | N/A | N/A | N/A |
| Im19 | V239A | Green | Green | Green | Green | Green | Green | N/D |
| Im20 | V239T | Green | Green | Green' | Green' | Green | Green | N/D |
| Im21 | V246G | Green | Green | Green' | Green | Green | Green | Green |
| Im22 | I286A | Green' | Green | Green' | Green | Green | Green | Green |
| Im23 | Y292E | Green | Green | Green' | Green' | Green | Yellow | Yellow |
| Im24 | S342D | Green | Green | Green | Green | Green | | |
| Im25 | S345D | Red | N/A | N/A | N/A | N/A | | |
| Im26 | L348D | Green | Green | Green' | Green | Green | | |
| Im27 | R403K | Green | Green | Green | Green | Green | | |
| WTTD | — | Green | Green | Green | Green | Green | | |

N/A: these characterizations were not performed due to poor solubility/purity of the protein.
N/D: not determined.

Sp Peptide 167-181:

Im15, Im16, Im17, Im18 are all insoluble or poorly soluble (as stated, this does not necessarily impact on protein utility). These are in the 'moderately' antigenic region 167-181 (FYNLFSVSSATKKDE). This region is clearly very sensitive to change.

Earlier results show that M156F, which sits adjacent to L170 (and 1286), increases Tm by ~4° C.

This could therefore be combined with L170T. M156F does not increase predicted immunogenicity.

Figure 7:
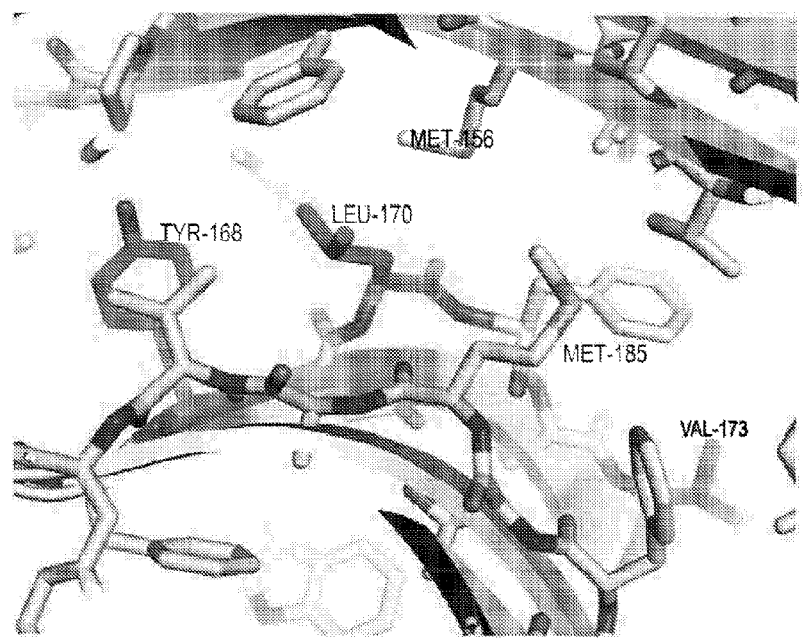

M185I increases Tm by 5° C., and lies parallel to L170 (FIG. 7). This mutation could also be included. Note that, like M156F, M185I does not increase predicted immunogenicity but slightly reduces the number of predicted allele binders.

Sp Peptide 236-250:

Im19, Im20, Im21 all behave similarly to WT. These are in the 'highly' antigenic region 236-250 (KGRVRLYVNGVLSRT).

Im19 (V239A) was chosen over the threonine mutation (Im20, V239T). There is no difference in predicted immunogenicity but Im19 is a closer match to WT Thermofluor Tm and Near UV spectrum. This would be combined with Im21 (V246G).

Sp Peptide 286-294:

Im22 (I286A) is broadly similar to WT while Im23 (Y292E) appears to exhibit reduced ligand affinity. This region, 286-294 IRNLTVYNR, was not flagged up by ProImmune but is strongly predicted by ProPred to be immunogenic.

There is some indication that Im22 has lower Tm than WT. This residue is adjacent to M156 so may behave differently if M156F was included.

TD Peptide 338-352:

Im24 (S342D) and Im26 (L348D) show similar characteristics to the WT trimerization domain, but with some suggestion of reduced Tm in Im26. These are in the 'moderately' antigenic region 338-352 SDWFSVSSNSLYTLS. The WT sequence was predicted to bind 9 alleles, while Im24 predicts 2 alleles and a Im24/Im26 double mutant predicts 1 allele.

TD Peptide 392-406:

Im27 (R403K) is similar to WT. It is part of the 'highly' antigenic region 392-406 GAQVEVGSLNIRLGT. Predicted alleles are reduced from 21 to 3 when this mutation is introduced.

Synthesis of Multiple Mutation Combinations Im28-34

The following mutations were introduced:

i) M156F/L170T ii) M156F/L170T/M185I: In ProPred, alleles predicted for this region are reduced from 31 in the WT to 19 for this combination.

iii) V239A/V246G: In ProPred, alleles for this region are reduced from 44 to 3.

iv) I286A/Y292E: In ProPred, alleles are reduced from 41 to 1.

v) V239A/V246G/I286A/Y292E combines the previous two doubles.

vi) M156F/L170T/M185I/V239A/V246G/I286A/Y292E combines all the Sp mutations vii) TD: S342D/L348D/R403K: Predicted alleles are reduced from 9 to 1 for TD peptide 338-352 and alleles for peptide TD peptide 392-406 are reduced from 21 to 3. This triple mutant combines all the TD mutants. They are all surface exposed and distal to the N-terminal end of TD, so would not be expected to interfere with SpCBM in the hexamer form.

The constructs are named Im28 to Im34:

| (SpCBM) variant | Mutations |
|---|---|
| Im28 | M156F/L170T |
| Im29 | M156F/L170T/M185I |
| Im30 | V239A/V246G |
| Im31 | I286A/Y292E |
| Im32 | V239A/V246G/I286A/Y292E |
| Im33 | M156F/L170T/M185IA/239A/V246G/I286A/Y292E |

| (PaTD) variant | Mutation |
|---|---|
| Im34 | S342D/L348D/R403K |

2.5 Expression and Biophysical Characterization of Im28-Im34

Figure 8:
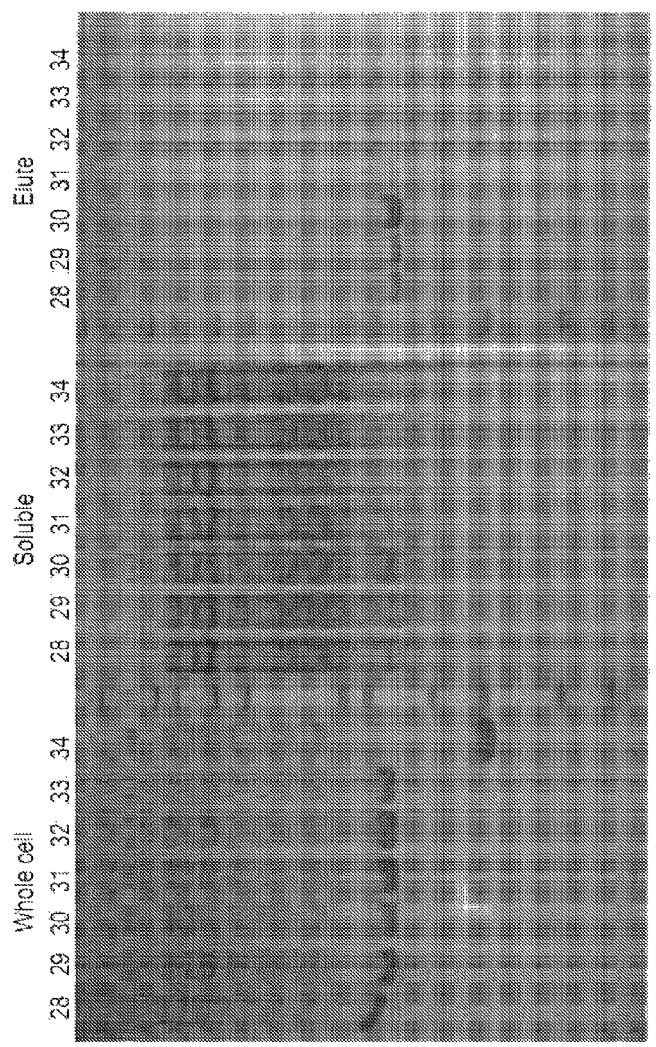

As with the single mutations, the combinations Im28 to Im34 were synthesized by GeneArt and subcloned into pHISTEV for expression analysis. A nickel bead pull-down on the His-tagged soluble extract was also performed (FIG. 8).

Hexameric Forms

Design of Hexameric Constructs HEX1 to HEX17

Genes encoding the hexameric forms (called HEX1 to HEX17) were synthesized by GeneArt:

| variant | Sp2CBMTD Mutations |
|---|---|
| HEX1 | CBM1(L170T V239A V246G I286A Y292E)-CBM2(L170T V239A V246G I286A Y292E)-TD (S342D L348D R403K) |
| HEX2 | CBM1(V239A V246G I286A Y292E)-CBM2(V239A V246G I286A Y292E)- TD (S342D R403K) |
| HEX3 | CBM1(V239A V246G I286A)-CBM2(V239A V246G I286A)-TD (S342D R403K) |
| HEχ4 | CBM1(V239A V246G)-CBM2(V239A V246G)-TD(S342D) |
| HEχ5 | CBM1(V239A V246G)-CBM2(V239A V246G)-TD(R403K) |
| HEχ6 | CBM1(V239A V246G)- CBM2(V239A V246G)-TD(S342D R403K) |
| HEχ17 | CBM1(V239A V246G A162P)- CBM2(V239A V246G A162P)-TD (S342D R403K) |

The hexameric forms were synthesized in two parts to avoid problems associated with synthesising repeat sequences in the tandem CBM copies. The first gene covered the first CBM and the second part encompassed the second CBM plus the TD. These could then be simultaneously cloned into pHISTEV to create the Sp2CBMTD construct that trimerizes upon expression.

The first hexamer, HEX1, contained the mutations L170T/V239A/V246G/I286A/Y292E in the CBMs and S342D/L348D/R403K in the TD.

The solubility data of the individual domains indicated that HEX1 was unlikely to be soluble (again, not necessarily a reflection on the utility of the molecule); a further construct, HEX3, was synthesized. Note that HEX2 contained the same mutations as HEX3, but with the addition of Y292E.

HEX3 was synthesized and subcloned into the pHISTEV vector. Expression was insoluble under all conditions tested (varying temperature, IPTG concentration, cell density at induction, with or without heat shock). The CBM-only domain containing the same three mutations (V239A V246G I286A) is soluble. A double mutant (V239A V246G) behaves very similarly to WT. Therefore, further variants (HEX4, HEX5 and HEX6) were designed and constructed by PCR/ligations, which exclude I286A and contain either one or both of the TD mutations.

During the work on HEX6 a number of other versions were designed containing different combinations of the HEX6 mutations (numbered HEX7 to HEX16; not characterised).

HEX17 contains the HEX6 mutations with an additional A162P mutation. This proline mutation has been shown to increase the single CBM Tm by 3-4° C. The proline mutation is not near the other mutations, the N- or C-termini or the ligand binding site.

Characterization of the Hexameric Variants stimulated with the modified hexamer HEX17, IL-8 levels are significantly lower than when compared to Sp2CBMTD (aka SpOrig) stimulated cells.

Figure 9:
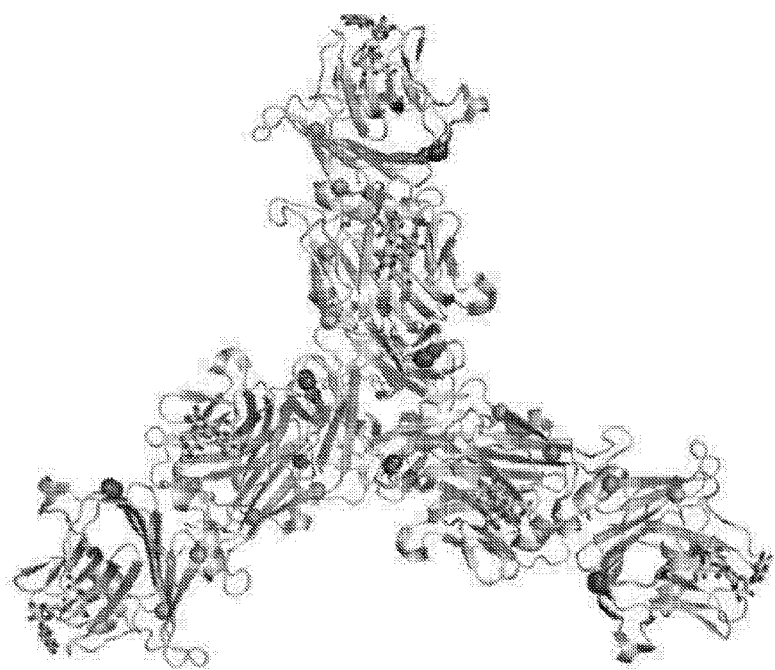

The expression, purification and characterization results are shown in Table 2. Based on these results, HEX6 and HEX17 were taken forward. The positions of the HEX17 mutations on the hexamer are shown in FIG. 9.

TABLE 2

Qualitative summary of the biophysical characterizations of the hexameric Sp2CBMTD variants. Colour coding is from green to red, where green indicates that the variant closely resembles its WT counterpart for that particular characteristic and pale green (green') or yellow indicate increasing degrees of differences. Red or orange indicate significant differences.

| Name | Mutations | Solubility | Purification | Thermostability | NearUV CD | Biacore | IL-8 assay |
|---|---|---|---|---|---|---|---|
| Hex1 | L170T/V239A/V246G/I286A/Y292E/S342D/L348D/R403K | Red | N/A | N/A | N/A | N/A | N/A |
| Hex2 | V239A/V246G/I286A/Y292E/S342D/R403K (designed but not made) | | | | | | |
| Hex3 | V239A/V246G/I286A/S342D/R403K | Red | N/A | N/A | N/A | N/A | N/A |
| Hex4 | V239A/V246G/S342D | Yellow | Red | N/A | N/A | N/A | N/A |
| Hex5 | V239A/V246G/R403K | Green | Yellow | Yellow | N/A | N/A | N/A |
| Hex6 | V239A/V246G/S342D/R403K | Green | Green | Yellow | Green | Green | Yellow |
| Hex7 to 16 | Note: These constructs are different combinations of the Hex6 mutations and were designed as a back-up in case Hex6 failed | | | | | | |
| Hex17 | A162P/V239A/V246G/S342D/R403K | Green | Green | Green' | Green | Green | reduced IL-8 |

N/A: these characterizations were not performed due to poor solubility/purity of the protein.
N/D: not determined.

Example 3: Inflammatory Mediators

Aim: To Measure the Innate Immune Response of mCBM-Treated Human Lung Epithelial Cells (A549) by Analysing Levels of Inflammatory Mediators Over Time.

Administration of Sp2CBMTD to mammalian cells stimulated a pro-inflammatory response both in vitro and in vivo[1,2]. To determine whether this was still observed with modified hexameric sialic acid binding molecules, mammalian A549 cells were stimulated by the addition of 10 µg of biologic (Sp2CBMTD aka SpOrig), HEX6 (i.e. a sialic acid binding molecule comprising 3×HEX6 units) or HEX17 (i.e. a sialic acid binding molecule comprising 3×HEX17 units) and cell culture medium was harvested at specific timepoints post administration. The concentrations of inflammatory mediators were measured both by ELISA and a multiplex assay.

Figure 10:
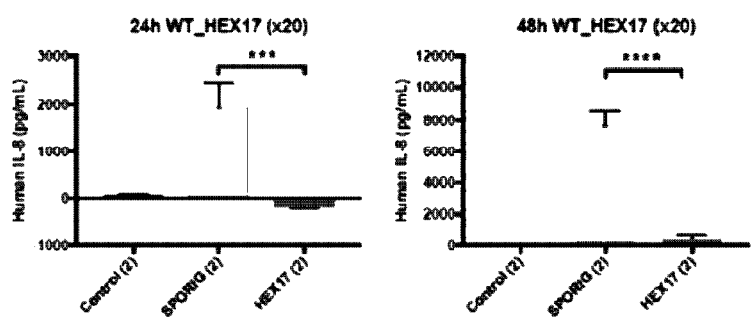
Figure 11A:
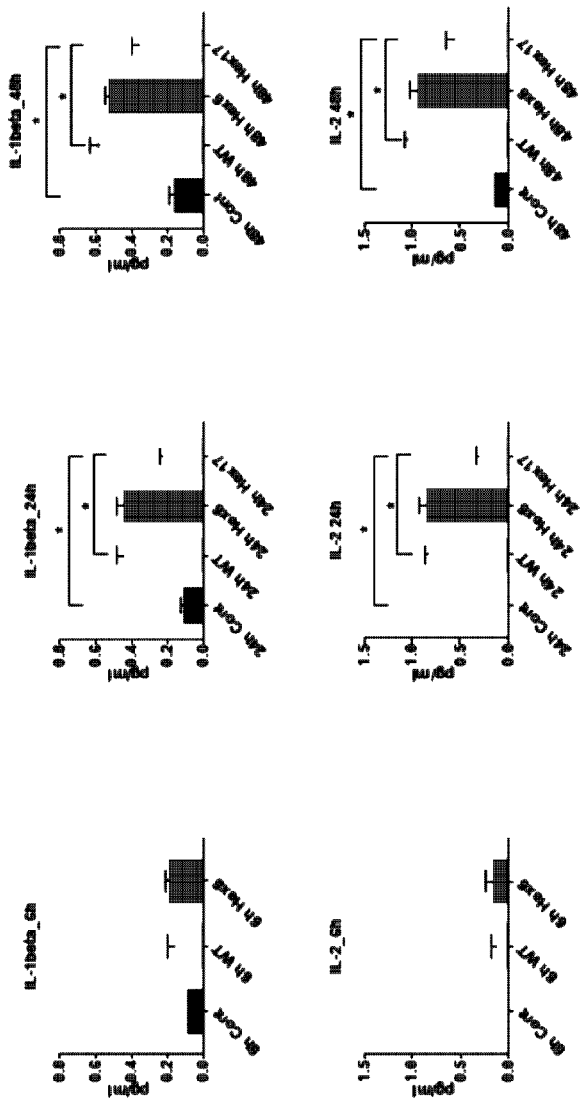
Figure 11B:
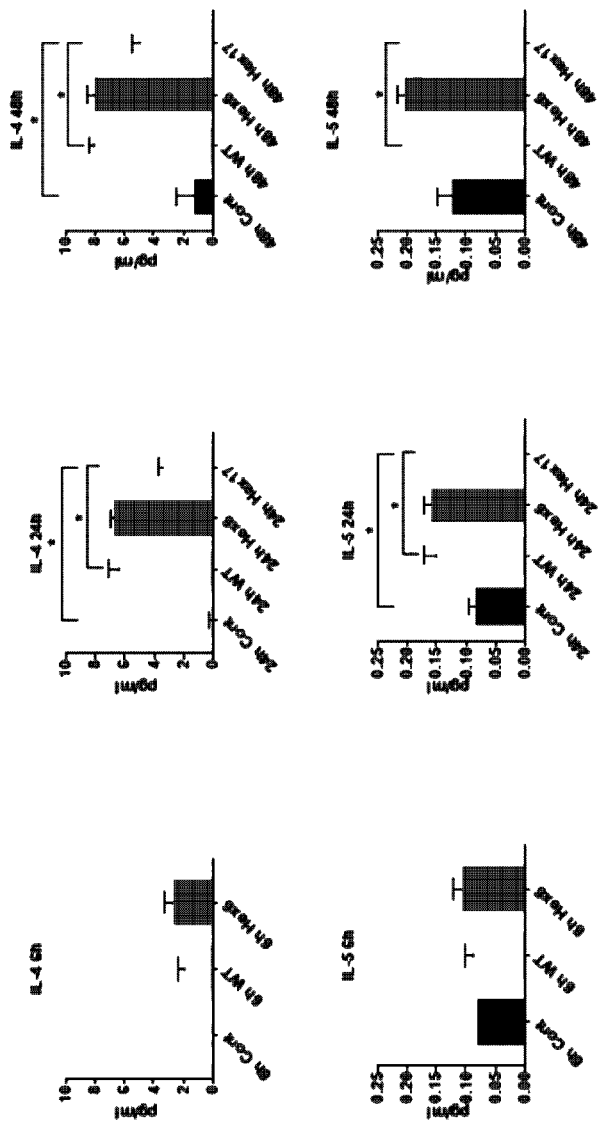
Figure 11C:
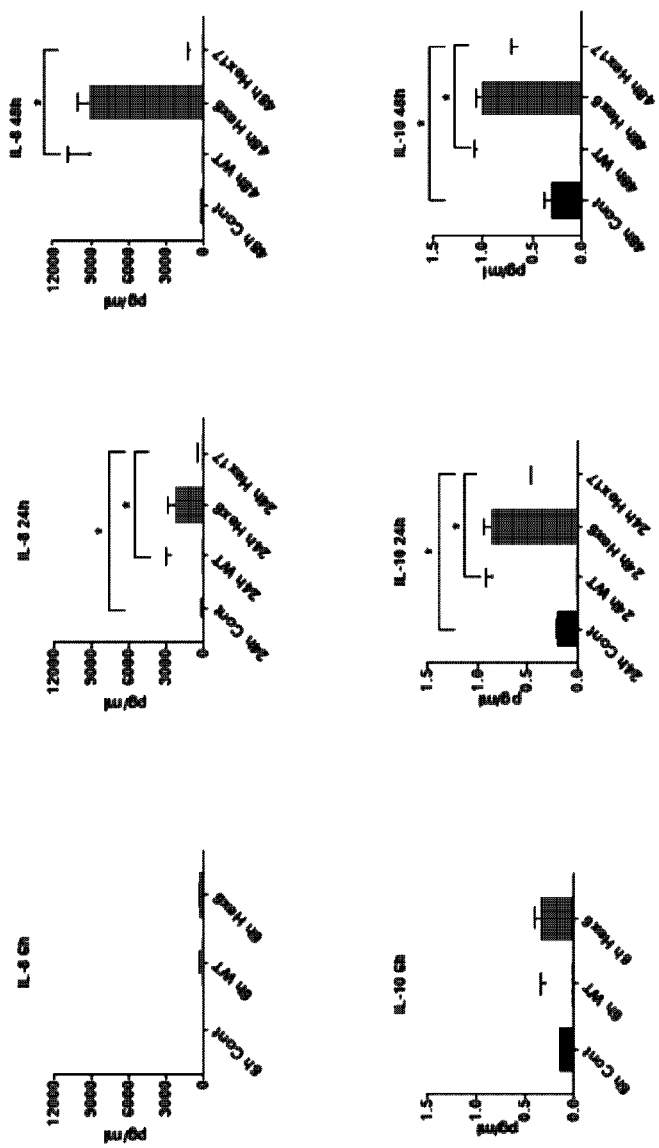
Figure 11D:
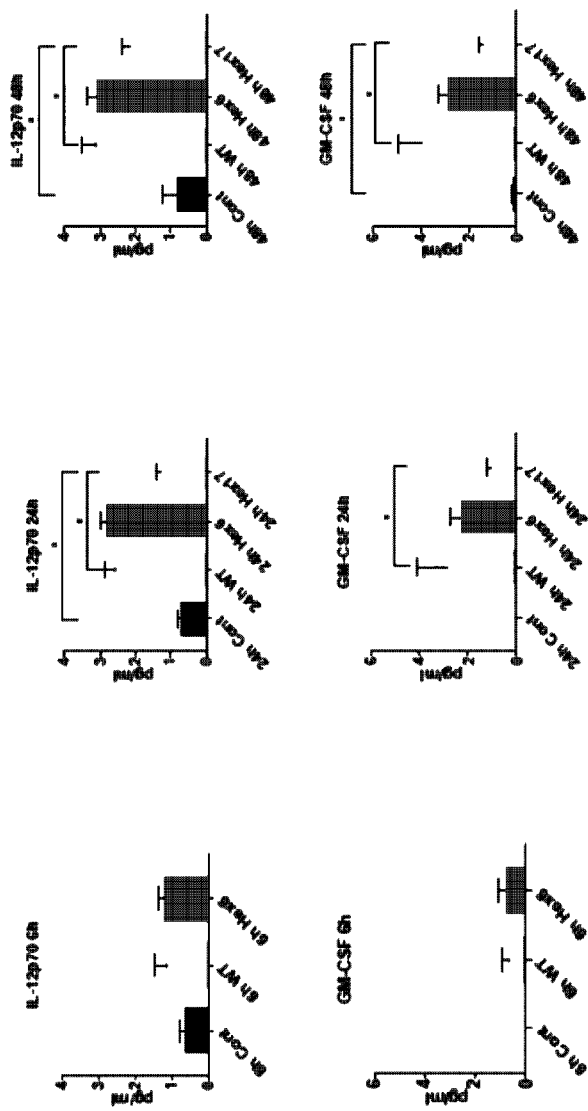
Figure 11E:
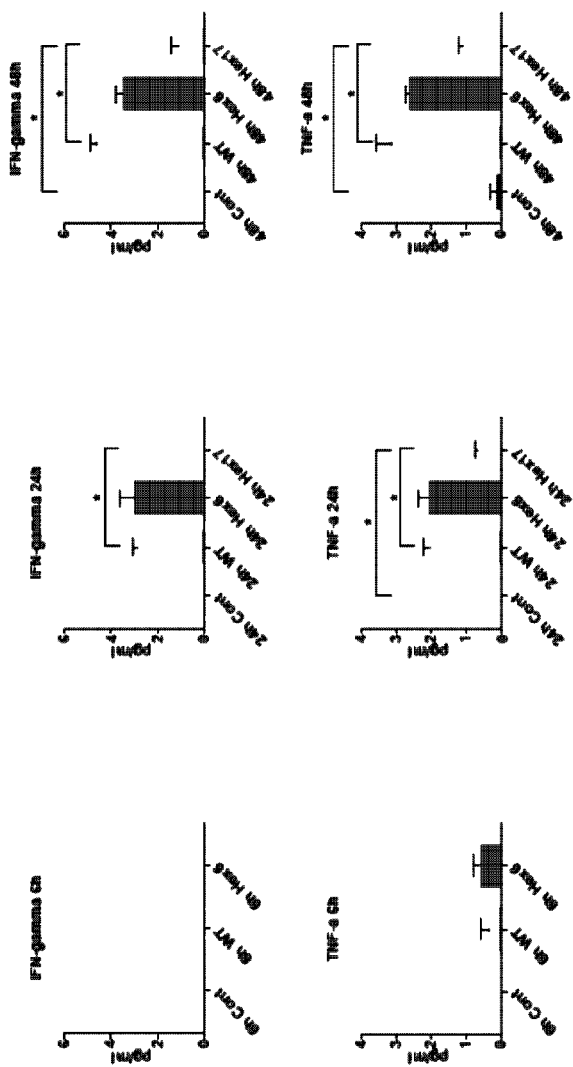
Figure 11F:
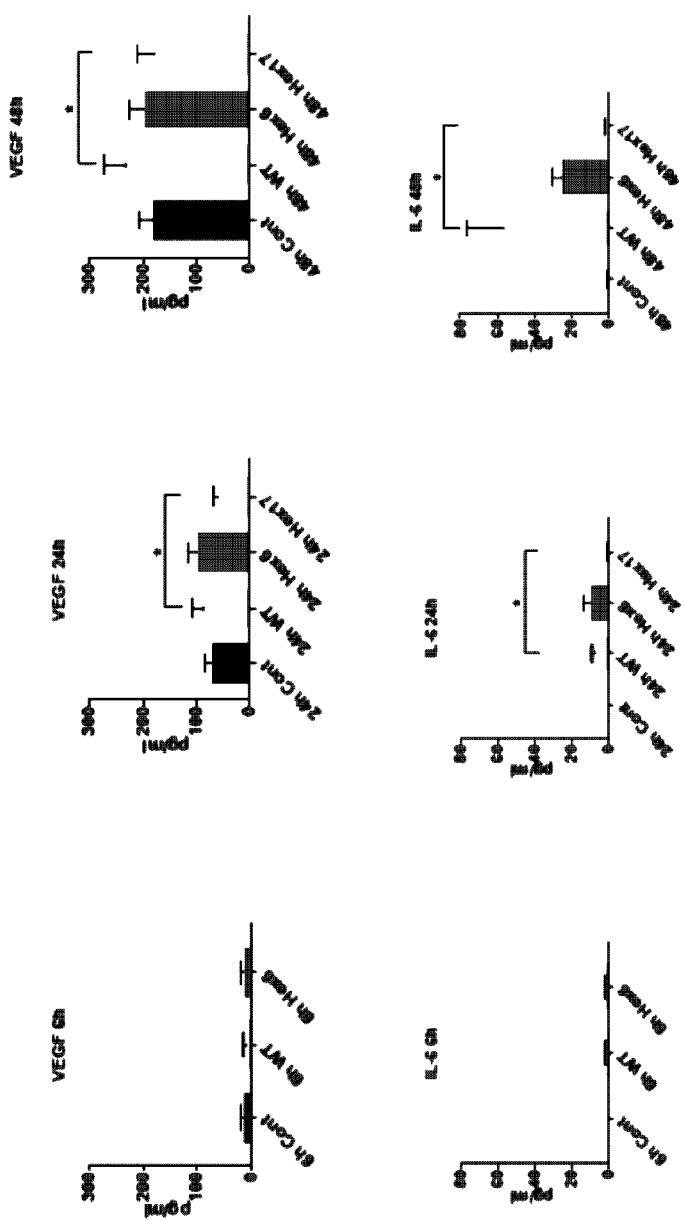

Human IL-8 (benchmark cytokine for the study) response using a human 1×Mouse CXCL1/KC Quantikine ELISA Kit (R&D BioSystems). The concentration levels of IL-8 from stimulated A549 cells are shown in FIG. 10. It is evident that when A549 cells are Inflammatory mediator response using a Human Cytokine 12-plex Assay (Bio-Plex Pro™, Bio-Rad). FIG. 11 demonstrates the analysis of 12 inflammatory mediators from culture medium after A549 cell stimulation by Sp2CBMTD (WT, aka SpOrig), HEX6 and HEX17 (variants) at specific time points (6 h, 24 h, 48 h). Prior to analysis, samples were thawed and diluted 1:4 in PBS before using a human HS Cytokine-12 plex assay (R&D Systems). The data indicates that:

- HEX17 affects the levels of almost all the cytokines tested compared to SpOrig and HEX6. There is a significant reduction in observed concentration (pg/ml) with analytes IL-6, IL-8, GM-CSF and IFN-gamma at 48 h when compared to SpOrig and HEX6.
- When compared to control at 48 h, HEX17 appears to cause an increase in the level of all cytokines tested with the exception of IL-5, and VEGF (yet to be confirmed).
- HEX6 only showed reduced IL-6 stimulation compared to SpOrig at 48 h.

Example 4: In Vivo PR8 Mouse Data

The objective of the study was to assess the efficacy of Sp2CBMTD (SpOrig) and its variants, in a mouse model of lethal influenza infection. Each of the candidate proteins were also administered in the absence of an influenza infection to assess whether they alone, caused any morbidity or mortality.

Survival, Clinical Scores and Weight Loss.

Figure 12:
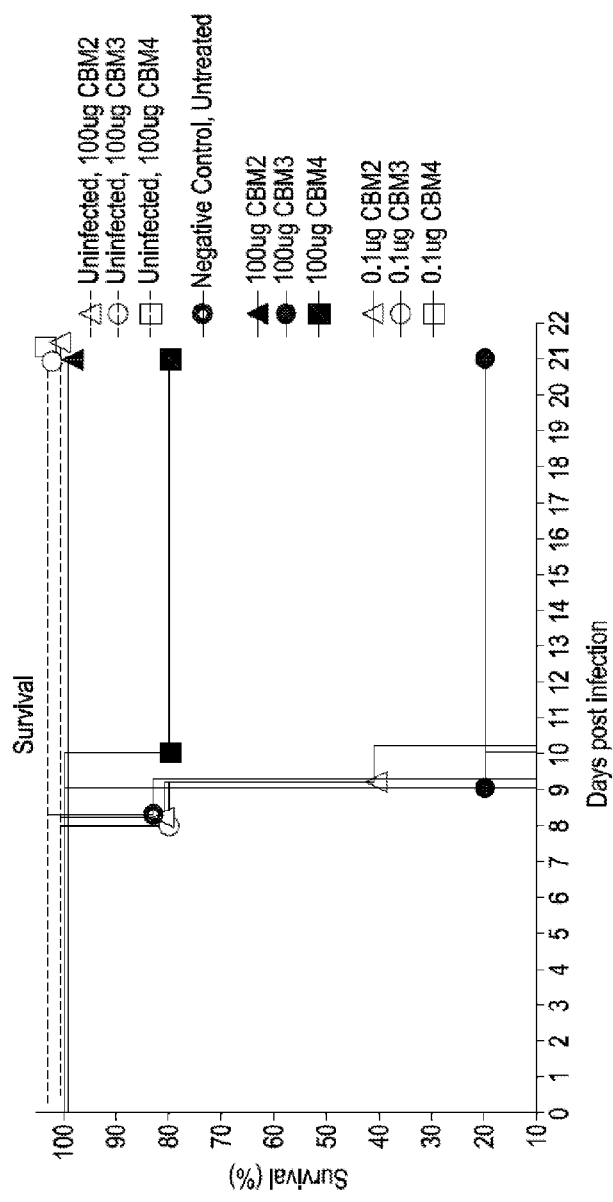
Figure 13:
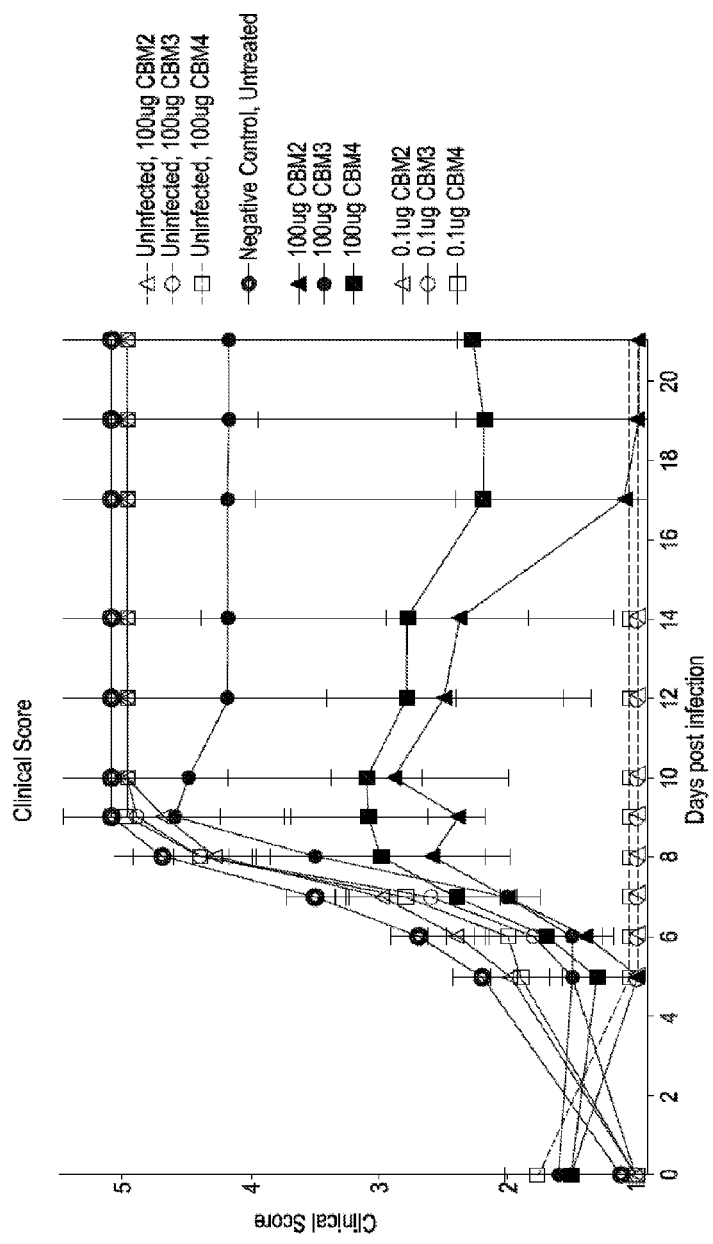
Figure 14:
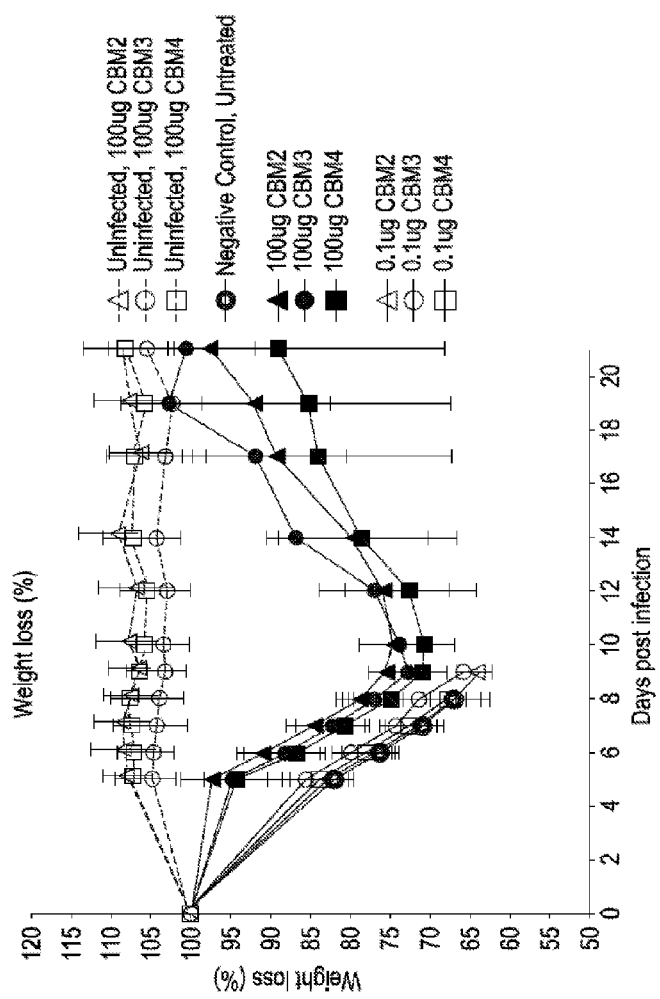

The results show that none of CBM2 (HEX17), CBM3 (HEX6) or CBM4 (WT, SpOrig) caused any overt morbidity or mortality alone. Administration of a single 100 µg dose of either CBM2 (HEX17), CBM3 (HEX6) and CBM4 (WT, SpOrig) one day prior to a lethal challenge with PR8 influenza virus elicited protection against PR8 infection, with greatest efficacy seen with HEX17 (100% survival), followed by SpOrig and then HEX6 (FIG. 12). Clinical scores were also lower with HEX17 compared to SpOrig and HEX6 (FIG. 13). Mice from single high dose treated groups that survived all lost weight at peak infection but soon recovered, in contrast to untreated, infected mice (FIG. 14).

Anti-mCBM Antibody Analysis of Lung Homogenates and Sera Tissue from a PR8-Challenged Mouse Study.

Figure 15:
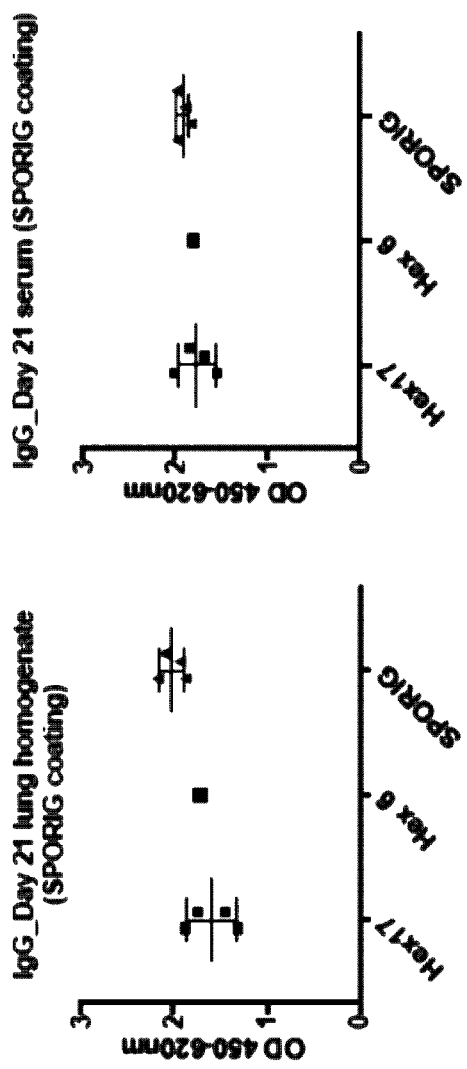
Figure 17A:
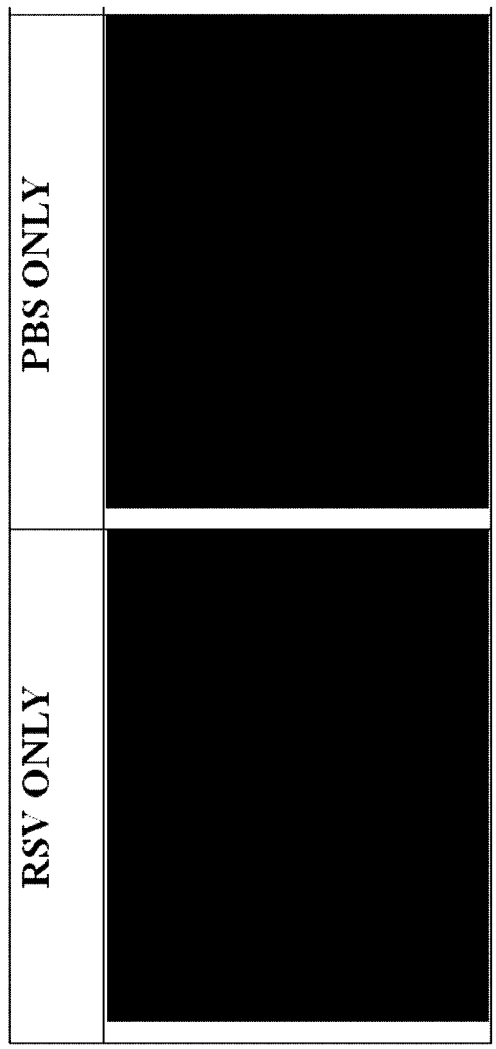
Figure 17B:
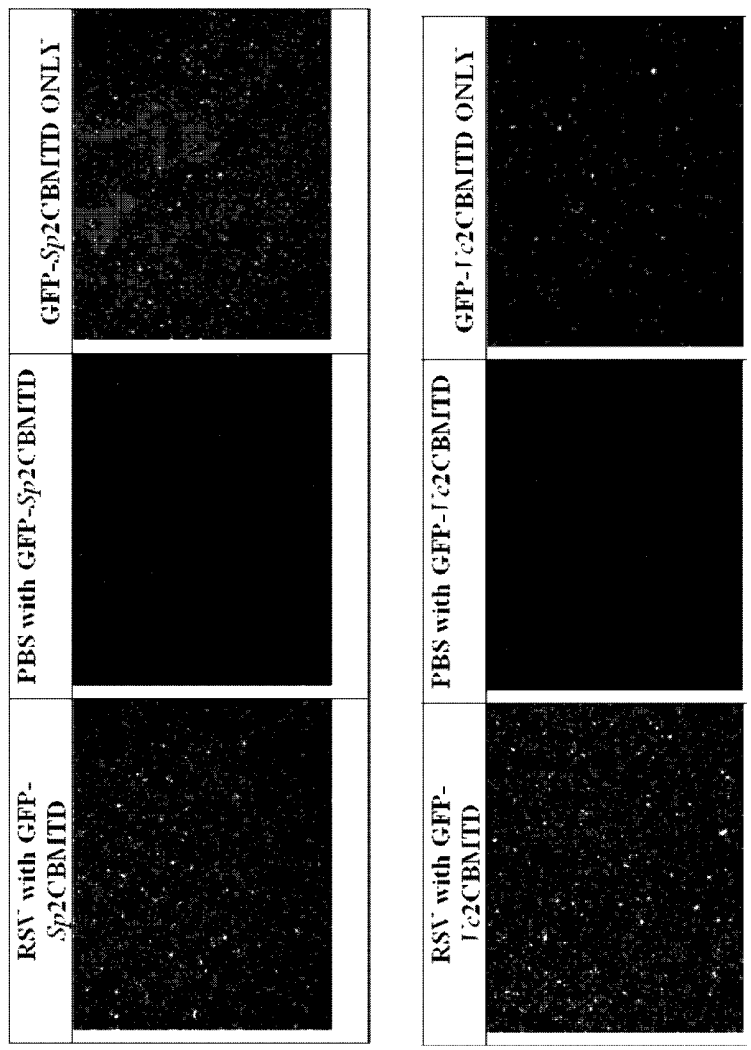
Figure 17C:
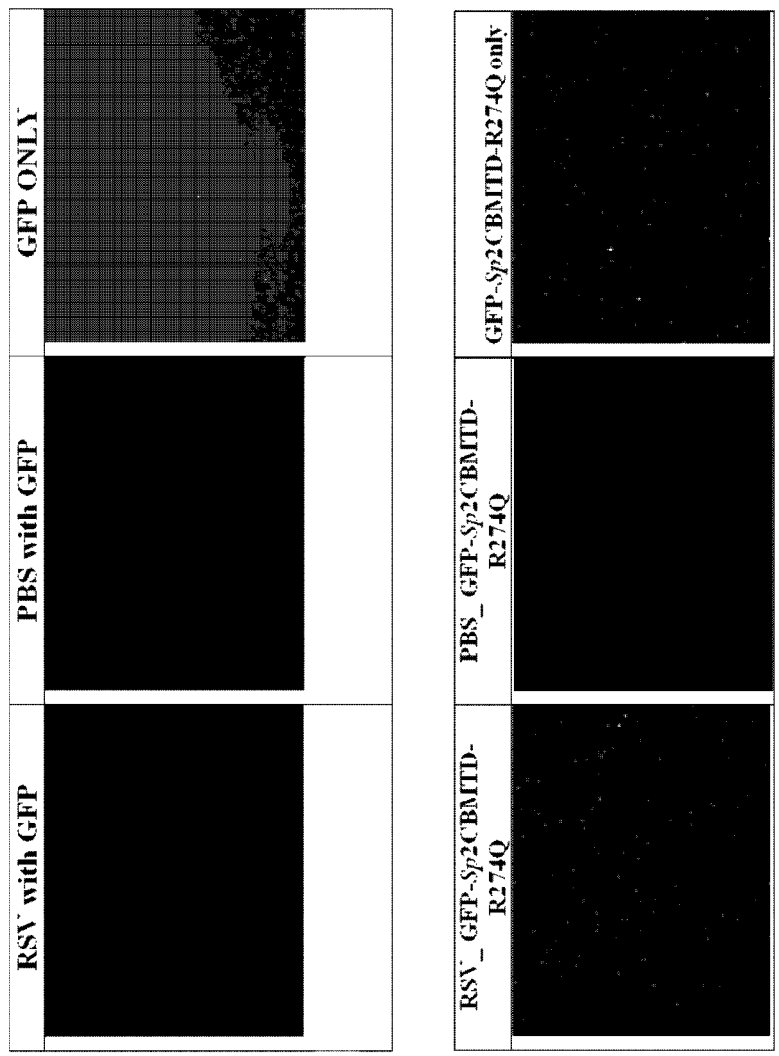

The objective of this study was to determine whether modified immunogenic epitopes of the modified variants of Sp2CBMTD (SpOrig) demonstrated reduced antibody levels in mice in a PR8-challenged study (it should be noted that epitopes were modified based on human MHC-class II binding information). For this, survived mice from PR8-challenged study were culled at Day 21 with lung and sera harvested and tested for anti-mCBM antibodies—IgG, IgA, IgE and IgM against coated antigen SpOrig (1 µg/well) in an ELISA format. The data shown in FIG. 15 indicated that:

- The modified protein HEX17 did show a significant (p<0.05) reduction in mouse lung IgM levels compared to SPORIG. Due to only one surviving mouse for HEX6 treatment, only HEX17 and SPORIG data was statistically analysed.
- There is some indication of a slight downward trend of antibody levels in mice (lung IgA and IgM) that were treated with the modified CBMs compared to SpOrig.

Example 5

The aim of the following experiments is to determine whether there is a direct interaction between CBMs (Sp2CBMTD and Vc2CBMTD) and human RSV in a cell-free system. ELISA experiments were designed as follows:

Experiment 1

96-well plate was pre-coated with different concentrations of RSV (strain type A2), CBMs, Sp2CBMTD and Vc2CBMTD and PBS (vehicle, negative control) overnight at 4° C. Wells were blocked with Blocking Buffer (BB, PBS containing 1% w/v BSA). Different concentrations of CBMs were diluted in BB and then added to the wells after removing coating antigens and blotting the plate. The plate was left to incubate for 1 hr at room temperature. Wells were then washed with Wash Buffer (WB, PBS supplemented with 0.5% (v/v) Tween-20) before adding primary antibodies (rabbit anti-SpCBM antibody or rabbit anti-VcCBM antibody, 1:5000 dilution in BB, Eurogentec) and left to incubate for 1-2 hr at room temperature. Goat anti-rabbit IgG-HRP (1:2500 dilution in BB, Sigma) was used as the secondary antibody and TMB (Sigma) was used for substrate. CBM binding to RSV was determined by comparing the absorbance at 450 nm (620 nm as background reference) of treated versus untreated control wells after reactivity with TMB (substrate for HRP).

Figure 16A:
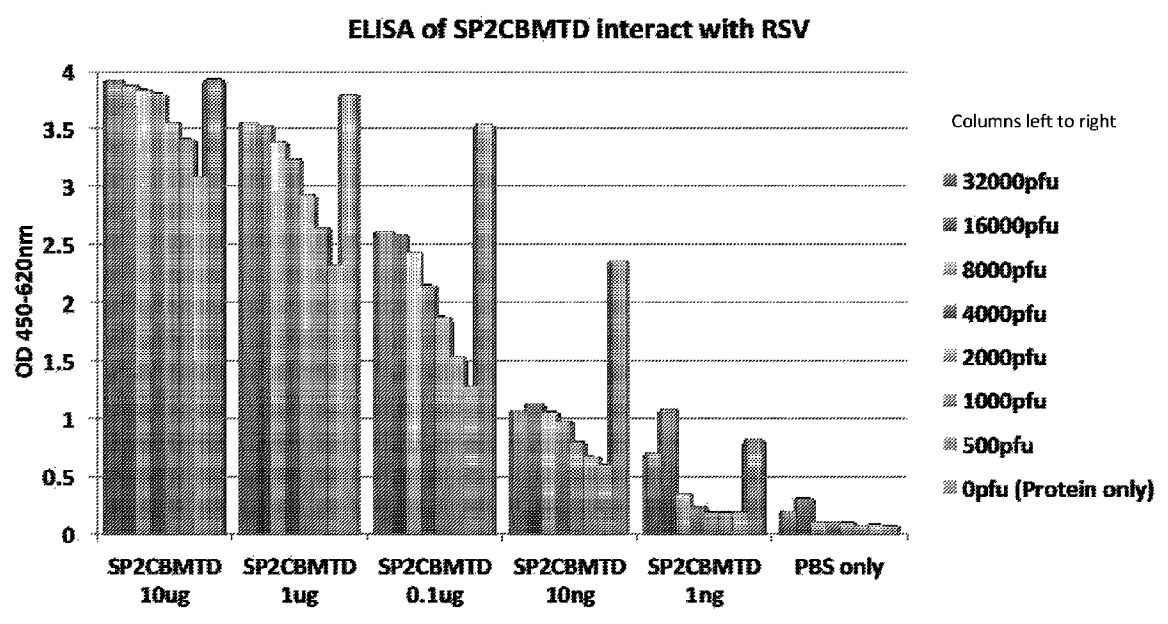
Figure 16B:
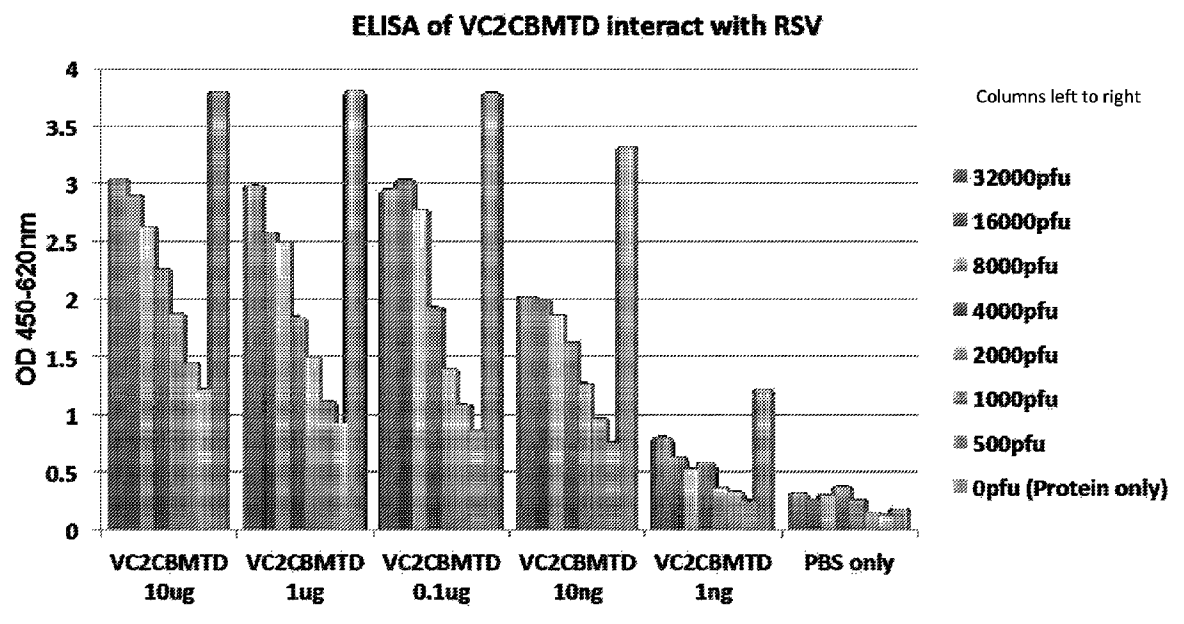

The results shown both Sp2CBMTD and Vc2CBMTD interact directly with RSV in a dose-dependent manner (see FIGS. 16A and B).

Experiment 2

A 96-well plate was pre-coated with 10 µg of either GFP-Sp2CBMTD, GFP-Vc2CBMTD, GFP, GFP-Sp2CBMTD-R274Q (a sialic acid binding mutant of Sp2CBMTD) or 32000 PFU RSV as coating antigens and PBS (vehicle, negative control). Wells were incubated with relevant proteins for 1 hr at room temperature. Images of GFP fluorescent binding were captured using a microscope (in the GFP channel on EVOS FL Cellular Imaging System) with 10×objective. The results indicate that both GFP-Sp2CBMTD and GFP-Vc2CBMTD are able to bind directly to RSV. Negligible binding to RSV was observed with the sialic acid binding mutant GFP-Sp2CBMTD-R274Q (see FIGS. 17A-E)

Example 6

The aim of the following experiments is to support the observation that the interactions between CBMs (Sp2CBMTD and Vc2CBMTD) and RSV are based on CBMs binding to the viral surface glycoproteins terminating with sialic acid. Thus, three ELISA experiments were designed.

Experiment 1

Both wild type Sp2CBMTD and mutant Sp2CBMTD-R274Q (sialic acid binding mutant) were used in an ELISA format as described in Experiment 1, Example 5. The results demonstrate that wild type Sp2CBMTD binds with much higher affinity to RSV than compared with the same concentration of mutant Sp2CBMTD-R274Q (see FIGS. 18A and B).

Experiment 2

Neuraminidase (Nu) from *Clostridium perfringens* (Sigma) is a glycosidase that is able to cleave terminal sialic acids from cell surface sialylated glycoconjugates, with linkage specificity for α-2,3-α-2,6-α-2,8-linked to Gal, GlcNac, GalNAc, AcNeu, GlcNeu, oligosaccharides, glycolipids or glycoproteins. To test whether this is the case for viral surface glycoproteins, RSV was treated with and without neuraminidase prior to the addition of CBMs. An ELISA experiment similar to Experiment 1 in Example 5, was set up. A 96-well plate was pre-coated with different concentration of RSV, CBMs (as positive controls) and PBS (as negative control). For some RSV-coated wells, neuraminidase (30 mU/well) was added for 1 hr followed by adding CBMs (100 ng or 10 ng). CBM binding was evaluated using anti-CBM antibodies followed by a detection anti-IgG-HRP as described in Project 1.

The results demonstrate that in the absence of neuraminidase treatment, both Sp2CBMTD and Vc2CBMTD interact with RSV in a dose-dependent manner as observed previously (below, and Experiment 1, Example 5). The interaction is partially abolished after neuraminidase treatment of RSV in the presence of Sp2CBMTD, but almost completely abolished when using Vc2CBMTD as the interacting partner (see FIGS. 19A and B).

This data provides evidence that RSV surface glycoproteins are sialylated suggesting a potential directly acting antiviral role of CBMs in RSV infection.

Experiment 3:

To determine whether a competing ligand can block the sialic acid binding site of CBMs and interfere with the interaction of CBM with RSV, CBMs (Sp2CBMTD and Vc2CBMTD, 100 ng/well) were pre-incubated with different concentrations of α2,3 sialyllactose (3'-SL, 10 mM, 100 mM, Glycotech) for 1 hr at room temperature. The mixture was added to a 96-well plate coated with the RSV (32000 PFU/well) along with controls (PBS, CBM only). CBMs were added to wells as in the ELISA experiment as in Example 5. The number of replicates in the study was n=3, Raw data were analyzed by one-way ANOVA using GraphPad Prism. A p value<0.05 was, considered statistically significant (*p<0.05; 88P<0.01; *p<0.001; **p<0.0001).

The result shown that a competing sialoside, 3'-SL is able to reduce the interaction between RSV and Sp2CBMTD and Vc2CBMTD in a dose-dependent manner (see FIGS. 20A and B).

Example 7

An in-vitro study was undertaken to prove that mammalian HEp2:NPro cell protection by CBMs (Sp2CBMTD and Vc2CBMTD) from RSV is decreased after cells are treated using neuraminidase.

The experiment was designed by incubating attached HEp2:NPro cells in a 96-well plate with or without neuraminidase for 1 hr at 37° C., 5% $CO_2$, followed by CBMs (100 μg/well) for a further 1 hr, and finally, the addition of RSV (3000 PFU/well) for 1 hr. The plate was then overlaid with AVICEL® (Sigma) medium and left to incubate for 96 hr at 37° C., 5% $CO_2$. RSV-infected cells were determined by evaluating the quantity of RSV that infected the cells using a mouse anti-RSV F antibody (1:200 dilution, MCA490, BioRad) followed by a secondary anti-mouse IgG-HRP antibody (1:2000 dilution, Cell Signalling Technology). Inhibition of RSV infectivity was determined by comparing the absorbance at 450 nm (620 nm as background reference) of neuraminidase-treated versus untreated control wells after reactivity with TMB (substrate for HRP). Replicates n=4, Raw data were analyzed by one-way ANOVA using GraphPad Prism, A p value<0.05 was considered statistically significant (*p<0.05; p<0.01; *p<0.001; ****p<0.0001).

For RSV only control, the result does not show any difference in infectivity between neuraminidase-treated and untreated cells (first two bars on graphs). However, cell protection from both CBMs is decreased after neuraminidase treatment of cells (fourth bar on graphs) but not to the same extent as cells being initially treated by CBMs followed by RSV, this being more evident with Vc2CBMTD. The data suggests that CBMs also protect cells against RSV by targeting cell surface sialic acid (See FIGS. 21A and B).

Example 8

Utility of Engineered Carbohydrate-Binding Module Proteins (Sp2CBMTD and Vc2CBMTD) on RSV-B Infection Using an In Vitro 3D Model of the Human Respiratory Epithelium.

The objective of this study is to evaluate the effect of mCBM40s, Sp2CBMTD and Vc2CBMTD upon RSV replication in a 3D model of the human respiratory epithelium. The assay was performed using MucilAir™, which is a fully differentiated and ready-to-use 3D model of human airway epithelium, constituted with primary human epithelial cells freshly isolated from nasal, tracheal or bronchial biopsies (Epithelix). For infection studies, the RSV-B strain ($10^6$ genome copies/ml RSV, Geneva clinical strain, 2017) was used and applied to the apical side of pre-washed (with PBS) MucilAir inserts on Day 0. For mCBM treatments (n=3), Sp2CBMTD and Vc2CBMTD (at 10 μg or at 100 μg doses) were applied apically either as a single dose one hour before viral infection, or b) as a repeated dose one day and one hour before viral infection. Both regimens had a further exposure of mCBM at 3.5 h post-infection (p.i). Untreated, infected MucilAir (n=2) was used as a control. Apical washes (200 μL) were collected at 3.5 h p.i. and then at 24, 48 and 96 h p.i.

Viral genome copy number was determined using 20 μL of apical wash for viral RNA extraction using the QIAampR Viral RNA kit (Qiagen). Viral RNA was quantified using QuantiTect Probe RT-PCR (Qiagen) using 5 μL of viral RNA and two RSV-B specific primers. Data from readout was corrected for dilution factor and presented as genome copy number per ml. Statistical analysis was performed using Prism 6.0 GraphPad software. Student's unpaired t test was used to compare two sets of data, where *p<0.05.

SUMMARY

Both Sp2CBMTD and Vc2CBMTD were shown to reduce the apical viral load of RSV-infected human airway epithelial cells. The degree of reduction was dependent on the type of mCBM and number of doses administered. Exposure of infected MucilAIr inserts to Sp2CBMTD did not show a significant effect on viral replication due to variability of data but a slight reduction was observed at the highest dose (100 μg) after two doses at 48 h p.i (see FIG. 23A), and after three doses at 96 h p.i. compared to virus infected control. Exposure to Vc2CBMTD (100 μg) was more effective in reducing RSV viral replication in both dosing regimens than using a 10 μg dosing regimen. Although not statistically significant, the reduction of viral load at 48 h p.i was observed to decreased greater than 1 log (FIG. 23B).

The invention claimed is:

1. A method for treating a respiratory syncytial virus (RSV) infection in a subject in need thereof, said method comprising administering to the subject a sialic acid binding molecule, wherein the sialic acid binding molecule comprises one or more family 40 carbohydrate binding modules (CBM40).

2. A method of neutralising or blocking a RSV infection in a subject in need thereof, said method comprising administering to the subject a sialic acid binding molecule, wherein the subject has a RSV infection, and wherein the sialic acid binding molecule comprises one or more family 40 carbohydrate binding modules (CBM40).

3. The method of claim 1, said method comprising mucosally administering a composition comprising the sialic acid binding molecule to the subject in need thereof.

4. The method of claim 1, wherein the sialic acid binding molecule is administered prophylactically to prevent a RSV infection.

5. The method of claim 1, wherein the sialic acid binding molecule does not exhibit sialidase activity.

6. The method of claim 1, wherein the sialic acid binding molecule does not bind heparin or heparin sulfate and/or comprise the GAG-binding domain of a protein that binds heparin or heparin sulfate.

7. The method of claim 1, wherein the sialic acid binding molecule comprises the sialic acid binding domain of *Vibrio cholerae* NanH sialidase and/or the sialic acid binding domain of *Streptococcus pneumoniae* NanA sialidase.

8. The method of claim 7, wherein the *Vibrio cholerae* NanH sialidase comprises the amino acid sequence of SEQ ID NO: 1 or 2.

9. The method of claim 7, wherein the *Streptococcus pneumoniae* NanA sialidase comprises the amino acid sequence of SEQ ID NO: 3 or 4.

10. The method of claim 1, wherein the sialic acid binding molecule is Sp2CBM, Sp2CBMTD, Vc4CBM, Vc2CBM or Vc2CBMTD.

11. The method of claim 1, wherein the sialic acid binding molecule comprising one or more CBM40 comprises one or more modified Family 40 carbohydrate binding modules (CBM40(s)).

12. The method of claim 11, wherein the one or more modified CBM40(s) contain(s) one or more mutations relative to a reference sequence and wherein the reference sequence is selected from the group consisting of:
    (i) a wild type Family 40 CBM sequence;
    (ii) a wild type CBM40 sequences from *Vibrio cholerae*;
    (iii) the NanH sialidase sequence of *Vibrio cholerae*;
    (iv) a wild type CBM40 sequences from *Streptococcus pneumoniae*;
    (v) the NanA sialidase sequence of *Streptococcus pneumoniae*;
    (vi) The sequence of SEQ ID NO: 1;
    (vii) The sequence of SEQ ID NO: 2;
    (viii) The sequence of SEQ ID NO: 3; and
    (ix) The sequence of SEQ ID NO: 4.

13. The method of claim 12, wherein the mutation is selected from the group consisting of:
    (i) one or more amino acid substitution(s);
    (ii) one or more amino acid deletion(s);
    (iii) one or more amino acid addition(s)/insertion(s);
    (iv) one or more amino acid/sequence inversions; and
    (v) one or more amino acid/sequence duplications.

14. The method of claim 11, wherein the sialic acid binding molecule comprises a modified oligomerisation domain.

15. The method of claim 14 wherein the modified oligomerisation domain contains one or more mutations relative to a reference sequence and wherein the reference sequence is selected from the group consisting of:
    (i) a wild type *Pseudomonas aeruginosa* pseudaminidase sequence;
    (ii) the *Pseudomonas aeruginosa* pseudaminidase amino acid sequence deposited under accession number Q9L6G4;
    (iii) the sequence of SEQ ID NO: 5; and
    (iv) the sequence of SEQ ID NO: 6.

16. The method of claim 1, wherein the sialic acid binding molecule comprising one or more CBM40 comprises the following structure:
    CBM1(V239A V246G A162P)--CBM2(V239A V246G A162P)--TD(S342D R403K), wherein CBM1 and CBM 2 are derived from CBM40 sequences and TD is derived from a trimerisation domain.

17. The method of claim 1, wherein sialic acid binding molecule comprising one or more CBM40 comprises the following sequence:

```
                                          (SEQ ID NO: 9)
GAMVIEKEDVETNASNGQRVDLSSELDKLKKLENATVHMEFKPDPKAPAF

YNLFSVSSATKKDEYFTMAVYNNTATLEGRGSDGKQFYNNYNDAPLKVKP

GQWNSVTFTVEKPTAELPKGRARLYVNGGLSRTSLRSGNFIKDMPDVTHV

QIGATKRANNTVWGSNLQIRNLTVYNRALTPEEVQKRSGGGSGVIEKEDV

ETNASNGQRVDLSSELDKLKKLENATVHMEFKPDPKAPAFYNLFSVSSAT

KKDEYFTMAVYNNTATLEGRGSDGKQFYNNYNDAPLKVKPGQWNSVTFTV

EKPTAELPKGRARLYVNGGLSRTSLRSGNFIKDMPDVTHVQIGATKRANN

TVWGSNLQIRNLTVYNRALTPEEVQKRSGGSLGVPDFESDWFDVSSNSLY

TLSHGLQRSPRRVVVEFARSSSPSTWNIVMPSYFNDGGHKGSGAQVEVGS

LNIKLGTGAAVWGTGYFGGIDNSATTRFATGYYRVRAWI.
```

* * * * *

UNITED STATES PATENT AND TRADEMARK OFFICE
CERTIFICATE OF CORRECTION

PATENT NO. : 11,819,534 B2
APPLICATION NO. : 15/733545
DATED : November 21, 2023
INVENTOR(S) : Connaris et al.

It is certified that error appears in the above-identified patent and that said Letters Patent is hereby corrected as shown below:

In the Specification

Column 12, Line 66: Please delete this line and replace with the following:
SpOrig  EKPTAELPKGRVRLYVNGVLSRTSLRSGNFIKDMPDVTHVQIGATKRANNTVWG SNLQIR Column 12, Line 71: Please delete this line and replace with the following:
HEX6 NLTVYNRALTPEEVQKRSGGSLGVPDFESDWFDVSSNSLYTLSHGLQRSPRRVVV EFARS Column 13, SEQ ID NO: 10, Line 1: Please delete this line of the sequence and replace with the following:
GAMALFDYNATGDTEFDSPAKQGWMQDNTNNGSGVLTNADGMPAWLVQGIGGRAQWTYS LSTNQHAQ Column 13, SEQ ID NO: 10, Line 5: Please delete this line of the sequence and replace with the following:
MALFDYNATGDTEFDSPAKQGWMQDNTNNGSGVLTNADGMPAWLVQGIGG Column 14, SEQ ID NO: 11: Please delete the sequence and replace with the following:
GAMALFDYNATGDTEFDSPAKQGWMQDNTNNGSGVLTNADGMPAWLVQGIGGRAQWTYS LSTNQHAQASSFGWRMTTEMKVLSGGMITNYYANGTQRVLPIISLDSSGNLVVEFEGQTGRT VLATGTAATEYHKFELVFLPGSNPSASFYFDGKLIRDNIQPTASKQNMIVWGNGSSNTDGVA AYRDIKFEIQGDALNGSMALFDYNATGDTEFDSPAKQGWMQDNTNNGSGVLTNADGMPAW LVQGIGGRAQWTYSLSTNQHAQASSFGWRMTTEMKVLSGGMITNYYANGTQRVLPIISLDSS GNLVVEFEGQTGRTVLATGTAATEYHKFELVFLPGSNPSASFYFDGKLIRDNIQPTASKQNMI VWGNGSSNTDGVAAYRDIKFEIQGDLQALGMALFDYNATGDTEFDSPAKQGWMQDNTNNG SGVLTNADGMPAWLVQGIGGRAQWTYSLSTNQHAQASSFGWRMTTEMKVLSGGMITNYYA NGTQRVLPIISLDSSGNLVVEFEGQTGRTVLATGTAATEYHKFELVFLPGSNPSASFYFDGKLI RDNIQPTASKQNMIVWGNGSSNTDGVAAYRDIKFEIQGDGGNSGMALFDYNATGDTEFDSPA Signed and Sealed this
Twelfth Day of March, 2024

*Katherine Kelly Vidal*

Katherine Kelly Vidal
*Director of the United States Patent and Trademark Office*

CERTIFICATE OF CORRECTION (continued)
U.S. Pat. No. 11,819,534 B2

KQGWMQDNTNNGSGVLTNADGMPAWLVQGIGGRAQWTYSLSTNQHAQASSFGWRMTTE
MKVLSGGMITNYYANGTQRVLPIISLDSSGNLVVEFEGQTGRTVLATGTAATEYHKFELVFLP
GSNPSASFYFDGKLIRDNIQPTASKQNMIVWGNGSSNTDGVAAYRDIKFEIQGD (SEQ ID NO: 11)

Column 14, Line 63 – Column 15, Line 15: Please delete the sequence and replace with the following:
GSMVIEKEDVETNASNGQRVDLSSELDKLKKLENATVHMEFKPDAKAPAFYNLFSVSSATKK
DEYFTMAVYNNTATLEGRGSDGKQFYNNYNDAPLKVKPGQWNSVTFTVEKPTAELPKGRV
RLYVNGVLSRTSLRSGNFIKDMPDVTHVQIGATKRANNTVWGSNLQIRNLTVYNRALTPEEV
QKRS[xxxxx][xxxxxxxxxx][xxxxxxxxxxxxxxx]GSMVIEKEDVETNASNGQRVDLSSELDKLKKL
ENATVHMEFKPDAKAPAFYNLFSVSSATKKDEYFTMAVYNNTATLEGRGSDGKQFYNNYN
DAPLKVKPGQWNSVTFTVEKPTAELPKGRVRLYVNGVLSRTSLRSGNFIKDMPDVTHVQIGA
TKRANNTVWGSNLQIRNLTVYNRALTPEEVQKRS Column 24, Line 53-66: Please delete the table and replace with the following:

| (*Sp*CBM) variant | Mutations |
|---|---|
| Im28 | M156F/L170T |
| Im29 | M156F/L170T/M185I |
| Im30 | V239A/V246G |
| Im31 | I286A/Y292E |
| Im32 | V239A/V246G/I286A/Y292E |
| Im33 | M156F/L170T/M185I/V239A/V246G/I286A/Y292E |
| (*Pa*TD) variant | Mutation |
| Im34 | S342D/L348D/R403K |

Column 25, Table Sp2CBMTD: Please delete the table and replace with the following:

*Sp*2CBMTD

| variant | Mutations |
|---|---|
| HEX1 | CBM1(L170T V239A V246G I286A Y292E)-CBM2(L170T V239A V246G I286A Y292E)-TD (S342D L348D R403K) |
| HEX2 | CBM1(V239A V246G I286A Y292E)-CBM2(V239A V246G I286A Y292E)- TD (S342D R403K) |
| HEX3 | CBM1(V239A V246G I286A)-CBM2(V239A V246G I286A)-TD (S342D R403K) |
| HEX4 | CBM1(V239A V246G)-CBM2(V239A V246G)-TD (S342D) |
| HEX5 | CBM1(V239A V246G)-CBM2(V239A V246G)-TD(R403K) |
| HEX6 | CBM1(V239A V246G)- CBM2(V239A V246G)-TD (S342D R403K) |
| HEX17 | CBM1(V239A V246G A162P)- CBM2(V239A V246G A162P)-TD (S342D R403K) |

Column 29, Line 17: Please correct "α-2,3-α-2,6-α-2,8-linked" to read --α-2,3- α-2,6- α-2,8-linked--

Column 29, Lines 55-56: Please correct "(*p<0.05; P<0.01;* p<0.001;****p<0.0001)." to read --(*p<0.05;  p<0.01;*p<0.001;****p<0.0001).--

SEQUENCE LISTING

```
<160> NUMBER OF SEQ ID NOS: 31

<210> SEQ ID NO 1
<211> LENGTH: 781
<212> TYPE: PRT
<213> ORGANISM: Vibrio cholerae

<400> SEQUENCE: 1

Met Arg Phe Lys Asn Val Lys Lys Thr Ala Leu Met Leu Ala Met Phe
1               5                   10                  15

Gly Met Ala Thr Ser Ser Asn Ala Ala Leu Phe Asp Tyr Asn Ala Thr
            20                  25                  30

Gly Asp Thr Glu Phe Asp Ser Pro Ala Lys Gln Gly Trp Met Gln Asp
        35                  40                  45

Asn Thr Asn Asn Gly Ser Gly Val Leu Thr Asn Ala Asp Gly Met Pro
    50                  55                  60

Ala Trp Leu Val Gln Gly Ile Gly Gly Arg Ala Gln Trp Thr Tyr Ser
65                  70                  75                  80

Leu Ser Thr Asn Gln His Ala Gln Ala Ser Ser Phe Gly Trp Arg Met
                85                  90                  95

Thr Thr Glu Met Lys Val Leu Ser Gly Gly Met Ile Thr Asn Tyr Tyr
            100                 105                 110

Ala Asn Gly Thr Gln Arg Val Leu Pro Ile Ile Ser Leu Asp Ser Ser
        115                 120                 125

Gly Asn Leu Val Val Glu Phe Glu Gly Gln Thr Gly Arg Thr Val Leu
    130                 135                 140

Ala Thr Gly Thr Ala Ala Thr Glu Tyr His Lys Phe Glu Leu Val Phe
145                 150                 155                 160

Leu Pro Gly Ser Asn Pro Ser Ala Ser Phe Tyr Phe Asp Gly Lys Leu
                165                 170                 175

Ile Arg Asp Asn Ile Gln Pro Thr Ala Ser Lys Gln Asn Met Ile Val
            180                 185                 190

Trp Gly Asn Gly Ser Ser Asn Thr Asp Gly Val Ala Ala Tyr Arg Asp
        195                 200                 205

Ile Lys Phe Glu Ile Gln Gly Asp Val Ile Phe Arg Gly Pro Asp Arg
    210                 215                 220

Ile Pro Ser Ile Val Ala Ser Ser Val Thr Pro Gly Val Val Thr Ala
225                 230                 235                 240

Phe Ala Glu Lys Arg Val Gly Gly Gly Asp Pro Gly Ala Leu Ser Asn
                245                 250                 255

Thr Asn Asp Ile Ile Thr Arg Thr Ser Arg Asp Gly Gly Ile Thr Trp
            260                 265                 270

Asp Thr Glu Leu Asn Leu Thr Glu Gln Ile Asn Val Ser Asp Glu Phe
        275                 280                 285

Asp Phe Ser Asp Pro Arg Pro Ile Tyr Asp Pro Ser Ser Asn Thr Val
    290                 295                 300

Leu Val Ser Tyr Ala Arg Trp Pro Thr Asp Ala Ala Gln Asn Gly Asp
305                 310                 315                 320
```

-continued

```
Arg Ile Lys Pro Trp Met Pro Asn Gly Ile Phe Tyr Ser Val Tyr Asp
                325             330             335
Val Ala Ser Gly Asn Trp Gln Ala Pro Ile Asp Val Thr Asp Gln Val
            340             345             350
Lys Glu Arg Ser Phe Gln Ile Ala Gly Trp Gly Gly Ser Glu Leu Tyr
        355             360             365
Arg Arg Asn Thr Ser Leu Asn Ser Gln Gln Asp Trp Gln Ser Asn Ala
370             375             380
Lys Ile Arg Ile Val Asp Gly Ala Ala Asn Gln Ile Gln Val Ala Asp
385             390             395             400
Gly Ser Arg Lys Tyr Val Val Thr Leu Ser Ile Asp Glu Ser Gly Gly
            405             410             415
Leu Val Ala Asn Leu Asn Gly Val Ser Ala Pro Ile Ile Leu Gln Ser
            420             425             430
Glu His Ala Lys Val His Ser Phe His Asp Tyr Glu Leu Gln Tyr Ser
        435             440             445
Ala Leu Asn His Thr Thr Thr Leu Phe Val Asp Gly Gln Gln Ile Thr
    450             455             460
Thr Trp Ala Gly Glu Val Ser Gln Glu Asn Asn Ile Gln Phe Gly Asn
465             470             475             480
Ala Asp Ala Gln Ile Asp Gly Arg Leu His Val Gln Lys Ile Val Leu
            485             490             495
Thr Gln Gln Gly His Asn Leu Val Glu Phe Asp Ala Phe Tyr Leu Ala
            500             505             510
Gln Gln Thr Pro Glu Val Glu Lys Asp Leu Glu Lys Leu Gly Trp Thr
        515             520             525
Lys Ile Lys Thr Gly Asn Thr Met Ser Leu Tyr Gly Asn Ala Ser Val
    530             535             540
Asn Pro Gly Pro Gly His Gly Ile Thr Leu Thr Arg Gln Gln Asn Ile
545             550             555             560
Ser Gly Ser Gln Asn Gly Arg Leu Ile Tyr Pro Ala Ile Val Leu Asp
            565             570             575
Arg Phe Phe Leu Asn Val Met Ser Ile Tyr Ser Asp Asp Gly Gly Ser
        580             585             590
Asn Trp Gln Thr Gly Ser Thr Leu Pro Ile Pro Phe Arg Trp Lys Ser
    595             600             605
Ser Ser Ile Leu Glu Thr Leu Glu Pro Ser Glu Ala Asp Met Val Glu
610             615             620
Leu Gln Asn Gly Asp Leu Leu Thr Ala Arg Leu Asp Phe Asn Gln
625             630             635             640
Ile Val Asn Gly Val Asn Tyr Ser Pro Arg Gln Gln Phe Leu Ser Lys
            645             650             655
Asp Gly Gly Ile Thr Trp Ser Leu Leu Glu Ala Asn Asn Ala Asn Val
        660             665             670
Phe Ser Asn Ile Ser Thr Gly Thr Val Asp Ala Ser Ile Thr Arg Phe
    675             680             685
Glu Gln Ser Asp Gly Ser His Phe Leu Leu Phe Thr Asn Pro Gln Gly
    690             695             700
Asn Pro Ala Gly Thr Asn Gly Arg Gln Asn Leu Gly Leu Trp Phe Ser
705             710             715             720
Phe Asp Glu Gly Val Thr Trp Lys Gly Pro Ile Gln Leu Val Asn Gly
            725             730             735
Ala Ser Ala Tyr Ser Asp Ile Tyr Gln Leu Asp Ser Glu Asn Ala Ile
```

```
                        740                 745                 750
Val Ile Val Glu Thr Asp Asn Ser Asn Met Arg Ile Leu Arg Met Pro
                755                 760                 765

Ile Thr Leu Leu Lys Gln Lys Leu Thr Leu Ser Gln Asn
        770                 775                 780

<210> SEQ ID NO 2
<211> LENGTH: 176
<212> TYPE: PRT
<213> ORGANISM: Vibrio cholerae

<400> SEQUENCE: 2

Ala Leu Phe Asp Tyr Asn Ala Thr Gly Asp Thr Glu Phe Asp Ser Pro
1               5                   10                  15

Ala Lys Gln Gly Trp Met Gln Asp Asn Thr Asn Asn Gly Ser Gly Val
            20                  25                  30

Leu Thr Asn Ala Asp Gly Met Pro Ala Trp Leu Val Gln Gly Ile Gly
        35                  40                  45

Gly Arg Ala Gln Trp Thr Tyr Ser Leu Ser Thr Asn Gln His Ala Gln
    50                  55                  60

Ala Ser Ser Phe Gly Trp Arg Met Thr Thr Glu Met Lys Val Leu Ser
65                  70                  75                  80

Gly Gly Met Ile Thr Asn Tyr Tyr Ala Asn Gly Thr Gln Arg Val Leu
                85                  90                  95

Pro Ile Ile Ser Leu Asp Ser Ser Gly Asn Leu Val Val Glu Phe Glu
            100                 105                 110

Gly Gln Thr Gly Arg Thr Val Leu Ala Thr Gly Thr Ala Ala Thr Glu
        115                 120                 125

Tyr His Lys Phe Glu Leu Val Phe Leu Pro Gly Ser Asn Pro Ser Ala
    130                 135                 140

Ser Phe Tyr Phe Asp Gly Lys Leu Ile Arg Asp Asn Ile Gln Pro Thr
145                 150                 155                 160

Ala Ser Lys Gln Asn Met Ile Val Trp Gly Asn Gly Ser Ser Asn Thr
                165                 170                 175

<210> SEQ ID NO 3
<211> LENGTH: 1035
<212> TYPE: PRT
<213> ORGANISM: Streptococcus pneumoniae

<400> SEQUENCE: 3

Met Ser Tyr Phe Arg Asn Arg Asp Ile Asp Ile Glu Arg Asn Ser Met
1               5                   10                  15

Asn Arg Ser Val Gln Glu Arg Lys Cys Arg Tyr Ser Ile Arg Lys Leu
            20                  25                  30

Ser Val Gly Ala Val Ser Met Ile Val Gly Ala Val Val Phe Gly Thr
        35                  40                  45

Ser Pro Val Leu Ala Gln Glu Gly Ala Ser Glu Gln Pro Leu Ala Asn
    50                  55                  60

Glu Thr Gln Leu Ser Gly Glu Ser Ser Thr Leu Thr Asp Thr Glu Lys
65                  70                  75                  80

Ser Gln Pro Ser Ser Glu Thr Glu Leu Ser Gly Asn Lys Gln Glu Gln
                85                  90                  95

Glu Arg Lys Asp Lys Gln Glu Glu Lys Ile Pro Arg Asp Tyr Tyr Ala
            100                 105                 110

Arg Asp Leu Glu Asn Val Glu Thr Val Ile Glu Lys Glu Asp Val Glu
```

```
                   115                 120                 125
Thr Asn Ala Ser Asn Gly Gln Arg Val Asp Leu Ser Ser Glu Leu Asp
                130                 135                 140

Lys Leu Lys Lys Leu Glu Asn Ala Thr Val His Met Glu Phe Lys Pro
145                 150                 155                 160

Asp Ala Lys Ala Pro Ala Phe Tyr Asn Leu Phe Ser Val Ser Ser Ala
                165                 170                 175

Thr Lys Lys Asp Glu Tyr Phe Thr Met Ala Val Tyr Asn Asn Thr Ala
                180                 185                 190

Thr Leu Glu Gly Arg Gly Ser Asp Gly Lys Gln Phe Tyr Asn Asn Tyr
                195                 200                 205

Asn Asp Ala Pro Leu Lys Val Lys Pro Gly Gln Trp Asn Ser Val Thr
                210                 215                 220

Phe Thr Val Glu Lys Pro Thr Ala Glu Leu Pro Lys Gly Arg Val Arg
225                 230                 235                 240

Leu Tyr Val Asn Gly Val Leu Ser Arg Thr Ser Leu Arg Ser Gly Asn
                245                 250                 255

Phe Ile Lys Asp Met Pro Asp Val Thr His Val Gln Ile Gly Ala Thr
                260                 265                 270

Lys Arg Ala Asn Asn Thr Val Trp Gly Ser Asn Leu Gln Ile Arg Asn
                275                 280                 285

Leu Thr Val Tyr Asn Arg Ala Leu Thr Pro Glu Glu Val Gln Lys Arg
                290                 295                 300

Ser Gln Leu Phe Lys Arg Ser Asp Leu Glu Lys Lys Leu Pro Glu Gly
305                 310                 315                 320

Ala Ala Leu Thr Glu Lys Thr Asp Ile Phe Glu Ser Gly Arg Asn Gly
                325                 330                 335

Lys Pro Asn Lys Asp Gly Ile Lys Ser Tyr Arg Ile Pro Ala Leu Leu
                340                 345                 350

Lys Thr Asp Lys Gly Thr Leu Ile Ala Gly Ala Asp Glu Arg Arg Leu
                355                 360                 365

His Ser Ser Asp Trp Gly Asp Ile Gly Met Val Ile Arg Arg Ser Glu
                370                 375                 380

Asp Asn Gly Lys Thr Trp Gly Asp Arg Val Thr Ile Thr Asn Leu Arg
385                 390                 395                 400

Asp Asn Pro Lys Ala Ser Asp Pro Ser Ile Gly Ser Pro Val Asn Ile
                405                 410                 415

Asp Met Val Leu Val Gln Asp Pro Glu Thr Lys Arg Ile Phe Ser Ile
                420                 425                 430

Tyr Asp Met Phe Pro Glu Gly Lys Gly Ile Phe Gly Met Ser Ser Gln
                435                 440                 445

Lys Glu Glu Ala Tyr Lys Lys Ile Asp Gly Lys Thr Tyr Gln Ile Leu
                450                 455                 460

Tyr Arg Glu Gly Glu Lys Gly Ala Tyr Thr Ile Arg Glu Asn Gly Thr
465                 470                 475                 480

Val Tyr Thr Pro Asp Gly Lys Ala Thr Asp Tyr Arg Val Val Val Asp
                485                 490                 495

Pro Val Lys Pro Ala Tyr Ser Asp Lys Gly Asp Leu Tyr Lys Gly Asn
                500                 505                 510

Gln Leu Leu Gly Asn Ile Tyr Phe Thr Thr Asn Lys Thr Ser Pro Phe
                515                 520                 525

Arg Ile Ala Lys Asp Ser Tyr Leu Trp Met Ser Tyr Ser Asp Asp Asp
                530                 535                 540
```

```
Gly Lys Thr Trp Ser Ala Pro Gln Asp Ile Thr Pro Met Val Lys Ala
545                 550                 555                 560

Asp Trp Met Lys Phe Leu Gly Val Gly Pro Gly Thr Gly Ile Val Leu
            565                 570                 575

Arg Asn Gly Pro His Lys Gly Arg Ile Leu Ile Pro Val Tyr Thr Thr
            580                 585                 590

Asn Asn Val Ser His Leu Asn Gly Ser Gln Ser Ser Arg Ile Ile Tyr
            595                 600                 605

Ser Asp Asp His Gly Lys Thr Trp His Ala Gly Glu Ala Val Asn Asp
            610                 615                 620

Asn Arg Gln Val Asp Gly Gln Lys Ile His Ser Ser Thr Met Asn Asn
625                 630                 635                 640

Arg Arg Ala Gln Asn Thr Glu Ser Thr Val Val Gln Leu Asn Asn Gly
                645                 650                 655

Asp Val Lys Leu Phe Met Arg Gly Leu Thr Gly Asp Leu Gln Val Ala
            660                 665                 670

Thr Ser Lys Asp Gly Gly Val Thr Trp Glu Lys Asp Ile Lys Arg Tyr
            675                 680                 685

Pro Gln Val Lys Asp Val Tyr Val Gln Met Ser Ala Ile His Thr Met
            690                 695                 700

His Glu Gly Lys Glu Tyr Ile Ile Leu Ser Asn Ala Gly Gly Pro Lys
705                 710                 715                 720

Arg Glu Asn Gly Met Val His Leu Ala Arg Val Glu Glu Asn Gly Glu
                725                 730                 735

Leu Thr Trp Leu Lys His Asn Pro Ile Gln Lys Gly Glu Phe Ala Tyr
            740                 745                 750

Asn Ser Leu Gln Glu Leu Gly Asn Gly Glu Tyr Gly Ile Leu Tyr Glu
            755                 760                 765

His Thr Glu Lys Gly Gln Asn Ala Tyr Thr Leu Ser Phe Arg Lys Phe
            770                 775                 780

Asn Trp Asp Phe Leu Ser Lys Asp Leu Ile Ser Pro Thr Glu Ala Lys
785                 790                 795                 800

Val Lys Arg Thr Arg Glu Met Gly Lys Gly Val Ile Gly Leu Glu Phe
                805                 810                 815

Asp Ser Glu Val Leu Val Asn Lys Ala Pro Thr Leu Gln Leu Ala Asn
            820                 825                 830

Gly Lys Thr Ala Arg Phe Met Thr Gln Tyr Asp Thr Lys Thr Leu Leu
            835                 840                 845

Phe Thr Val Asp Ser Glu Asp Met Gly Gln Lys Val Thr Gly Leu Ala
            850                 855                 860

Glu Gly Ala Ile Glu Ser Met His Asn Leu Pro Val Ser Val Ala Gly
865                 870                 875                 880

Thr Lys Leu Ser Asn Gly Met Asn Gly Ser Glu Ala Ala Val His Glu
                885                 890                 895

Val Pro Glu Tyr Thr Gly Pro Leu Gly Thr Ser Gly Glu Glu Pro Ala
            900                 905                 910

Pro Thr Val Glu Lys Pro Glu Tyr Thr Gly Pro Leu Gly Thr Ser Gly
            915                 920                 925

Glu Glu Pro Ala Pro Thr Val Glu Lys Pro Glu Tyr Thr Gly Pro Leu
930                 935                 940

Gly Thr Ala Gly Glu Glu Ala Ala Pro Thr Val Glu Lys Pro Glu Phe
945                 950                 955                 960
```

```
Thr Gly Gly Val Asn Gly Thr Glu Pro Ala Val His Glu Ile Ala Glu
                    965                 970                 975

Tyr Lys Gly Ser Asp Ser Leu Val Thr Leu Thr Lys Glu Asp Tyr
            980                 985                 990

Thr Tyr Lys Ala Pro Leu Ala Gln Gln Ala Leu Pro Glu Thr Gly Asn
        995                 1000                1005

Lys Glu Ser Asp Leu Leu Ala Ser Leu Gly Leu Thr Ala Phe Phe
    1010                1015                1020

Leu Gly Leu Phe Thr Leu Gly Lys Lys Arg Glu Gln
1025                1030                1035
```

<210> SEQ ID NO 4
<211> LENGTH: 185
<212> TYPE: PRT
<213> ORGANISM: Streptococcus pneumoniae

<400> SEQUENCE: 4

```
Phe Met Arg Gly Leu Thr Gly Asp Leu Gln Val Ala Thr Ser Lys Asp
1               5                   10                  15

Gly Gly Val Thr Trp Glu Lys Asp Ile Lys Arg Tyr Pro Gln Val Lys
            20                  25                  30

Asp Val Tyr Val Gln Met Ser Ala Ile His Thr Met His Glu Gly Lys
        35                  40                  45

Glu Tyr Ile Ile Leu Ser Asn Ala Gly Gly Pro Lys Arg Glu Asn Gly
    50                  55                  60

Met Val His Leu Ala Arg Val Glu Glu Asn Gly Glu Leu Thr Trp Leu
65                  70                  75                  80

Lys His Asn Pro Ile Gln Lys Gly Glu Phe Ala Tyr Asn Ser Leu Gln
                85                  90                  95

Glu Leu Gly Asn Gly Glu Tyr Gly Ile Leu Tyr Glu His Thr Glu Lys
            100                 105                 110

Gly Gln Asn Ala Tyr Thr Leu Ser Phe Arg Lys Phe Asn Trp Asp Phe
        115                 120                 125

Leu Ser Lys Asp Leu Ile Ser Pro Thr Glu Ala Lys Val Lys Arg Thr
    130                 135                 140

Arg Glu Met Gly Lys Gly Val Ile Gly Leu Glu Phe Asp Ser Glu Val
145                 150                 155                 160

Leu Val Asn Lys Ala Pro Thr Leu Gln Leu Ala Asn Gly Lys Thr Ala
                165                 170                 175

Arg Phe Met Thr Gln Tyr Asp Thr Lys
            180                 185
```

<210> SEQ ID NO 5
<211> LENGTH: 438
<212> TYPE: PRT
<213> ORGANISM: Pseudomonas aeruginosa

<400> SEQUENCE: 5

```
Met Asn Thr Tyr Phe Asp Ile Pro His Arg Leu Val Gly Lys Ala Leu
1               5                   10                  15

Tyr Glu Ser Tyr Tyr Asp His Phe Gly Gln Met Asp Ile Leu Ser Asp
            20                  25                  30

Gly Ser Leu Tyr Leu Ile Tyr Arg Arg Ala Thr Glu His Val Gly Gly
        35                  40                  45

Ser Asp Gly Arg Val Val Phe Ser Lys Leu Glu Gly Gly Ile Trp Ser
    50                  55                  60
```

```
Ala Pro Thr Ile Val Ala Gln Ala Gly Gly Gln Asp Phe Arg Asp Val
 65                  70                  75                  80

Ala Gly Gly Thr Met Pro Ser Gly Arg Ile Val Ala Ala Ser Thr Val
                 85                  90                  95

Tyr Glu Thr Gly Glu Val Lys Val Tyr Val Ser Asp Asp Ser Gly Val
            100                 105                 110

Thr Trp Val His Lys Phe Thr Leu Ala Arg Gly Gly Ala Asp Tyr Asn
        115                 120                 125

Phe Ala His Gly Lys Ser Phe Gln Val Gly Ala Arg Tyr Val Ile Pro
    130                 135                 140

Leu Tyr Ala Ala Thr Gly Val Asn Tyr Glu Leu Lys Trp Leu Glu Ser
145                 150                 155                 160

Ser Asp Gly Gly Glu Thr Trp Gly Gly Ser Thr Ile Tyr Ser Gly
                165                 170                 175

Asn Thr Pro Tyr Asn Glu Thr Ser Tyr Leu Pro Val Gly Asp Gly Val
            180                 185                 190

Ile Leu Ala Val Ala Arg Val Gly Ser Gly Ala Gly Gly Ala Leu Arg
        195                 200                 205

Gln Phe Ile Ser Leu Asp Asp Gly Gly Thr Trp Thr Asp Gln Gly Asn
    210                 215                 220

Val Thr Ala Gln Asn Gly Asp Ser Thr Asp Ile Leu Val Ala Pro Ser
225                 230                 235                 240

Leu Ser Tyr Ile Tyr Ser Glu Gly Gly Thr Pro His Val Val Leu Leu
                245                 250                 255

Tyr Thr Asn Arg Thr Thr His Phe Cys Tyr Tyr Arg Thr Ile Leu Leu
            260                 265                 270

Ala Lys Ala Val Ala Gly Ser Ser Gly Trp Thr Glu Arg Val Pro Val
        275                 280                 285

Tyr Ser Ala Pro Ala Ala Ser Gly Tyr Thr Ser Gln Val Val Leu Gly
    290                 295                 300

Gly Arg Arg Ile Leu Gly Asn Leu Phe Arg Glu Thr Ser Ser Thr Thr
305                 310                 315                 320

Ser Gly Ala Tyr Gln Phe Glu Val Tyr Leu Gly Gly Val Pro Asp Phe
                325                 330                 335

Glu Ser Asp Trp Phe Ser Val Ser Ser Asn Ser Leu Tyr Thr Leu Ser
            340                 345                 350

His Gly Leu Gln Arg Ser Pro Arg Arg Val Val Glu Phe Ala Arg
        355                 360                 365

Ser Ser Ser Pro Ser Thr Trp Asn Ile Val Met Pro Ser Tyr Phe Asn
370                 375                 380

Asp Gly Gly His Lys Gly Ser Gly Ala Gln Val Glu Val Gly Ser Leu
385                 390                 395                 400

Asn Ile Arg Leu Gly Thr Gly Ala Ala Val Trp Gly Thr Gly Tyr Phe
            405                 410                 415

Gly Gly Ile Asp Asn Ser Ala Thr Thr Arg Phe Ala Thr Gly Tyr Tyr
        420                 425                 430

Arg Val Arg Ala Trp Ile
        435

<210> SEQ ID NO 6
<211> LENGTH: 106
<212> TYPE: PRT
<213> ORGANISM: Pseudomonas aeruginosa

<400> SEQUENCE: 6
```

```
Val Pro Asp Phe Glu Ser Asp Trp Phe Ser Val Ser Ser Asn Ser Leu
1               5                   10                  15

Tyr Thr Leu Ser His Gly Leu Gln Arg Ser Pro Arg Arg Val Val Val
            20                  25                  30

Glu Phe Ala Arg Ser Ser Pro Ser Thr Trp Asn Ile Val Met Pro
            35                  40                  45

Ser Tyr Phe Asn Asp Gly Gly His Lys Gly Ser Gly Ala Gln Val Glu
50                  55                  60

Val Gly Ser Leu Asn Ile Arg Leu Gly Thr Gly Ala Ala Val Trp Gly
65                  70                  75                  80

Thr Gly Tyr Phe Gly Gly Ile Asp Asn Ser Ala Thr Thr Arg Phe Ala
                85                  90                  95

Thr Gly Tyr Tyr Arg Val Arg Ala Trp Ile
                100                 105
```

<210> SEQ ID NO 7
<211> LENGTH: 489
<212> TYPE: PRT
<213> ORGANISM: Streptococcus pneumoniae

<400> SEQUENCE: 7

```
Gly Ala Met Val Ile Glu Lys Glu Asp Val Glu Thr Asn Ala Ser Asn
1               5                   10                  15

Gly Gln Arg Val Asp Leu Ser Ser Glu Leu Asp Lys Leu Lys Lys Leu
            20                  25                  30

Glu Asn Ala Thr Val His Met Glu Phe Lys Pro Asp Ala Lys Ala Pro
            35                  40                  45

Ala Phe Tyr Asn Leu Phe Ser Val Ser Ser Ala Thr Lys Lys Asp Glu
50                  55                  60

Tyr Phe Thr Met Ala Val Tyr Asn Asn Thr Ala Thr Leu Glu Gly Arg
65                  70                  75                  80

Gly Ser Asp Gly Lys Gln Phe Tyr Asn Tyr Asn Asp Ala Pro Leu
                85                  90                  95

Lys Val Lys Pro Gly Gln Trp Asn Ser Val Thr Phe Thr Val Glu Lys
            100                 105                 110

Pro Thr Ala Glu Leu Pro Lys Gly Arg Val Arg Leu Tyr Val Asn Gly
            115                 120                 125

Val Leu Ser Arg Thr Ser Leu Arg Ser Gly Asn Phe Ile Lys Asp Met
130                 135                 140

Pro Asp Val Thr His Val Gln Ile Gly Ala Thr Lys Arg Ala Asn Asn
145                 150                 155                 160

Thr Val Trp Gly Ser Asn Leu Gln Ile Arg Asn Leu Thr Val Tyr Asn
            165                 170                 175

Arg Ala Leu Thr Pro Glu Glu Val Gln Lys Arg Ser Gly Gly Gly Ser
            180                 185                 190

Gly Val Ile Glu Lys Glu Asp Val Glu Thr Asn Ala Ser Asn Gly Gln
            195                 200                 205

Arg Val Asp Leu Ser Ser Glu Leu Asp Lys Leu Lys Lys Leu Glu Asn
            210                 215                 220

Ala Thr Val His Met Glu Phe Lys Pro Asp Ala Lys Ala Pro Ala Phe
225                 230                 235                 240

Tyr Asn Leu Phe Ser Val Ser Ser Ala Thr Lys Lys Asp Glu Tyr Phe
            245                 250                 255

Thr Met Ala Val Tyr Asn Asn Thr Ala Thr Leu Glu Gly Arg Gly Ser
```

```
                260                 265                 270
Asp Gly Lys Gln Phe Tyr Asn Asn Tyr Asn Asp Ala Pro Leu Lys Val
            275                 280                 285

Lys Pro Gly Gln Trp Asn Ser Val Thr Phe Thr Val Glu Lys Pro Thr
        290                 295                 300

Ala Glu Leu Pro Lys Gly Arg Val Arg Leu Tyr Val Asn Gly Val Leu
305                 310                 315                 320

Ser Arg Thr Ser Leu Arg Ser Gly Asn Phe Ile Lys Asp Met Pro Asp
                325                 330                 335

Val Thr His Val Gln Ile Gly Ala Thr Lys Arg Ala Asn Asn Thr Val
            340                 345                 350

Trp Gly Ser Asn Leu Gln Ile Arg Asn Leu Thr Val Tyr Asn Arg Ala
        355                 360                 365

Leu Thr Pro Glu Glu Val Gln Lys Arg Ser Gly Gly Ala Leu Gly Val
    370                 375                 380

Pro Asp Phe Glu Ser Asp Trp Phe Ser Val Ser Ser Asn Ser Leu Tyr
385                 390                 395                 400

Thr Leu Ser His Gly Leu Gln Arg Ser Pro Arg Arg Val Val Val Glu
                405                 410                 415

Phe Ala Arg Ser Ser Pro Ser Thr Trp Asn Ile Val Met Pro Ser
            420                 425                 430

Tyr Phe Asn Asp Gly Gly His Lys Gly Ser Gly Ala Gln Val Glu Val
        435                 440                 445

Gly Ser Leu Asn Ile Arg Leu Gly Thr Gly Ala Val Trp Gly Thr
450                 455                 460

Gly Tyr Phe Gly Gly Ile Asp Asn Ser Ala Thr Thr Arg Phe Ala Thr
465                 470                 475                 480

Gly Tyr Tyr Arg Val Arg Ala Trp Ile
                485

<210> SEQ ID NO 8
<211> LENGTH: 489
<212> TYPE: PRT
<213> ORGANISM: Artificial Sequence
<220> FEATURE:
<223> OTHER INFORMATION: Modified CBM

<400> SEQUENCE: 8

Gly Ala Met Val Ile Glu Lys Glu Asp Val Glu Thr Asn Ala Ser Asn
1               5                   10                  15

Gly Gln Arg Val Asp Leu Ser Ser Glu Leu Asp Lys Leu Lys Lys Leu
            20                  25                  30

Glu Asn Ala Thr Val His Met Glu Phe Lys Pro Asp Ala Lys Ala Pro
        35                  40                  45

Ala Phe Tyr Asn Leu Phe Ser Val Ser Ala Thr Lys Lys Asp Glu
    50                  55                  60

Tyr Phe Thr Met Ala Val Tyr Asn Asn Thr Ala Thr Leu Glu Gly Arg
65                  70                  75                  80

Gly Ser Asp Gly Lys Gln Phe Tyr Asn Tyr Asn Asp Ala Pro Leu
                85                  90                  95

Lys Val Lys Pro Gly Gln Trp Asn Ser Val Thr Phe Thr Val Glu Lys
            100                 105                 110

Pro Thr Ala Glu Leu Pro Lys Gly Arg Ala Arg Leu Tyr Val Asn Gly
        115                 120                 125

Gly Leu Ser Arg Thr Ser Leu Arg Ser Gly Asn Phe Ile Lys Asp Met
```

```
                130                 135                 140
Pro Asp Val Thr His Val Gln Ile Gly Ala Thr Lys Arg Ala Asn Asn
145                 150                 155                 160

Thr Val Trp Gly Ser Asn Leu Gln Ile Arg Asn Leu Thr Val Tyr Asn
                165                 170                 175

Arg Ala Leu Thr Pro Glu Glu Val Gln Lys Arg Ser Gly Gly Gly Ser
            180                 185                 190

Gly Val Ile Glu Lys Glu Asp Val Glu Thr Asn Ala Ser Asn Gly Gln
            195                 200                 205

Arg Val Asp Leu Ser Ser Glu Leu Asp Lys Leu Lys Lys Leu Glu Asn
210                 215                 220

Ala Thr Val His Met Glu Phe Lys Pro Asp Ala Lys Ala Pro Ala Phe
225                 230                 235                 240

Tyr Asn Leu Phe Ser Val Ser Ala Thr Lys Lys Asp Glu Tyr Phe
                245                 250                 255

Thr Met Ala Val Tyr Asn Asn Thr Ala Thr Leu Glu Gly Arg Gly Ser
            260                 265                 270

Asp Gly Lys Gln Phe Tyr Asn Asn Tyr Asn Asp Ala Pro Leu Lys Val
            275                 280                 285

Lys Pro Gly Gln Trp Asn Ser Val Thr Phe Thr Val Glu Lys Pro Thr
        290                 295                 300

Ala Glu Leu Pro Lys Gly Arg Ala Arg Leu Tyr Val Asn Gly Gly Leu
305                 310                 315                 320

Ser Arg Thr Ser Leu Arg Ser Gly Asn Phe Ile Lys Asp Met Pro Asp
                325                 330                 335

Val Thr His Val Gln Ile Gly Ala Thr Lys Arg Ala Asn Asn Thr Val
            340                 345                 350

Trp Gly Ser Asn Leu Gln Ile Arg Asn Leu Thr Val Tyr Asn Arg Ala
        355                 360                 365

Leu Thr Pro Glu Glu Val Gln Lys Arg Ser Gly Gly Ser Leu Gly Val
        370                 375                 380

Pro Asp Phe Glu Ser Asp Trp Phe Asp Val Ser Ser Asn Ser Leu Tyr
385                 390                 395                 400

Thr Leu Ser His Gly Leu Gln Arg Ser Pro Arg Val Val Val Glu
                405                 410                 415

Phe Ala Arg Ser Ser Ser Pro Ser Thr Trp Asn Ile Val Met Pro Ser
            420                 425                 430

Tyr Phe Asn Asp Gly His Lys Gly Ser Gly Ala Gln Val Glu Val
            435                 440                 445

Gly Ser Leu Asn Ile Lys Leu Gly Thr Gly Ala Ala Val Trp Gly Thr
    450                 455                 460

Gly Tyr Phe Gly Gly Ile Asp Asn Ser Ala Thr Thr Arg Phe Ala Thr
465                 470                 475                 480

Gly Tyr Tyr Arg Val Arg Ala Trp Ile
                485

<210> SEQ ID NO 9
<211> LENGTH: 489
<212> TYPE: PRT
<213> ORGANISM: Artificial Sequence
<220> FEATURE:
<223> OTHER INFORMATION: Modified CBM

<400> SEQUENCE: 9

Gly Ala Met Val Ile Glu Lys Glu Asp Val Glu Thr Asn Ala Ser Asn
```

-continued

```
1               5                   10                  15
Gly Gln Arg Val Asp Leu Ser Ser Glu Leu Asp Lys Leu Lys Lys Leu
            20                  25                  30
Glu Asn Ala Thr Val His Met Glu Phe Lys Pro Asp Pro Lys Ala Pro
            35                  40                  45
Ala Phe Tyr Asn Leu Phe Ser Val Ser Ser Ala Thr Lys Lys Asp Glu
 50                  55                  60
Tyr Phe Thr Met Ala Val Tyr Asn Asn Thr Ala Thr Leu Glu Gly Arg
 65                  70                  75                  80
Gly Ser Asp Gly Lys Gln Phe Tyr Asn Tyr Asn Asp Ala Pro Leu
                85                  90                  95
Lys Val Lys Pro Gly Gln Trp Asn Ser Val Thr Phe Thr Val Glu Lys
            100                 105                 110
Pro Thr Ala Glu Leu Pro Lys Gly Arg Ala Arg Leu Tyr Val Asn Gly
            115                 120                 125
Gly Leu Ser Arg Thr Ser Leu Arg Ser Gly Asn Phe Ile Lys Asp Met
 130                 135                 140
Pro Asp Val Thr His Val Gln Ile Gly Ala Thr Lys Arg Ala Asn Asn
 145                 150                 155                 160
Thr Val Trp Gly Ser Asn Leu Gln Ile Arg Asn Leu Thr Val Tyr Asn
                165                 170                 175
Arg Ala Leu Thr Pro Glu Glu Val Gln Lys Arg Ser Gly Gly Gly Ser
            180                 185                 190
Gly Val Ile Glu Lys Glu Asp Val Glu Thr Asn Ala Ser Asn Gly Gln
            195                 200                 205
Arg Val Asp Leu Ser Ser Glu Leu Asp Lys Leu Lys Lys Leu Glu Asn
 210                 215                 220
Ala Thr Val His Met Glu Phe Lys Pro Asp Pro Lys Ala Pro Ala Phe
 225                 230                 235                 240
Tyr Asn Leu Phe Ser Val Ser Ser Ala Thr Lys Lys Asp Glu Tyr Phe
                245                 250                 255
Thr Met Ala Val Tyr Asn Asn Thr Ala Thr Leu Glu Gly Arg Gly Ser
            260                 265                 270
Asp Gly Lys Gln Phe Tyr Asn Tyr Asn Asp Ala Pro Leu Lys Val
            275                 280                 285
Lys Pro Gly Gln Trp Asn Ser Val Thr Phe Thr Val Glu Lys Pro Thr
 290                 295                 300
Ala Glu Leu Pro Lys Gly Arg Ala Arg Leu Tyr Val Asn Gly Gly Leu
 305                 310                 315                 320
Ser Arg Thr Ser Leu Arg Ser Gly Asn Phe Ile Lys Asp Met Pro Asp
                325                 330                 335
Val Thr His Val Gln Ile Gly Ala Thr Lys Arg Ala Asn Asn Thr Val
            340                 345                 350
Trp Gly Ser Asn Leu Gln Ile Arg Asn Leu Thr Val Tyr Asn Arg Ala
            355                 360                 365
Leu Thr Pro Glu Glu Val Gln Lys Arg Ser Gly Gly Ser Leu Gly Val
            370                 375                 380
Pro Asp Phe Glu Ser Asp Trp Phe Asp Val Ser Ser Asn Ser Leu Tyr
 385                 390                 395                 400
Thr Leu Ser His Gly Leu Gln Arg Ser Pro Arg Arg Val Val Glu
                405                 410                 415
Phe Ala Arg Ser Ser Ser Pro Ser Thr Trp Asn Ile Val Met Pro Ser
            420                 425                 430
```

```
Tyr Phe Asn Asp Gly Gly His Lys Gly Ser Gly Ala Gln Val Glu Val
            435                 440                 445

Gly Ser Leu Asn Ile Lys Leu Gly Thr Gly Ala Ala Val Trp Gly Thr
450                 455                 460

Gly Tyr Phe Gly Gly Ile Asp Asn Ser Ala Thr Thr Arg Phe Ala Thr
465                 470                 475                 480

Gly Tyr Tyr Arg Val Arg Ala Trp Ile
                485

<210> SEQ ID NO 10
<211> LENGTH: 393
<212> TYPE: PRT
<213> ORGANISM: Artificial Sequence
<220> FEATURE:
<223> OTHER INFORMATION: Vc2CBM

<400> SEQUENCE: 10

Gly Ala Met Ala Leu Phe Asp Tyr Asn Ala Thr Gly Asp Thr Glu Phe
1               5                   10                  15

Asp Ser Pro Ala Lys Gln Gly Trp Met Gln Asp Asn Thr Asn Asn Gly
            20                  25                  30

Ser Gly Val Leu Thr Asn Ala Asp Gly Met Pro Ala Trp Leu Val Gln
        35                  40                  45

Gly Ile Gly Gly Arg Ala Gln Trp Thr Tyr Ser Leu Ser Thr Asn Gln
    50                  55                  60

His Ala Gln Ala Ser Ser Phe Gly Trp Arg Met Thr Thr Glu Met Lys
65                  70                  75                  80

Val Leu Ser Gly Gly Met Ile Thr Asn Tyr Tyr Ala Asn Gly Thr Gln
                85                  90                  95

Arg Val Leu Pro Ile Ile Ser Leu Asp Ser Ser Gly Asn Leu Val Val
            100                 105                 110

Glu Phe Glu Gly Gln Thr Gly Arg Thr Val Leu Ala Thr Gly Thr Ala
        115                 120                 125

Ala Thr Glu Tyr His Lys Phe Glu Leu Val Phe Leu Pro Gly Ser Asn
    130                 135                 140

Pro Ser Ala Ser Phe Tyr Phe Asp Gly Lys Leu Ile Arg Asp Asn Ile
145                 150                 155                 160

Gln Pro Thr Ala Ser Lys Gln Asn Met Ile Val Trp Gly Asn Gly Ser
                165                 170                 175

Ser Asn Thr Asp Gly Val Ala Ala Tyr Arg Asp Ile Lys Phe Glu Ile
            180                 185                 190

Gln Gly Asp Ala Leu Asn Gly Ser Met Ala Leu Phe Asp Tyr Asn Ala
        195                 200                 205

Thr Gly Asp Thr Glu Phe Asp Ser Pro Ala Lys Gln Gly Trp Met Gln
    210                 215                 220

Asp Asn Thr Asn Asn Gly Ser Gly Val Leu Thr Asn Ala Asp Gly Met
225                 230                 235                 240

Pro Ala Trp Leu Val Gln Gly Ile Gly Gly Arg Ala Gln Trp Thr Tyr
                245                 250                 255

Ser Leu Ser Thr Asn Gln His Ala Gln Ala Ser Ser Phe Gly Trp Arg
            260                 265                 270

Met Thr Thr Glu Met Lys Val Leu Ser Gly Gly Met Ile Thr Asn Tyr
        275                 280                 285

Tyr Ala Asn Gly Thr Gln Arg Val Leu Pro Ile Ile Ser Leu Asp Ser
    290                 295                 300
```

Ser Gly Asn Leu Val Val Glu Phe Glu Gly Gln Thr Gly Arg Thr Val
305                 310                 315                 320

Leu Ala Thr Gly Thr Ala Ala Thr Glu Tyr His Lys Phe Glu Leu Val
                325                 330                 335

Phe Leu Pro Gly Ser Asn Pro Ser Ala Ser Phe Tyr Phe Asp Gly Lys
            340                 345                 350

Leu Ile Arg Asp Asn Ile Gln Pro Thr Ala Ser Lys Gln Asn Met Ile
        355                 360                 365

Val Trp Gly Asn Gly Ser Ser Asn Thr Asp Gly Val Ala Ala Tyr Arg
    370                 375                 380

Asp Ile Lys Phe Glu Ile Gln Gly Asp
385                 390

<210> SEQ ID NO 11
<211> LENGTH: 789
<212> TYPE: PRT
<213> ORGANISM: Artificial Sequence
<220> FEATURE:
<223> OTHER INFORMATION: Vc4CBM

<400> SEQUENCE: 11

Gly Ala Met Ala Leu Phe Asp Tyr Asn Ala Thr Gly Asp Thr Glu Phe
1               5                   10                  15

Asp Ser Pro Ala Lys Gln Gly Trp Met Gln Asp Asn Thr Asn Asn Gly
            20                  25                  30

Ser Gly Val Leu Thr Asn Ala Asp Gly Met Pro Ala Trp Leu Val Gln
        35                  40                  45

Gly Ile Gly Gly Arg Ala Gln Trp Thr Tyr Ser Leu Ser Thr Asn Gln
    50                  55                  60

His Ala Gln Ala Ser Ser Phe Gly Trp Arg Met Thr Thr Glu Met Lys
65                  70                  75                  80

Val Leu Ser Gly Gly Met Ile Thr Asn Tyr Tyr Ala Asn Gly Thr Gln
                85                  90                  95

Arg Val Leu Pro Ile Ile Ser Leu Asp Ser Ser Gly Asn Leu Val Val
            100                 105                 110

Glu Phe Glu Gly Gln Thr Gly Arg Thr Val Leu Ala Thr Gly Thr Ala
        115                 120                 125

Ala Thr Glu Tyr His Lys Phe Glu Leu Val Phe Leu Pro Gly Ser Asn
    130                 135                 140

Pro Ser Ala Ser Phe Tyr Phe Asp Gly Lys Leu Ile Arg Asp Asn Ile
145                 150                 155                 160

Gln Pro Thr Ala Ser Lys Gln Asn Met Ile Val Trp Gly Asn Gly Ser
                165                 170                 175

Ser Asn Thr Asp Gly Val Ala Ala Tyr Arg Asp Ile Lys Phe Glu Ile
            180                 185                 190

Gln Gly Asp Ala Leu Asn Gly Ser Met Ala Leu Phe Asp Tyr Asn Ala
        195                 200                 205

Thr Gly Asp Thr Glu Phe Asp Ser Pro Ala Lys Gln Gly Trp Met Gln
    210                 215                 220

Asp Asn Thr Asn Asn Gly Ser Gly Val Leu Thr Asn Ala Asp Gly Met
225                 230                 235                 240

Pro Ala Trp Leu Val Gln Gly Ile Gly Gly Arg Ala Gln Trp Thr Tyr
                245                 250                 255

Ser Leu Ser Thr Asn Gln His Ala Gln Ala Ser Ser Phe Gly Trp Arg
            260                 265                 270

```
Met Thr Thr Glu Met Lys Val Leu Ser Gly Gly Met Ile Thr Asn Tyr
            275                 280                 285
Tyr Ala Asn Gly Thr Gln Arg Val Leu Pro Ile Ile Ser Leu Asp Ser
        290                 295                 300
Ser Gly Asn Leu Val Val Glu Phe Glu Gly Gln Thr Gly Arg Thr Val
305                 310                 315                 320
Leu Ala Thr Gly Thr Ala Ala Thr Glu Tyr His Lys Phe Glu Leu Val
                325                 330                 335
Phe Leu Pro Gly Ser Asn Pro Ser Ala Ser Phe Tyr Phe Asp Gly Lys
            340                 345                 350
Leu Ile Arg Asp Asn Ile Gln Pro Thr Ala Ser Lys Gln Asn Met Ile
            355                 360                 365
Val Trp Gly Asn Gly Ser Ser Asn Thr Asp Gly Val Ala Ala Tyr Arg
        370                 375                 380
Asp Ile Lys Phe Glu Ile Gln Gly Asp Leu Gln Ala Leu Gly Met Ala
385                 390                 395                 400
Leu Phe Asp Tyr Asn Ala Thr Gly Asp Thr Glu Phe Asp Ser Pro Ala
                405                 410                 415
Lys Gln Gly Trp Met Gln Asp Asn Thr Asn Gly Ser Gly Val Leu
            420                 425                 430
Thr Asn Ala Asp Gly Met Pro Ala Trp Leu Val Gln Gly Ile Gly Gly
            435                 440                 445
Arg Ala Gln Trp Thr Tyr Ser Leu Ser Thr Asn Gln His Ala Gln Ala
        450                 455                 460
Ser Ser Phe Gly Trp Arg Met Thr Thr Glu Met Lys Val Leu Ser Gly
465                 470                 475                 480
Gly Met Ile Thr Asn Tyr Tyr Ala Asn Gly Thr Gln Arg Val Leu Pro
                485                 490                 495
Ile Ile Ser Leu Asp Ser Ser Gly Asn Leu Val Val Glu Phe Glu Gly
            500                 505                 510
Gln Thr Gly Arg Thr Val Leu Ala Thr Gly Thr Ala Ala Thr Glu Tyr
            515                 520                 525
His Lys Phe Glu Leu Val Phe Leu Pro Gly Ser Asn Pro Ser Ala Ser
        530                 535                 540
Phe Tyr Phe Asp Gly Lys Leu Ile Arg Asp Asn Ile Gln Pro Thr Ala
545                 550                 555                 560
Ser Lys Gln Asn Met Ile Val Trp Gly Asn Gly Ser Ser Asn Thr Asp
                565                 570                 575
Gly Val Ala Ala Tyr Arg Asp Ile Lys Phe Glu Ile Gln Gly Asp Gly
            580                 585                 590
Gly Asn Ser Gly Met Ala Leu Phe Asp Tyr Asn Ala Thr Gly Asp Thr
            595                 600                 605
Glu Phe Asp Ser Pro Ala Lys Gln Gly Trp Met Gln Asp Asn Thr Asn
        610                 615                 620
Asn Gly Ser Gly Val Leu Thr Asn Ala Asp Gly Met Pro Ala Trp Leu
625                 630                 635                 640
Val Gln Gly Ile Gly Gly Arg Ala Gln Trp Thr Tyr Ser Leu Ser Thr
                645                 650                 655
Asn Gln His Ala Gln Ala Ser Ser Phe Gly Trp Arg Met Thr Thr Glu
            660                 665                 670
Met Lys Val Leu Ser Gly Gly Met Ile Thr Asn Tyr Tyr Ala Asn Gly
            675                 680                 685
```

```
Thr Gln Arg Val Leu Pro Ile Ile Ser Leu Asp Ser Ser Gly Asn Leu
    690                 695                 700

Val Val Glu Phe Glu Gly Gln Thr Gly Arg Thr Val Leu Ala Thr Gly
705                 710                 715                 720

Thr Ala Ala Thr Glu Tyr His Lys Phe Glu Leu Val Phe Leu Pro Gly
                725                 730                 735

Ser Asn Pro Ser Ala Ser Phe Tyr Phe Asp Gly Lys Leu Ile Arg Asp
            740                 745                 750

Asn Ile Gln Pro Thr Ala Ser Lys Gln Asn Met Ile Val Trp Gly Asn
        755                 760                 765

Gly Ser Ser Asn Thr Asp Gly Val Ala Ala Tyr Arg Asp Ile Lys Phe
770                 775                 780

Glu Ile Gln Gly Asp
785

<210> SEQ ID NO 12
<211> LENGTH: 188
<212> TYPE: PRT
<213> ORGANISM: Streptococcus pneumoniae

<400> SEQUENCE: 12

Gly Ser Met Val Ile Glu Lys Glu Asp Val Glu Thr Asn Ala Ser Asn
1               5                   10                  15

Gly Gln Arg Val Asp Leu Ser Ser Glu Leu Asp Lys Leu Lys Lys Leu
            20                  25                  30

Glu Asn Ala Thr Val His Met Glu Phe Lys Pro Asp Ala Lys Ala Pro
        35                  40                  45

Ala Phe Tyr Asn Leu Phe Ser Val Ser Ala Thr Lys Lys Asp Glu
    50                  55                  60

Tyr Phe Thr Met Ala Val Tyr Asn Asn Thr Ala Thr Leu Glu Gly Arg
65                  70                  75                  80

Gly Ser Asp Gly Lys Gln Phe Tyr Asn Tyr Asn Asp Ala Pro Leu
            85                  90                  95

Lys Val Lys Pro Gly Gln Trp Asn Ser Val Thr Phe Thr Val Glu Lys
        100                 105                 110

Pro Thr Ala Glu Leu Pro Lys Gly Arg Val Arg Leu Tyr Val Asn Gly
    115                 120                 125

Val Leu Ser Arg Thr Ser Leu Arg Ser Gly Asn Phe Ile Lys Asp Met
130                 135                 140

Pro Asp Val Thr His Val Gln Ile Gly Ala Thr Lys Arg Ala Asn Asn
145                 150                 155                 160

Thr Val Trp Gly Ser Asn Leu Gln Ile Arg Asn Leu Thr Val Tyr Asn
                165                 170                 175

Arg Ala Leu Thr Pro Glu Glu Val Gln Lys Arg Ser
            180                 185

<210> SEQ ID NO 13
<211> LENGTH: 5
<212> TYPE: PRT
<213> ORGANISM: Artificial Sequence
<220> FEATURE:
<223> OTHER INFORMATION: Peptide linker
<220> FEATURE:
<221> NAME/KEY: MISC_FEATURE
<222> LOCATION: (3)..(3)
<223> OTHER INFORMATION: x = any amino acid

<400> SEQUENCE: 13
```

```
Ala Leu Xaa Gly Ser
1               5

<210> SEQ ID NO 14
<211> LENGTH: 5
<212> TYPE: PRT
<213> ORGANISM: Artificial Sequence
<220> FEATURE:
<223> OTHER INFORMATION: Peptide linker

<400> SEQUENCE: 14

Leu Gln Ala Leu Gly
1               5

<210> SEQ ID NO 15
<211> LENGTH: 5
<212> TYPE: PRT
<213> ORGANISM: Artificial Sequence
<220> FEATURE:
<223> OTHER INFORMATION: Peptide linker
<220> FEATURE:
<221> NAME/KEY: MISC_FEATURE
<222> LOCATION: (3)..(3)
<223> OTHER INFORMATION: x = any amino acid

<400> SEQUENCE: 15

Gly Gly Xaa Ser Gly
1               5

<210> SEQ ID NO 16
<211> LENGTH: 5
<212> TYPE: PRT
<213> ORGANISM: Artificial Sequence
<220> FEATURE:
<223> OTHER INFORMATION: Peptide linker

<400> SEQUENCE: 16

Gly Gly Ala Leu Gly
1               5

<210> SEQ ID NO 17
<211> LENGTH: 5
<212> TYPE: PRT
<213> ORGANISM: Artificial Sequence
<220> FEATURE:
<223> OTHER INFORMATION: Peptide linker

<400> SEQUENCE: 17

Gly Gly Gly Gly Ser
1               5

<210> SEQ ID NO 18
<211> LENGTH: 10
<212> TYPE: PRT
<213> ORGANISM: Artificial Sequence
<220> FEATURE:
<223> OTHER INFORMATION: Peptide linker
<220> FEATURE:
<221> NAME/KEY: MISC_FEATURE
<222> LOCATION: (3)..(3)
<223> OTHER INFORMATION: x = any amino acid

<400> SEQUENCE: 18

Ala Leu Xaa Gly Ser Gly Gly Ser Gly
1               5                   10

<210> SEQ ID NO 19
<211> LENGTH: 10
```

```
<212> TYPE: PRT
<213> ORGANISM: Artificial Sequence
<220> FEATURE:
<223> OTHER INFORMATION: Peptide linker

<400> SEQUENCE: 19

Leu Gln Ala Leu Gly Gly Gly Gly Ser Leu
1               5                   10

<210> SEQ ID NO 20
<211> LENGTH: 15
<212> TYPE: PRT
<213> ORGANISM: Artificial Sequence
<220> FEATURE:
<223> OTHER INFORMATION: Peptide linker
<220> FEATURE:
<221> NAME/KEY: MISC_FEATURE
<222> LOCATION: (3)..(3)
<223> OTHER INFORMATION: X = any amino acid

<400> SEQUENCE: 20

Ala Leu Xaa Gly Ser Gly Gly Gly Ser Gly Gly Gly Gly Ser Gly
1               5                   10                  15

<210> SEQ ID NO 21
<211> LENGTH: 10
<212> TYPE: PRT
<213> ORGANISM: Streptococcus pneumoniae

<400> SEQUENCE: 21

Gly Val Leu Ser Arg Thr Ser Leu Arg Ser
1               5                   10

<210> SEQ ID NO 22
<211> LENGTH: 10
<212> TYPE: PRT
<213> ORGANISM: Pseudomonas aeruginosa

<400> SEQUENCE: 22

Trp Phe Ser Val Ser Ser Asn Ser Leu Tyr
1               5                   10

<210> SEQ ID NO 23
<211> LENGTH: 9
<212> TYPE: PRT
<213> ORGANISM: Pseudomonas aeruginosa

<400> SEQUENCE: 23

Leu Ser His Gly Leu Gln Arg Ser Pro
1               5

<210> SEQ ID NO 24
<211> LENGTH: 9
<212> TYPE: PRT
<213> ORGANISM: Pseudomonas aeruginosa

<400> SEQUENCE: 24

Gly Ser Leu Asn Ile Arg Leu Gly Thr
1               5
```

```
<210> SEQ ID NO 25
<211> LENGTH: 12
<212> TYPE: PRT
<213> ORGANISM: Streptococcus pneumoniae

<400> SEQUENCE: 25

Phe Tyr Asn Leu Phe Ser Val Ser Ser Ala Thr Lys
1               5                   10

<210> SEQ ID NO 26
<211> LENGTH: 13
<212> TYPE: PRT
<213> ORGANISM: Streptococcus pneumoniae

<400> SEQUENCE: 26

Val Arg Leu Tyr Val Asn Gly Val Leu Ser Arg Thr Ser
1               5                   10

<210> SEQ ID NO 27
<211> LENGTH: 15
<212> TYPE: PRT
<213> ORGANISM: Streptococcus pneumoniae

<400> SEQUENCE: 27

Lys Gly Arg Val Arg Leu Tyr Val Asn Gly Val Leu Ser Arg Thr
1               5                   10                  15

<210> SEQ ID NO 28
<211> LENGTH: 15
<212> TYPE: PRT
<213> ORGANISM: Pseudomonas aeruginosa

<400> SEQUENCE: 28

Gly Ala Gln Val Glu Val Gly Ser Leu Asn Ile Arg Leu Gly Thr
1               5                   10                  15

<210> SEQ ID NO 29
<211> LENGTH: 15
<212> TYPE: PRT
<213> ORGANISM: Streptococcus pneumoniae

<400> SEQUENCE: 29

Phe Tyr Asn Leu Phe Ser Val Ser Ser Ala Thr Lys Lys Asp Glu
1               5                   10                  15

<210> SEQ ID NO 30
<211> LENGTH: 15
<212> TYPE: PRT
<213> ORGANISM: Pseudomonas aeruginosa

<400> SEQUENCE: 30

Ser Asp Trp Phe Ser Val Ser Ser Asn Ser Leu Tyr Thr Leu Ser
1               5                   10                  15

<210> SEQ ID NO 31
<211> LENGTH: 9
<212> TYPE: PRT
<213> ORGANISM: Streptococcus pneumoniae

<400> SEQUENCE: 31

Ile Arg Asn Leu Thr Val Tyr Asn Arg
1               5
```